United States Patent
Manibusan et al.

(10) Patent No.: US 12,383,620 B2
(45) Date of Patent: Aug. 12, 2025

(54) PHTHALOCYANINE DYE CONJUGATE COMPOSITIONS

(71) Applicant: Rakuten Medical, Inc., San Mateo, CA (US)

(72) Inventors: Anthony Manibusan, San Diego, CA (US); Zahra Shahrokh, Newton, MA (US)

(73) Assignee: Rakuten Medical, Inc., San Diego, CA (US)

( * ) Notice: Subject to any disclaimer, the term of this patent is extended or adjusted under 35 U.S.C. 154(b) by 1096 days.

(21) Appl. No.: 17/057,589

(22) PCT Filed: May 31, 2019

(86) PCT No.: PCT/US2019/035053
§ 371 (c)(1),
(2) Date: Nov. 20, 2020

(87) PCT Pub. No.: WO2019/232478
PCT Pub. Date: Dec. 5, 2019

(65) Prior Publication Data
US 2021/0205455 A1 Jul. 8, 2021

Related U.S. Application Data

(60) Provisional application No. 62/679,747, filed on Jun. 1, 2018.

(51) Int. Cl.
| | |
|---|---|
| *A61K 41/00* | (2020.01) |
| *A61K 45/06* | (2006.01) |
| *A61K 47/10* | (2017.01) |
| *A61K 47/26* | (2006.01) |
| *A61K 47/68* | (2017.01) |

(52) U.S. Cl.
CPC .......... *A61K 41/0071* (2013.01); *A61K 45/06* (2013.01); *A61K 47/10* (2013.01); *A61K 47/26* (2013.01); *A61K 47/6803* (2017.08); *A61K 47/6849* (2017.08)

(58) Field of Classification Search
CPC .............. A61K 9/0019; A61K 47/6803; A61K 47/6849; A61K 47/6835; A61K 47/6875; A61K 47/10; A61K 47/26; A61K 47/68; A61K 47/6801
See application file for complete search history.

(56) References Cited

U.S. PATENT DOCUMENTS

| | | | |
|---|---|---|---|
| 2,915,392 A | 12/1959 | Pedersen | |
| 3,710,795 A | 1/1973 | Higuchi et al. | |
| 5,196,005 A | 3/1993 | Doiron et al. | |
| 5,494,793 A | 2/1996 | Schindele et al. | |
| 5,585,089 A | 12/1996 | Queen et al. | |
| 6,991,790 B1 * | 1/2006 | Lam | C07K 16/2896 424/152.1 |
| 7,005,518 B2 | 2/2006 | Peng et al. | |
| 7,498,029 B2 | 3/2009 | Hasan et al. | |
| 8,524,239 B2 | 9/2013 | Kobayashi | |
| 8,623,354 B2 | 1/2014 | Brown et al. | |
| 9,358,306 B2 | 6/2016 | Kobayashi | |
| 10,064,943 B2 | 9/2018 | Dilley et al. | |
| 10,295,719 B2 | 5/2019 | Rose et al. | |
| 10,416,366 B2 | 9/2019 | Rose et al. | |
| 10,527,771 B2 | 1/2020 | Rose et al. | |
| 10,537,641 B2 | 1/2020 | Kobayashi | |
| 10,538,590 B2 | 1/2020 | Kobayashi | |
| 10,588,972 B2 | 3/2020 | Kovar | |
| 11,013,803 B2 | 5/2021 | Kobayashi | |
| 11,141,483 B2 | 10/2021 | Makings et al. | |
| 11,364,297 B2 | 6/2022 | Kobayashi et al. | |
| 11,364,298 B2 | 6/2022 | Kobayashi et al. | |
| 2001/0044124 A1 | 11/2001 | Bacus | |
| 2004/0171827 A1 | 9/2004 | Peng et al. | |
| 2005/0147612 A1 | 7/2005 | Yayon et al. | |
| 2005/0220786 A1 * | 10/2005 | Mahler | A61K 47/02 514/53 |
| 2006/0188509 A1 | 8/2006 | Derynck et al. | |
| 2007/0042398 A1 | 2/2007 | Peng et al. | |

(Continued)

FOREIGN PATENT DOCUMENTS

| | | |
|---|---|---|
| CN | 101023084 | 8/2007 |
| CN | 102585003 | 7/2012 |
| CN | 103781495 | 5/2014 |
| JP | 2014523907 | 9/2014 |
| JP | 2017524002 | 8/2017 |
| WO | WO 2004038378 | 5/2004 |
| WO | WO 2005099689 | 10/2005 |

(Continued)

OTHER PUBLICATIONS

Mahler (European Journal of Pharmaceutics and Biopharmaceutics, 2005, vol. 59, pp. 407-417) (Year: 2005).*

(Continued)

*Primary Examiner* — Karen A. Canella
(74) *Attorney, Agent, or Firm* — Morrison & Foerster LLP

(57) ABSTRACT

Provided are compositions containing a conjugate containing a phthalocyanine dye, including compositions containing stabilizing agents, such as non-ionic surfactants and/or protectants. In some aspects, the compositions result reduced aggregation of the conjugate due to agitation, temperature exposure, and/or pH. Also provided are articles of manufacture containing the compositions containing the conjugates, and methods for their administration to subjects for photoimmunotherapy. In some embodiments, the phthalocyanine dye conjugates are conjugated to a targeting molecule, such as an antibody, that targets the conjugate to a cell or pathogen, such as by binding to a cell surface protein.

8 Claims, 25 Drawing Sheets

(56) References Cited

U.S. PATENT DOCUMENTS

| | | |
|---|---|---|
| 2008/0073566 A1 | 3/2008 | Frangioni |
| 2008/0095950 A1 | 4/2008 | Hall-Goulle et al. |
| 2008/0253960 A1 | 10/2008 | Zheng et al. |
| 2012/0010558 A1 | 1/2012 | Hisataka et al. |
| 2013/0039861 A1 | 2/2013 | Regino et al. |
| 2013/0287688 A1 | 10/2013 | Jain et al. |
| 2013/0336995 A1 | 12/2013 | Kobayashi et al. |
| 2014/0120119 A1 | 5/2014 | Kobayashi |
| 2014/0314778 A1 | 10/2014 | Alavattam |
| 2015/0071923 A1* | 3/2015 | Wei .......... A61P 15/00 435/69.6 |
| 2015/0343060 A1 | 12/2015 | Kovar |
| 2015/0343084 A1 | 12/2015 | Dilley |
| 2015/0374819 A1 | 12/2015 | Kovar |
| 2016/0256564 A2 | 1/2016 | Kobayashi et al. |
| 2017/0122853 A1 | 5/2017 | Kobayashi et al. |
| 2018/0113246 A1 | 4/2018 | Rose et al. |
| 2018/0113247 A1 | 4/2018 | Rose et al. |
| 2018/0236076 A1 | 8/2018 | Kobayashi et al. |
| 2018/0239074 A1 | 8/2018 | Rose et al. |
| 2018/0250405 A1 | 9/2018 | Biel et al. |
| 2018/0339048 A1 | 11/2018 | Dilley et al. |
| 2019/0015510 A1 | 1/2019 | Makings et al. |
| 2019/0070296 A1 | 3/2019 | Wang et al. |
| 2019/0282696 A1 | 9/2019 | Biel et al. |
| 2019/0365897 A1 | 12/2019 | Garcia-Guzman et al. |
| 2020/0085950 A1 | 3/2020 | Kobayashi et al. |
| 2020/0095331 A1 | 3/2020 | Kobayashi et al. |
| 2020/0166690 A1 | 5/2020 | Rose et al. |
| 2020/0179514 A1 | 6/2020 | Kovar |
| 2021/0010914 A1 | 1/2021 | Kobayashi et al. |
| 2021/0079112 A1 | 3/2021 | Kobayashi et al. |
| 2021/0401986 A1 | 12/2021 | Makings et al. |
| 2022/0288208 A1 | 9/2022 | Manibusan et al. |
| 2022/0288210 A1 | 9/2022 | Kobayashi et al. |
| 2023/0050584 A1 | 2/2023 | Kobayashi et al. |

FOREIGN PATENT DOCUMENTS

| | | |
|---|---|---|
| WO | WO 2007092772 | 8/2007 |
| WO | WO 2007147001 | 12/2007 |
| WO | WO 2008045373 | 4/2008 |
| WO | WO 2010047611 | 4/2010 |
| WO | WO 2011039510 | 4/2011 |
| WO | WO 2011039511 | 4/2011 |
| WO | WO 2013009475 | 1/2013 |
| WO | WO 2014084394 | 6/2014 |
| WO | WO 2014120974 | 8/2014 |
| WO | WO 2014160497 | 10/2014 |
| WO | WO 2014176284 | 10/2014 |
| WO | WO 2015187651 | 12/2015 |
| WO | WO 2015187677 | 12/2015 |
| WO | WO 2016022896 | 2/2016 |
| WO | WO 2017027247 | 2/2017 |
| WO | WO 2017031363 | 2/2017 |
| WO | WO 2017031367 | 2/2017 |
| WO | WO 2017040384 | 3/2017 |
| WO | WO 2018080952 | 5/2018 |
| WO | WO 2018156815 | 8/2018 |
| WO | WO 2019009941 | 1/2019 |
| WO | WO 2019036249 | 2/2019 |
| WO | WO 2021026393 | 2/2021 |

OTHER PUBLICATIONS

Warne (European Journal of Pharmaceutics and Biopharmaceuticals, 2011, vol. 78, pp. 208-212) (Year: 2011).*

Lowe et al (Aggregation, Stability, and Formulation of Human Antibody Therapeutics, In: Advances in Protein Chemistry and Structural Biology, 2011, vol. 48, pp. 41-61) (Year: 2011).*

Kang et al (BioProcess International, 2016, vol. 14, pp. 40-45) (Year: 2016).*

Amoury et al., "Photoimmunotheranostic agents for triple-negative breast cancer diagnosis and therapy that can be activated on demand," Oncotarget. (2016) 7(34):54925-54936.

Ballou et al., "Tumor labeling in vivo using cyanine-conjugated monoclonal antibodies." Cancer Immunol Immunother. Oct. 1995;41(4):257-63.

Barrett et al., "In vivo diagnosis of epidermal growth factor receptor expression using molecular imaging with a cocktail of optically labeled monoclonal antibodies," Clin Cancer Res. Nov. 15, 2007;13(22 Pt 1):6639-48.

Butcher et al., "Visible Light," Tour of the Electromagnetic Spectrum, National Aeronautics and Space Administration, 2016, available at https://smd-prod.s3.amazonaws.com/science-pink/s3fs-public/atoms/files/Tour-of-the-EMS-TAGGED-v7_0.pdf.

Carcenac et al., "Internalisation enhances photo-induced cytotoxicity of monoclonal antibody-phthalocyanine conjugates." British Journal of Cancer, Nov. 30, 2001, vol. 85, No. 11, pp. 1787-1793.

Chen et al., "Tumor vascular permeabilization by vascular-targeting photosensitization: effects, mechanism, and therapeutic implications," Clin Cancer Res. 12:917-923, 2006.

Chopra, "IRDye 700DX-Labeled annexin V," Molecular Imaging and Contrast Agent Database (MICAD) [Internet]. Bethesda (MD): National Center for Biotechnology Information (US); 2004-2013. Oct. 27, 2009 [updated Dec. 17, 2009].

Chothia et al., "Canonical Structures for the Hypervariable Regions of Immunoglobulins," J Mol Biol. Aug. 20, 1987;196(4):901-17.

Del Governatore et al., "Experimental Photoimmunotherapy of Hepatic Metastases of Colorectal Cancer with a 17.1A Chlorine6 Immunoconjugate," Cancer Res. 60:4200-4205, 2000.

Doane et al., "Observation and Photophysical Characterization of Silicon Phthalocyanine J-Aggregate Dimers in Aqueous Solutions," Chem Eur J. 20:8030-8039, 2014.

Duska et al., "Combination Photoimmunotherapy and Cisplatin: Effects on Human Ovarian Cancer Ex Vivo," J Nat Cancer Inst. 91:1557-1563, 1999.

Gao et al., "In vivo cancer targeting and imaging with semiconductor quantum dots," Nat Biotechnol. Aug. 2004;22(8):969-76.

Gleysteen et al., "Fluorescently Labeled Cetuximab to Evaluate Head and Neck Cancer Response to Treatment," Cancer Biology & Therapy. 2007 6(8):e1-e5.

Gleysteen et al., "Update on Aspyrian Trial: Study of RM-1929 and Photoimmunotherapy in Patients with Recurrent Head and Neck Cancer," Abstract, submitted for 2017 Combined Otolaryngology Spring Meetings, American Head and Neck Cancer Society, Apr. 26, 2017, San Diego, CA, available online at: https://www.researchposters.com/display_posters.aspx?page=eposter&code=COSM2017.

Gleysteen et al., "Update on Aspyrian Trial: Study of RM-1929 and Photoimmunotherapy in Patients with Recurrent Head and Neck Cancer," Poster, Presented at 2017 Combined Otolaryngology Spring Meetings, American Head and Neck Cancer Society, Apr. 26, 2017, San Diego, CA, available online at https://www.researchposters.com/Posters/COSM/COSM2017/B043.pdf.

Greish, K., "Enhanced permeability and retention of macromolecular drugs in solid tumors: a royal gate for targeted anticancer nanomedicines," J Drug Target. 15:457-464, 2007.

Han, Weiwei, Radio Exploration of the Four Colors, Jilin Fine Arts Publishing House, Jan. 2014, p. 139.

Hanaoka et al., "Glypican-3 targeted human heavy chain antibody as a drug carrier for hepatocellular carcinoma therapy," Mol Pharm. Jun. 1, 2015;12(6):2151-7.

Hanaoka et al., "Photoimmunotherapy of hepatocellular carcinoma-targeting Glypican-3 combined with nanosized albumin-bound paclitaxel," Nanomedicine (Lond). (2015);10(7):1139-47.

Heukers et al., "Nanobody-photosensitizer conjugates for targeted photodynamic therapy," Nanomedicine (2014) 10(7):1441-51.

Hiroshima et al., "Photoimmunotherapy Inhibits Tumor Recurrence After Surgical Resection on a Pancreatic Cancer Patient-Derived Orthotopic Xenograft (PDOX) Nude Mouse Model," Ann Surg Oncol. Dec. 2015; 22 Suppl 3:S1469-74.

Ishida et al., "Trastuzumab-Based Photoimmunotherapy Integrated with Viral HER2 Transduction Inhibits Peritoneally Disseminated HER2-Negative Cancer," Mol Cancer Ther. Mar. 2016;15(3):402-11.

(56) References Cited

OTHER PUBLICATIONS

Ishii et al., "Defucosylated Humanized Anti-CCR4 Monoclonal Antibody KW-0761 as a Novel Immunotherapeutic Agent for Adult T-cell Leukemia/Lymphoma," Clin Cancer Res. 16:1520-1531, 2010.
Ito et al., "Combination photoimmunotherapy with monoclonal antibodies recognizing different epitopes of human epidermal growth factor receptor 2: an assessment of phototherapeutic effect based on fluorescence molecular imaging," Oncotarget. Mar. 22, 2016;7(12):14143-52.
Ito et al., "Molecular targeted photoimmunotherapy for HER2-positive human gastric cancer in combination with chemotherapy results in improved treatment outcomes through different cytotoxic mechanisms," BMC Cancer. Jan. 25, 2016;16:37.
Ito et al., "Near-Infrared Photochemoimmunotherapy by Photoactivatable Bifunctional Antibody-Drug Conjugates Targeting Human Epidermal Growth Factor Receptor 2 Positive Cancer," Bioconjugate Chemistry (2017) 28(5):1458-1469.
Jeong et al., "Indium gallium nitride-based ultraviolet, blue, and green lightemitting diodes functionalized with shallow periodic hole patterns," (2017) Scientific Reports 7:45726.
Jing et al., "Imaging and Selective Elimination of Glioblastoma Stem Cells with Theranostic Near-Infrared-Labeled CD133-Specific Antibodies," Theranostics. Apr. 12, 2016;6(6):862-74.
Kang et al., "Rapid Formulation Development for Monoclonal Antibodies," 2016, https://bioprocessintl.com/manufacturing/formulation/rapid-formulation-development-for-monoclonal-antibodies/.
Kishimoto et al., "Evaluation of oxygen dependence on in vitro and in vivo cytotoxicity of photoimmunotherapy using IR-700-antibody conjugates," Free Radic Biol Med. Aug. 2015;85:24-32.
Kobayashi, "Activatable Fluorescent Imaging Probes for Cancer Detection and Diagnosis," Abstract presented at the American Chemical Society meeting in San Francisco, 2014.
Kobayashi, "Near infrared photoimmunotherapy: A new cancer therapy kills cancer cells with exposure of harmless near infrared light," Poster Presentation, at NEST Conference, Tokyo, Japan, Apr. 2018.
Kochuparambil et al., "A Phase 1, Multicenter, Open-label, Dose-escalation, Combination Study of RM-1929 and Photoimmunotherapy in Patients with Recurrent Head and Neck Cancer," Abstract, Annals of Oncology, vol. 28, Issue suppl_5, Sep. 1, 2017, mdx374.008, Published: Sep. 18, 2017, available online at: https://doi.org/10.1093/annonc/mdx374.008.
Kochuparambil et al., "A Phase 1, Multicenter, Open-label, Dose-escalation, Combination Study of RM-1929 and Photoimmunotherapy in Patients with Recurrent Head and Neck Cancer," Poster, Presented at 2017 European Society for Medical Oncology, Sep. 8-12, 2017, Madrid, Spain.
Kovar et al., "A Systematic Approach to the Development of Fluorescent Contrast Agents for Optical Imaging of Mouse Cancer Models," Anal. Biochem. 367(1): 1-12, 2007.
Licor, "High Photostability of IRDye® 700DX," Retrieved on Aug. 23, 2018. Retrieve on https://www.licor.com/bio/products/reagents/irdye/700dx/photostability.html.
Li-Cor, "IRDye® Infrared Dyes: Advancing Discovery with Infrared Imaging," 2010.
Maawy et al., "Near infra-red photoimmunotherapy with anti-CEA-IR700 results in extensive tumor lysis and a significant decrease in tumor burden in orthotopic mouse models of pancreatic cancer," PLoS One. (Mar. 23, 2015;10(3):e0121989.
Maawy et al., "Photoimmunotherapy lowers recurrence after pancreatic cancer surgery in orthotopic nude mouse models," J Surg Res. Jul. 2015; 197(1):5-11.
Mitsunaga et al., "Abstract 3618: Target-Specific Photo-Activatable Immunotherapy (PIT) for Cancer Based on a Monoclonal Antibody-Photosensitizer Conjugate," in Proceedings of the 102nd Annual Meeting of the American Association for Cancer Research; Apr. 2-6, 2011; Orlando, FL. Philadelphia (PA): AACR; Cancer Res. 71:3618, 2011.
Mitsunaga et al., "Cancer cell-selective in vivo near infrared photoimmunotherapy targeting specific membrane molecules," Nat Med. Nov. 6, 2011;17(12):1685-91.
Mitsunaga et al., "Immediate in vivo target-specific cancer cell death after near infrared photoimmunotherapy," BMC Cancer. Aug. 8, 2012;12:345.
Mitsunaga et al., "Near-infrared theranostic photoimmunotherapy (PIT): repeated exposure of light enhances the effect of immunoconjugate," Bioconjug Chem. Mar. 21, 2012;23(3):604-9.
Moore et al., "Photoimmunotherapy of residual disease after incomplete surgical resection in head and neck cancer models," Cancer Med. Jul. 2016;5(7):1526-34.
Nagaya et al., "Host Immunity Following Near-Infrared Photoimmunotherapy Is Enhanced with PD-1 Checkpoint Blockade to Eradicate Established Antigenic Tumors," Cancer Immunol Res. 7(3):401-413, 2019.
Nagaya et al., "Improved micro-distribution of antibody-photon absorber conjugates after initial near infrared photoimmunotherapy (NIR-PIT)," J Control Release. Jun. 28, 2016;232:1-8.
Nagaya et al., "Near infrared photoimmunotherapy of B-cell lymphoma," Mol Oncol. Jul. 29, 2016 10(9):1404-1414.
Nagaya et al., "Near infrared photoimmunotherapy targeting bladder cancer with a canine anti-epidermal growth factor receptor (EGFR) antibody," Oncotarget 9:19026-19038, 2018.
Nagaya et al., "Near Infrared Photoimmunotherapy Targeting EGFR Positive Triple Negative Breast Cancer: Optimizing the Conjugate-Light Regimen," PLoS One. Aug. 27, 2015;10(8):e0136829.
Nagaya et al., "Near infrared photoimmunotherapy with an anti-mesothelin antibody," Oncotarget. Apr. 26, 2016;7(17):23361-9.
Nagaya et al., "Near infrared photoimmunotherapy with avelumab, an anti-programmed death-ligand 1 (PD-L1) antibody," Oncotarget 8:8807-8817, 2017.
Nagaya et al., "Syngeneic Mouse Models of Oral Cancer Are Effectively Targeted by Anti-CD44-Based NIR-PIT," Mol Cancer Res. 15:1667-1677, 2017.
Nakajima et al., "Improving the efficacy of Photoimmunotherapy (PIT) using a cocktail of antibody conjugates in a multiple antigen tumor model," Theranostics. Apr. 23, 2013;3(6):357-65.
Nakajima et al., "Real-time monitoring of in vivo acute necrotic cancer cell death induced by near infrared photoimmunotherapy using fluorescence lifetime imaging," Cancer Res. Sep. 15, 2012;72(18):4622-8.
Nakajima et al., "The effects of conjugate and light dose on photo-immunotherapy induced cytotoxicity," BMC Cancer. May 30, 2014;14:389.
Nakamura et al., "MR imaging biomarkers for evaluating therapeutic effects shortly after near infrared photoimmunotherapy," Oncotarget. Mar. 29, 2016;7(13):17254-64.
National Optical Astronomy Observatory, "Recommended Light Levels," retrieved from https://www.noao.edu/education/QLTkit/ACTIVITY_Documents/Safety/LightLevels_outdoor+indoor.pdf.
Nelson, "Trehalose: A Powerful Excipient in the Formulation Toolbox," 2015, https://drug-dev.com/trehalose-a-powerful-excipient-in-the-formulation-toolbox/.
New Pharmacology (New Yakurigaku), Nankodo Co., Ltd., 2012, the third impression of the revised sixth edition, p. 558-559. (In Japanese, with translation).
North et al., "A new clustering of antibody CDR loop conformations," J Mol Biol. Feb. 18, 2011; 406(2): 228-256.
Nowis et al., "The influence of photodynamic therapy on the immune response," Photodiagnosis Photodyn Ther. Dec. 2005;2(4):283-98.
Ogawa et al., "In vivo molecular imaging of cancer with a quenching near-infrared fluorescent probe using conjugates of monoclonal antibodies and indocyanine green," Cancer Res. Feb. 15, 2009;69(4):1268-72.
Peng et al., "Phthalocyanine dye as an extremely photostable and highly fluorescent near-infrared labeling reagent," Proc SPIE Int Soc Opt Eng. vol. 6097, 60970E (2006).
Rakuten Medical, "An open-label study using ASP-1929 photoimmunotherapy in combination with anti-PD1 therapy in EGFR expressing advanced solid tumors," Mar. 12, 2020, https://clinicaltrials.

(56) References Cited

OTHER PUBLICATIONS gov/ct2/show/record/NCT04305795?term=rakuten&draw=2&rank=1 [retrieved on Dec. 2, 2020].
Rosas-Arellano et al., "A simple solution for antibody signal enhancement in immunofluorescence and triple immunogold assays," Histochem Cell Biol (2016) 146:421-430.
Sano et al., "Acute cytotoxic effects of photoimmunotherapy assessed by 18F-FDG PET," J Nucl Med. May 2013;54(5):770-5.
Sano et al., "The effect of photoimmunotherapy followed by liposomal daunorubicin in a mixed tumor model: a demonstration of the super-enhanced permeability and retention effect after photoimmunotherapy," Mol Cancer Ther. Feb. 2014;13(2):426-32.
Sano et al., "Markedly Enhanced Permeability and Retention Effects Induced by Photo-Immunotherapy of Tumors," ACS Nano. Jan. 22, 2013; 7:717-724.
Sato et al., "Comparative effectiveness of light emitting diodes (LEDs) and Lasers in near infrared photoimmunotherapy," Oncotarget. Mar. 22, 2016;7(12):14324-35.
Sato et al., "Near infrared photoimmunotherapy for lung metastases," Cancer Lett. Aug. 28, 2015;365(1):112-21.
Sato et al., "Near infrared photoimmunotherapy in the treatment of disseminated peritoneal ovarian cancer," Mol Cancer Ther. Jan. 2015;14(1):141-50.
Sato et al., "Near infrared photoimmunotherapy in the treatment of pleural disseminated NSCLC: preclinical experience," Theranostics. Mar. 19, 2015;5(7):698-709.
Sato et al., "Photoimmunotherapy of gastric cancer peritoneal carcinomatosis in a mouse model," PLoS One. Nov. 17, 2014;9(11):e113276.
Sato et al., "Photoimmunotherapy: comparative effectiveness of two monoclonal antibodies targeting the epidermal growth factor receptor," Mol Oncol. May 2014;8(3):620-32.
Sato et al., "Photoinduced Ligand Release from a Silicon Phthalocyanine Dye Conjugated with Monoclonal Antibodies: A Mechanism of Cancer Cell Cytotoxicity after Near-Infrared Photoimmunotherapy," ACS Cent Sci. 4:1559-1569, 2018.
Sato et al., "Selective cell elimination in vitro and in vivo from tissues and tumors using antibodies conjugated with a near infrared phthalocyanine," RSC Adv. Mar. 3, 2015;5(32):25105-25114.
Sato et al., "Spatially selective depletion of tumor-associated regulatory T cells with near-infrared photoimmunotherapy." Sci Transl Med. Aug. 17, 2016;8(352):352ra110.
Serebrovskaia et al., "Genetically Encoded Photoimmunosensitizer," abstract (in English); Bioorg. Khim. 2011 37(1):137-44.
Serebrovskaya et al., "Targeting Cancer Cells by Using an Antireceptor Antibody-Photo sensitizer Fusion Protein," Proc Nat Acad Sci. 106:9221-9225, 2009.
Snyder et al., "Photodynamic therapy: a means to enhanced drug delivery to tumors," Cancer Res. 63:8126-8131, 2003.
Soukos et al., "Epidermal Growth Factor Receptor-Targeted Immunophotodiagnosis and Photoimmunotherapy of Oral Precancer in Vivo," Cancer Res. 61 :4490-4496, 2001.
Steele et al., "Suppressor deletion therapy: selective elimination of T suppressor cells in vivo using a hematoporphyrin conjugated monoclonal antibody permits animals to reject syngeneic tumor cells." Cancer Immunol Immunother. 1988;26(2):125-31.
Steiner et al., "Efficient Selection of DARPins with Sub-nanomolar Affinities using SRP Phage Display," J Mol Biol (2008) 382(5):1211-1227.
Sugiyama et al., "Anti-CCR4 mAb selectively depletes effector-type FoxP3+CD4+ regulatory T cells, evoking antitumor immune responses in humans." Proc Natl Acad Sci USA. Oct. 29, 2013;110(44):17945-50.
Supplementary materials from Mitsunaga et al., "Cancer Cell-Selective in Vivo Near Infrared Photomimmunotherapy Targeting Specific Membrance Molecules," Nat. Med. 17:1685-1691, 2011.
Supplementary materials from Sugiyama et al., "Anti-CCR4 mAb selectively depletes effector-type FoxP3+CD4+ regulatory T cells, evoking antitumor immune responses in humans." Proc Natl Acad Sci U S A. Oct. 29, 2013;110(44):17945-50.

Tamaskovic et al., "Designed ankyrin repeat proteins (DARPins) from research to therapy," Methods Enzymol (2012) 503:101-134.
U.S. Department of Veterans Affairs, "Lighting Design Manual," Dec. 2015, retrieved from https://www.cfm.va.gov/til/dManual/dmLighting.pdf.
U.S. Environmental Protection Agency, "Laboratories for the 21st Century: Best Practice Guide," Aug. 2006, U.S. Environmental Protection Agency, retrieved from http://labs21.lbl.gov/docs/Lighting_reduced_R11.pdf.
van Driel et al., "EGFR targeted nanobody-photosensitizer conjugates for photodynamic therapy in a pre-clinical model of head and neck cancer," J Control Release. May 10, 2016;229:93-105.
von Felbert et al., "A specific photoimmunotheranostics agent to detect and eliminate skin cancer cells expressing EGFR," J Cancer Res Clin Oncol. May 2016;142(5):1003-11.
Vrouenraets et al., "Targeting of aluminum (III) phthalocyanine tetrasulfonate by use of internalizing monoclonal antibodies: improved efficacy in photodynamic therapy." Cancer Research, Mar. 1, 2001, vol. 61, No. 5, pp. 1970-1975.
Waite and Roth, "Nanoscale drug delivery systems for enhanced drug penetration into solid tumors: current progress and opportunities," Crit Rev Biomed Eng. 40:21-41, 2012.
Wang et al., "Theranostic Agents for Photodynamic Therapy of Prostate Cancer by Targeting Prostate-Specific Membrane Antigen," Mol Cancer Ther. Aug. 2016;15(8):1834-44.
Wang, Changhui et al., New Progress in the Diagnosis and Treatment of Respiratory Interventional Therapy, Shanghai Science and Technology Press, Jun. 2015, p. 152.
Watanabe et al., "Photoimmunotherapy targeting prostate-specific membrane antigen: are antibody fragments as effective as antibodies? ," J Nucl Med. Jan. 2015 56(1):140-4.
Wessels et al., "Advances in cellular, subcellular, and nanoscale imaging in vitro and in vivo," Cytometry A:77:667-676, 2010.
Whiteside, "The tumor microenvironment and its role in promoting tumor growth," Oncogene (2008) 27(45):5904-5912.
Xu, Deyu et al., Tumor Photodynamic Therapy Principles, Drugs, and Clinical Introduction, China Medical Science and Technology Press, May 1996, pp. 172-174.
Zinn et al., "IND-Directed Safety and Biodistribution Study of Intravenously Injected Cetuximab-IRDye800 in Cynomolgus Macaques." Molecular Imaging Biology, Feb. 5, 2015, vol. 17, No. 1, pp. 49-57.
Alegria-Schaffer, "General Protein-Protein Cross-Linking," Methods Enzymol (2014) 539:81-87.
Bartl et al., "Emissivity of aluminium and its importance for radiometric measurement," Measurement of Physical Quantities (2004) 31-36.
BIO Clinica, 2004, vol. 19, p. 398-403 (In Japanese, with concise description in English).
Carcenac et al., "Preparation, Phototoxicity and Biodistribution Studies of Anti-Carcinoembryonic Antigen Monoclonal Antibody-Phthalocyanine Conjugates," Photochemistry and Photobiology 70(6): 930-936 [1999].
Cheng et al., "Near infrared light-triggered drug generation and release from gold nanoparticle carriers for photodynamic therapy," Small (2014) 10(9):1799-1804.
Dancey et al., "Phase I Trial of 1311-Labelled Anti-CD25 Antibody Basiliximab in the Treatment of Patients with Relapsed or Refractory Lymphoma," Blood (2007) 110(11):648.
Fujimura et al., 'Conjugation Ratio, Light Dose, and pH Affect the Stability of Panitumumab IR700 for Near-Infrared Photoimmunotherapy', ACS Med. Chem. Lett. 2020, 11, 1598-1604.
Goswami et al. "Developments and challenges for mAb-based therapeutics." *Antibodies* 2.3 (2013): 452-500.
Kuhn et al., "The Role of Interleukin-2 Receptor Alpha in Cancer," Frontiers in Bioscience (2005) 10:1462-1474.
Li et al., "A Novel Tumor Targeting Drug Carrier for Optical Imaging and Therapy," Theranostics (2014) 4(6):642-659.
Li et al., "Structural basis for inhibition of the epidermal growth factor receptor by cetuximab," Cancer Cell Apr. 2005;7(4):301-11.
Medical Sci Digest., 2004, vol. 30, p. 545-548 (In Japanese, with concise description in English).

(56) References Cited

OTHER PUBLICATIONS

Rosenthal et al., "In Vivo Detection of Head and Neck Cancer Orthotopic Xenografts by Immunofluorescence," Laryngoscope (2006) 116:1636-1641.
Sasikumar et al., "Small-molecule Immune Checkpoint Inhibitors Targeting PD-1/PD-L1 and Other Emerging Checkpoint Pathways, " BioDrugs (2018) 32:481-497.
Sekkat et al., "Like a bolt from the Blue: Phthalocyanines in Biomedical Optics," Molecules (2012) 17:98-144.
Vrouenraets et al., "Comparison of Aluminium (III) Phthalocyanine Tetrasulfonate and Meta-Tetra Hydroxyphenylchlorin-Monoclonal Antibody Conjugates for Their Efficacy in Photodynamic Therapy In Vitro," Int. J. Cancer: 98, 793-798 [2002].
Wagner-Rousset et al., "Antibody-drug conjugate model fast characterization by LC-MS following IdeS proteolytic digestion," mAbs (2014) 6(1):173-184.
Wang et al. "Antibody structure, instability, and formulation." Journal of pharmaceutical sciences 96.1 (2007): 1-26.
Chung et al. (Mar. 13, 2008), "Cetuximab-Induced Anaphylaxis and IgE Specific for Galactose-α-1,3-Galactose," N Engl J Med., 2008, 358(11), 9 pages.
De Goejj et al. (Nov. 2016), "Efficient Payload Delivery by a Bispecific Antibody-Drug Conjugate Targeting HER2 and CD63," Mol. Cancer Ther., 2016, 15(11), 10 pages.
Mitsunaga et al., "Cancer cell-selective in vivo near infrared photoimmunotherapy targeting specific membrane molecules," Nat Med. Nov. 6, 2011;17(12): Supplemental Information.
Mittendorf et al. (Apr. 2014), "PD-L1 expression in triple-negative breast cancer," *Cancel Immunol Res*, 2014, 2(4), 10 pages.

\* cited by examiner

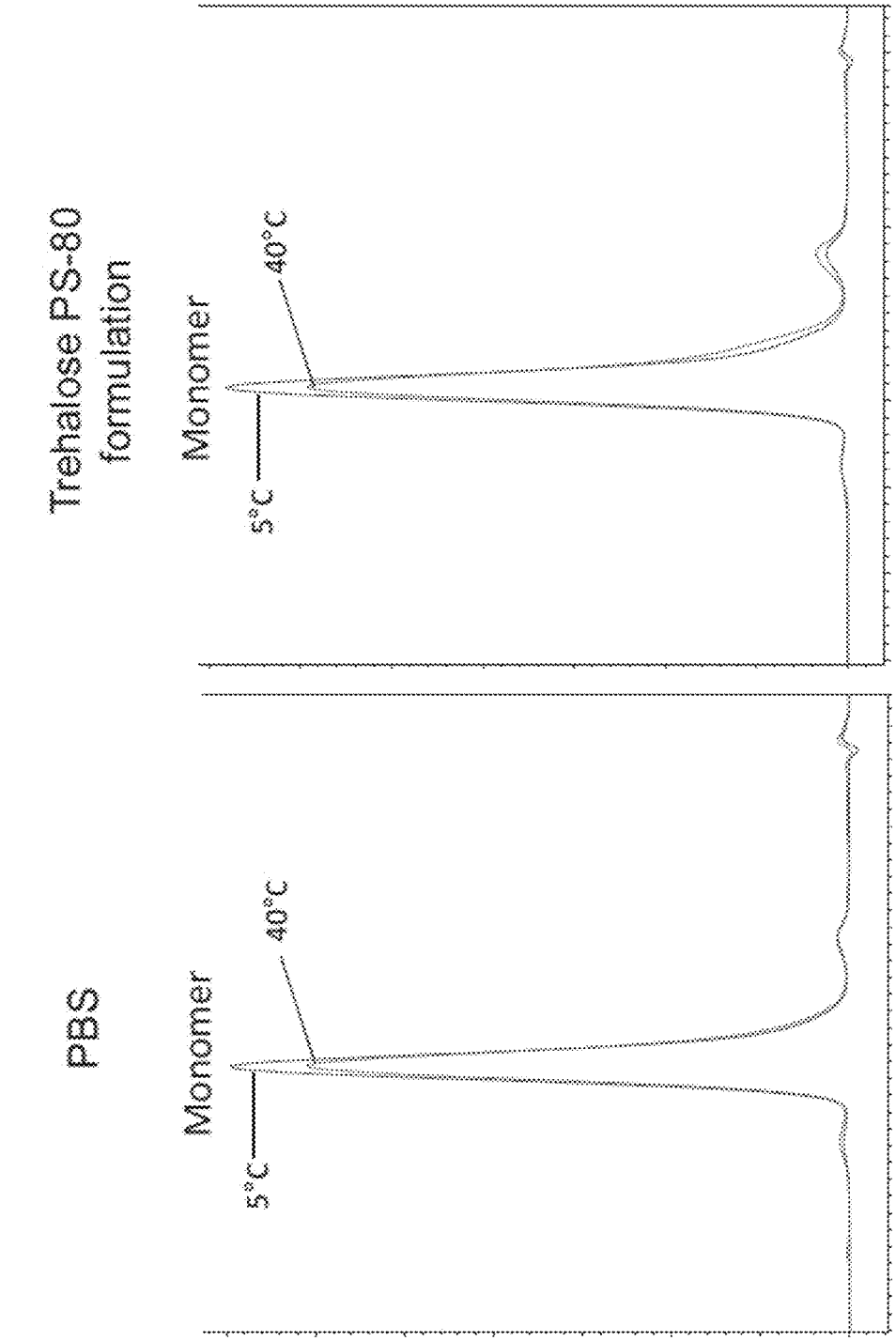

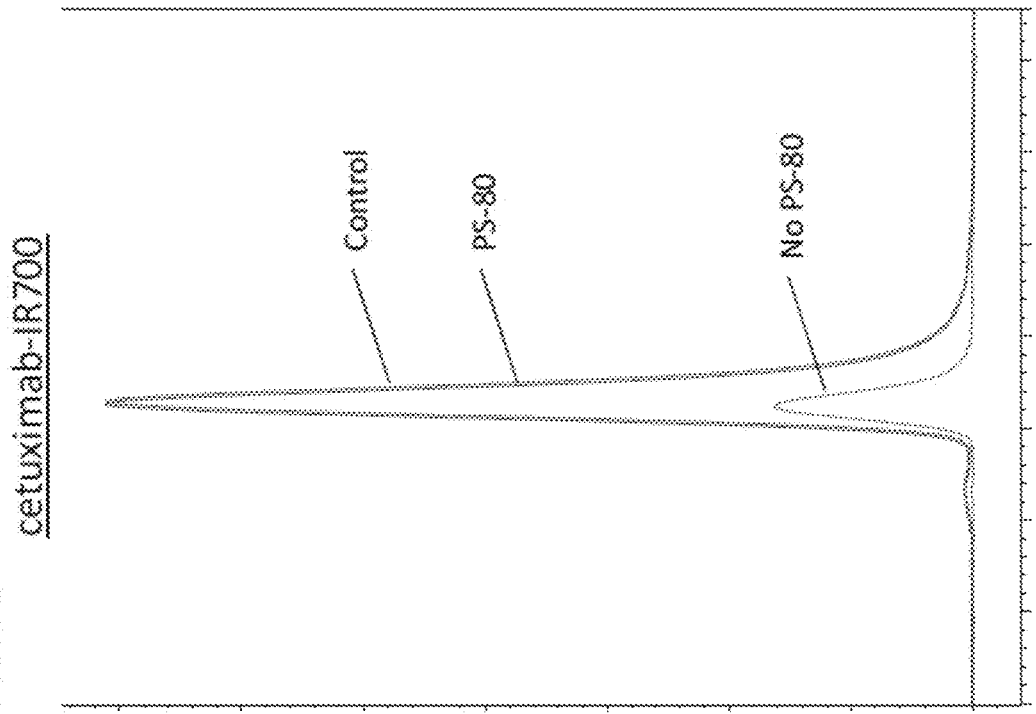
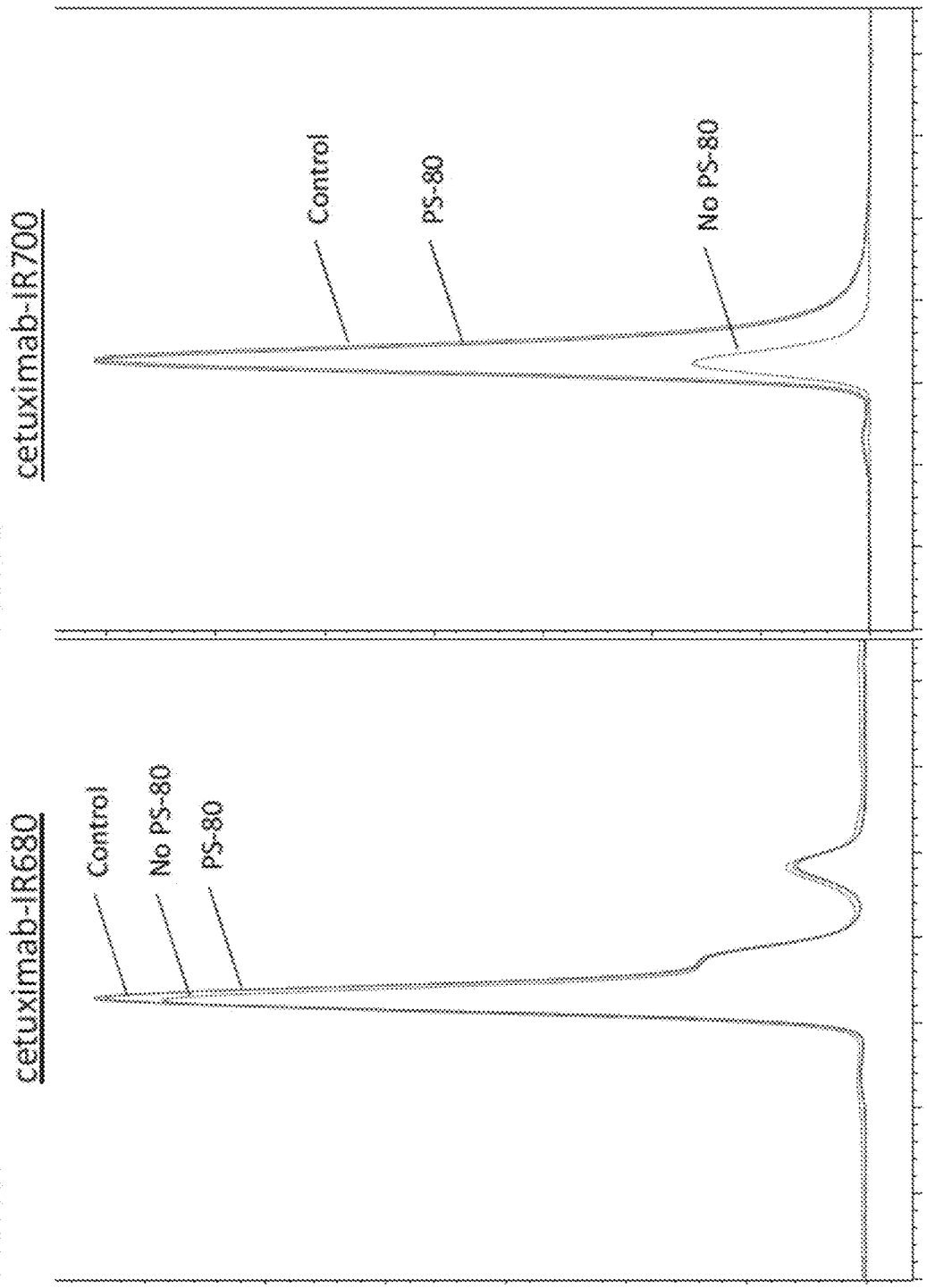
FIG. 7A
FIG. 7B

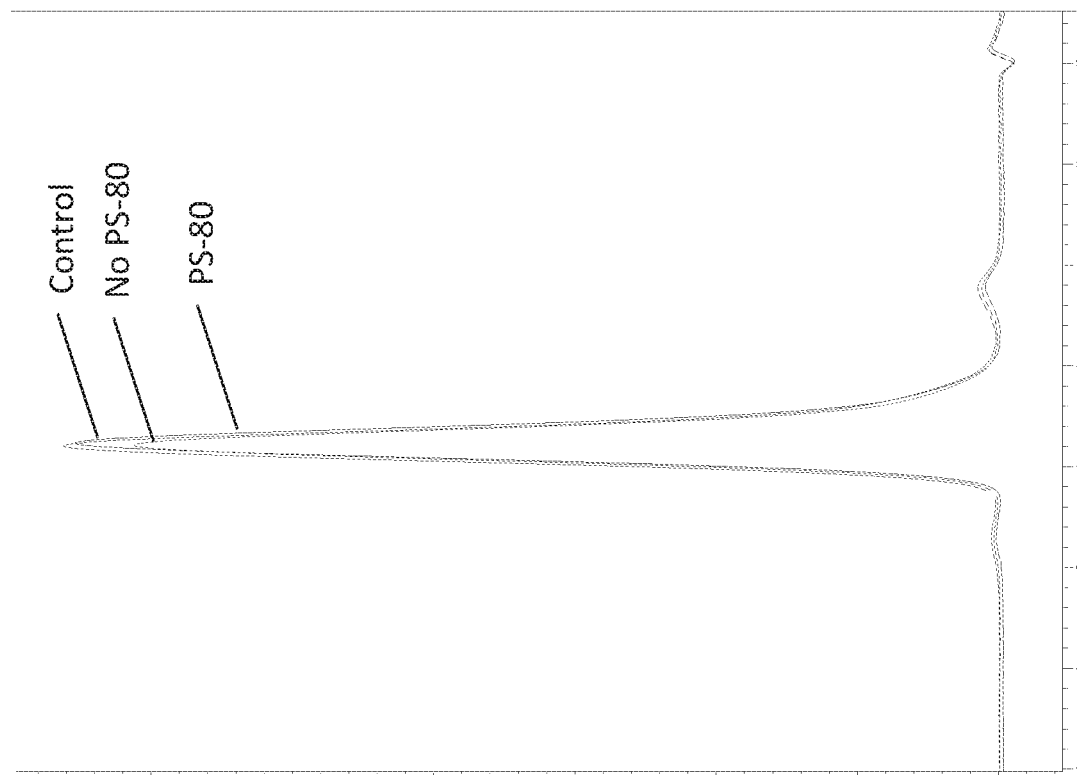

PHTHALOCYANINE DYE CONJUGATE COMPOSITIONS

CROSS-REFERENCE TO RELATED APPLICATIONS

This application is a national stage application under 35 U.S.C. § 371 of International Application No. PCT/US2019/035053, filed internationally on May 31, 2019, which claims priority from U.S. provisional application No. 62/679,747, filed Jun. 1, 2018, entitled "PHTHALOCYANINE DYE CONJUGATE COMPOSITIONS," the contents of which are incorporated by reference in their entirety.

FIELD

The present disclosure relates in some aspects to compositions containing a conjugate containing a phthalocyanine dye and one or more stabilizing agents. In some aspects, the compositions containing the conjugate are more stable and/or less prone to aggregation with the stabilizing agent than compositions that do not contain the stabilizing agent. In some aspects, the disclosure further relates to articles of manufacture containing the compositions and to methods for their administration to subjects for photoimmunotherapy. In some embodiments, the conjugate included in the compositions described herein contains a phthalocyanine dye linked to an antibody, for example an antibody-IR700 conjugate, such as a cetuximab-IR700 conjugate.

BACKGROUND

Various therapies are available for treating disease, such as cancer. For example, photoimmunotherapy (PIT) is a method that uses a photosensitizer conjugated to an antibody or other targeting molecule to target to a cell surface target molecule, e.g., a cell surface receptor, in order to permit the targeted killing of specific cells. In some cases, PIT can selectively target disease cells, such as tumor cells, and thereby selectively kill such cells without damaging healthy cells. Improved strategies are needed to improve phthalocyanine dye conjugates for use in PIT. Provided are compositions and methods that meet such needs.

SUMMARY

Provided in some embodiments is a pharmaceutical composition containing a conjugate, such as an antibody-IR700 conjugate, that exhibits reduced aggregation or reduces or prevents aggregation of the conjugate. In some of any embodiments, the pharmaceutical composition includes (1) a conjugate including an antibody linked to a phthalocyanine dye such as IR700 and (2) one or more stabilizing agents in an amount effective to reduce or prevent aggregation of the conjugate, wherein the one or more stabilizing agents include a surfactant, such as a non-ionic surfactant or a zwitterionic surfactant, and/or a protectant.

In some of any embodiments, the cell surface molecule is HER1 (also known as epidermal growth factor receptor, ErbB-1, and EGFR) and/or the antibody is cetuximab. In some of any embodiments, the antibody binds to HER1 (EGFR) or a portion thereof. In some of any embodiments, the antibody is cetuximab or a biosimilar, interchangeable, or biobetter thereof. In some of any embodiments, the antibody is cetuximab. In some of any embodiments, the conjugate is cetuximab-IR700.

Also provided herein are pharmaceutical compositions that include (1) a conjugate comprising a cetuximab or a biosimilar, interchangeable, or biobetter thereof linked to IR700 and (2) one or more stabilizing agents in an amount effective to reduce or prevent aggregation of the conjugate, wherein the one or more stabilizing agents comprises a surfactant and/or a protectant.

In some of any embodiments, the one or more stabilizing agents comprises a surfactant. In some of any embodiments, the one or more stabilizing agents include a surfactant, such as a non-ionic surfactant. In some of any embodiments, the non-ionic surfactant is a polysorbate, a lecithin, a polyethylene glycol (PEG), a polyoxyethylene glycol sorbitan alkyl ester, a polyethylene glycol octylphenyl ether, a block copolymer of polyethylene glycol and polypropylene glycol, a polyethylene glycol alkyl ether, or combinations thereof. In some of any embodiments, the non-ionic surfactant is selected from the group consisting of a polysorbate, a polyethylene glycol (PEG), a block copolymer of polyethylene glycol and polypropylene glycol or a polyethylene glycol octylphenyl ether, or a combination thereof.

In some of any embodiments, the surfactant is present at a percentage by weight to volume (w/v) of at least or at least about 0.01%. In some of any embodiments, the surfactant, e.g., non-ionic surfactant or a zwitterionic surfactant, is present at a percentage by volume (w/v) of at least or at least about 0.001%, 0.002%, 0.005%, 0.010%, 0.020%, 0.030%, 0.035%, 0.04%, 0.045%, 0.05%, 0.055%, 0.060%, 0.065%, 0.070%, 0.075%, 0.080%, 0.085%, 0.090%, 0.095%, or 0.100%. In some of any embodiments, the surfactant, e.g., non-ionic surfactant or a zwitterionic surfactant, is present at a percentage by weight to volume (w/v) of between 0.001% and 0.10%, between 0.001% and 0.075%, between 0.001% and 0.05%, between 0.001% and 0.01%, between 0.001% and 0.005%, 0.005% and 0.10%, between 0.005% and 0.075%, between 0.005% and 0.05%, between 0.005% and 0.01%, between 0.01% and 0.10%, between 0.01% and 0.075%, between 0.01% and 0.05%, between 0.05% and 0.1%, between 0.05% and 0.075% and between 0.075% and 0.10%, each inclusive. In some of any embodiments, the surfactant, e.g., non-ionic surfactant or a zwitterionic surfactant, is present at a percentage by weight to volume (w/v) of at least or at least about 0.02%, 0.03%, 0.04%, or 0.05%. In some of any embodiments, the surfactant, e.g., non-ionic surfactant or a zwitterionic surfactant, is present at a percentage by weight to volume (w/v) of between 0.02% and 0.06%, 0.02% and 0.05%, between 0.02% and 0.04%, between 0.02% and 0.03%, between 0.03% and 0.06%, between 0.03% and 0.05%, between 0.03% and 0.04%, between 0.04% and 0.06%, between 0.04% and 0.05%, between 0.05% and 0.06%, each inclusive.

In some of any embodiments, the wherein the non-ionic surfactant is a polysorbate. In some of any embodiments, the polyoxyethylene glycol sorbitan alkyl ester is a polysorbate, such as a polysorbate 20, polysorbate 40, polysorbate 60, polysorbate 80, or combinations thereof. In some of any embodiments, the polysorbate is polysorbate 20. In some of any embodiments, the polysorbate is polysorbate 80. In some of any embodiments, the polysorbate is present at a percentage by weight to volume (w/v) of at or about or at least or at least about 0.02%, 0.03%, 0.04%, or 0.05%. In some of any embodiments, the polysorbate is present at a percentage by weight to volume (w/v) of between 0.01% and 0.1%, between 0.1% and 0.5%, between 0.02% and 0.06%, between 0.02% and 0.05%, between 0.02% and 0.04%, between 0.02% and 0.03%, between 0.03% and 0.06%, between 0.03% and 0.05%, between 0.03% and 0.04%, between 0.04% and 0.06%, between 0.04% and 0.05%, between 0.05% and 0.06%, each inclusive.

In some of any embodiments, the non-ionic surfactant is polyethylene glycol (PEG). In some of any embodiments, the polyethylene glycol (PEG) is PEG 300, PEG 400, PEG 600, PEG 1000, PEG 1500, PEG 3000, PEG 3350, PEG 4000, PEG 6000, or PEG 8000. In some of any embodiments, the PEG is present at a percentage by weight to volume (w/v) of between 0.01% and 10%, between 0.025% and 7.5%, between 0.05% and 5%, between 0.05% and 2.5%, between 0.05% and 1%, between 0.05% and 0.75%, between 0.05% and 0.5%, between 0.05% and 0.25%, between 0.1% and 7.5%, between 0.1% and 5%, between 0.1% and 2.5%, between 0.1% and 1%, between 0.1% and 0.75%, between 0.1% and 0.5%, between 0.1% and 0.25%, between 0.5% and 7.5%, between 0.5% and 5%, between 0.5% and 2.5%, between 0.5% and 1%, between 0.5% and 0.75%, between 1% and 7.5%, between 1% and 5% and between 1% and 2.5%, each inclusive. In some of any embodiments, the PEG is present at a percentage by weight to volume (w/v) of at or about or at least or at least about 0.05%, 0.5% or 1%.

In some of any embodiments, the non-ionic surfactant is a polyethylene glycol octylphenyl ether. In some of any embodiments, the polyethylene glycol octylphenyl ether includes polyethylene glycol p-(1,1,3,3-tetramethylbutyl)-phenyl ether (Triton X-100®). In some of any embodiments, the Triton X-100® is present at a percentage by weight to volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive. In some of any embodiments, the Triton X-100 is present at a percentage by weight to volume (w/v) of at or about or at least or at least about 0.05%, 0.5% or 1%.

In some of any embodiments, the non-ionic surfactant is a block copolymer of polyethylene glycol and polypropylene glycol. In some of any embodiments, the block copolymer of polyethylene glycol and polypropylene glycol includes polyoxyethylene-polyoxypropylene block copolymer (Pluronic® F-68), poly (ethylene glycol)-block-poly (propylene glycol)-block-poly (ethylene glycol) (Pluronic® L-121), poloxamer 407 (Pluronic® F127), or combinations thereof. In some of any embodiments, the block copolymer of polyethylene glycol and polypropylene glycol is polyoxyethylene-polyoxypropylene block copolymer (Pluronic® F-68). In some of any embodiments, the Pluronic® F-68 is present at a percentage by weight to volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive. In some of any embodiments, the Pluronic® F-68 is present at a percentage by weight to volume (w/v) of at or about or at least or at least about 0.05%, 0.5% or 1%.

In some of any embodiments, the polyethylene glycol alkyl ether includes polyethylene glycol dodecyl ether (Brij® 35).

In some of any embodiments, the one or more stabilizing agents include a surfactant that is a zwitterionic surfactant. In some of any embodiments, the zwitterionic surfactant is 3-[(3-Cholamidopropyl) dimethylammonio]-1-propane-sulfonate (CHAPS). In some of any embodiments, the surfactant is a zwitterionic detergent, such as Zwittergent®. In some of any embodiments, the CHAPS is present at a percentage by weight to volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive. In some of any embodiments, the CHAPS is present at a percentage by weight to volume (w/v) of at or about or at least or at least about 0.05%, 0.5% or 1%.

In some of any embodiments, the one or more stabilizing agents include a protectant such as a tonicity agent. In some of any embodiments, the protectant is trehalose, sorbitol, sucrose, mannitol, xylitol or glycerol. In some embodiments, the protectant is trehalose. In some of any embodiments, the protectant is present at a percentage by weight to volume (w/v) of between 1% and 20%, between 1% and 5%, between 1% and 10%, and between 5% and 9%. In some of any embodiments, the protectant is present at a percentage by weight to volume (w/v) of at or at about or at least or at least about 1%, 2%, 3%, 4%, 5%, 6%, 7%, 8%, 9%, 10%, 11%, 12%, 13%, 14% or 15% by weight to volume (w/v).

In some of any embodiments, the one or more stabilizing agents include a protectant and a surfactant, e.g., a non-ionic surfactant or a zwitterionic surfactant.

In some of any embodiments, the conjugate is formulated as a concentrate and the protectant is present at a percentage by weight to volume (w/v) at or at about 20%, 25%, 30%, 35%, 40% or 50%.

Also provided are pharmaceutical compositions that include (1) a conjugate comprising an anti-HER1 (EGFR) antibody linked to IR700, (2) polysorbate 80, and (3) trehalose.

In some of any embodiments, the conjugate is formulated to a concentration that is from or from about 1.0 to or to about 5.0 mg/mL, from or from about 2.0 to or to about 10.0 mg/mL, from or from about 5.0 to or to about 50 mg/mL, or from or from about 20 to or to about 50 mg/mL. In some of any embodiments, the conjugate is formulated to a concentration of between 2 mg/mL and 10 mg/mL, inclusive. In some of any embodiments, the conjugate is formulated to a concentration of, of about, or of least at or about 5 mg/mL.

In some of any embodiments, the polysorbate 80 is present at between 0.01% and 0.1%, between 0.1% and 0.5%, or between 0.02% and 0.04% by weight to volume (w/v), each inclusive. In some of any embodiments, the polysorbate 80 is present at or at about 0.02% by weight to volume (w/v).

In some of any embodiments, the trehalose is present in amount between 1% and 20%, 3% and 12%, or 5% and 9% by weight to volume (w/v), each inclusive. In some of any embodiments, the trehalose is present in amount of between 5% and 9% by weight to volume (w/v), inclusive.

In some of any embodiments, the composition is formulated in a pharmaceutically acceptable buffer. In some of any embodiments, the pharmacologically acceptable buffer has a pH from or from about pH 6.0 to or to about pH 8.0, inclusive. In some of any embodiments, the pharmaceutically acceptable buffer has a pH of from or from about pH 6.8 to or to pH 7.4, inclusive. In some of any embodiments, the pharmaceutically acceptable buffer has a pH of or of about pH 7.1.

In some of any embodiments, the pharmaceutically acceptable buffer is sodium phosphate. In some of any embodiments, the sodium phosphate is present at a concentration of between 1 mM and 200 mM, between 1 mM and 50 mM, or between 5 mM and 25 mM, each inclusive.

Also provided herein are pharmaceutical compositions that include (1) between 2 mg/mL and 10 mg/mL of a conjugate comprising an anti-HER1 (EGFR) antibody linked to IR700, (2) between 0.1% and 0.5% polysorbate 80 by weight to volume (w/v), (3) between 5% and 9% trehalose by weight to volume (w/v), and (4) between 5 mM and 25 mM sodium phosphate, each inclusive. In some of any embodiments, the composition comprises polysorbate 80 at or at about 0.02% w/v. In some of any embodiments, the composition comprises trehalose at or at about 9% w/v.

In some of any embodiments, the antibody is cetuximab or a biosimilar, interchangeable, or biobetter thereof. In some of any embodiments, the antibody is cetuximab. In some of any embodiments, the conjugate comprises a cetuximab-IR700 conjugate.

Also provided herein are pharmaceutical compositions that include 5 mg/mL cetuximab-IR700 conjugate in a formulation that include 10 mM sodium phosphate, 0.02% (w/v) polysorbate 80 and 9% (w/v) trehalose at a pH of or of about pH 7.1.

In some of any embodiments, the composition is a liquid ready to use composition. In some of any embodiments, the composition is lyophilized or is formulated for lyophilization or is reconstituted from a lyophilized composition. In some of any embodiments, the composition is sterile. In some of any embodiments, the composition is stable at 2° C. to 8° C. for greater than 6 months, 12 months or 18 months.

In some of any embodiments, the conjugate is present in at least or at least about 70%, 80%, 85%, 90%, 95%, or 98% monomeric form. In some of any embodiments, the percentage of monomeric form is assessed by size-exclusion chromatography.

In some of any embodiments, aggregation of the conjugate is reduced by 1%, 5%, 10%, 20%, 30%, 40%, 50%, 60%, 70%, 80%, 90%, 95%, 99%, or more compared to aggregation in a composition including the conjugate but lacking the surfactant, e.g., non-ionic surfactant or zwitterionic surfactant, and/or the protectant. In some of any embodiments, the reduced aggregation is present after sheer stress and/or agitation; after exposure to a pH of less than or less than about pH 6.0; after 3 months at a temperature greater than or greater than about 25° C.; and/or after exposure for 1 week at a temperature greater than or greater than about 40° C., or combinations thereof.

In some of any embodiments, the reduced aggregation is characterized by percent recovery, the percentage of the conjugate in monomeric form, the percentage of the conjugate contained in a mean peak, potency of the composition, activity of the composition, purity or the composition, or combinations thereof.

In some of any embodiments, the recovery of the conjugate is greater than 80%, 85%, 90%, 91%, 92%, 93%, 94%, 95%, 96%, 97%, 98%, 99%, 99.5%, 99.9%, or 100% after sheer stress and/or agitation; after exposure to a pH less than or less than about pH 6.0; after 3 months at a temperature greater than or greater than about 25° C.; and/or after exposure for 1 week at a temperature greater than or greater than about 40° C., or a combination thereof. In some of any embodiments, the percentage of the conjugate in monomeric form in the composition is at least 70%, 80%, 85%, 90%, 91%, 92%, 93%, 94%, 95%, 96%, 97%, 98%, 99% after sheer stress and/or agitation; after exposure to a pH less than or less than about pH 6.0; after 3 months at a temperature greater than or greater than about 25° C.; and/or after exposure for 1 week at a temperature greater than or greater than about 40° C., or a combination thereof. In some of any embodiments, the percentage of the conjugate contained in a mean peak as determined by high performance liquid chromatography (HPLC) is greater than 70%, 80%, 85%, 90%, 91%, 92%, 93%, 94%, 95%, 96%, 97%, 98%, or 99% after sheer stress and/or agitation; after exposure to a pH less than or less than about pH 6.0; after 3 months at a temperature greater than or greater than about 25° C.; and/or after exposure for 1 week at a temperature greater than or greater than about 40° C., or a combination thereof. In some of any embodiments, the HPLC is size exclusion HPLC (SE-HPLC). In some of any embodiments, the composition retains greater than or greater than about 30%, 40%, 50%, 60%, 70%, 80%, 90%, 91%, 92%, 93%, 94%, 95%, 96%, 97%, 98%, 99%, 99.5%, 99.9% or 100% of its potency, activity or purity after sheer stress and/or agitation; after exposure to a pH less than or less than about pH 6.0; after 3 months at a temperature greater than or greater than about 25° C.; and/or after exposure for 1 week at a temperature greater than or greater than about 40° C., or a combination thereof.

In some of any embodiments, the shear stress and/or agitation is caused by shaking, freeze-thaw, transportation, drawing into a syringe, manufacturing procedures including, but not limited to, purification procedures and finish/fill procedures. In some of any embodiments, the shaking includes shaking on an orbital shaker. In some of any embodiments, the shaking is at a speed greater than 25 rpm, greater than 50 rpm, greater than 75 rpm, greater than 100 rpm, greater than 125 rpm, greater than 150 rpm, greater than 175 rpm, greater than 200 rpm, greater than 225 rpm, greater than 250 rpm, greater than 275 rpm, or greater than 300 rpm. In some of any embodiments, the shaking is carried out for a period of time is greater than 1 minute, greater than 5 minutes, greater than 10 minutes, greater than 15 minutes, greater than 20 minutes, greater than 25 minutes, greater than 30 minutes, greater than 45 minutes, greater than 60 minutes, greater than 90 minutes, greater than 120 minutes, greater than 150 minutes, greater than 180 minutes, greater than 210 minutes, greater than 240 minutes, greater than 270 minutes, greater than 300 minutes, greater than 330 minutes, greater than 360 minutes, greater than 390 minutes, greater than 420 minutes, greater than 450 minutes, greater than 480 minutes, greater than 510 minutes, greater than 540 minutes, greater than 570 minutes, or greater than 600 minutes.

In some of any embodiments, the exposure for more than or about 3 months is at a temperature greater than or greater than about 30° C., 35° C., 37° C., or 40° C. In some of any embodiments, the exposure for more than 1 week at a temperature greater than or greater than about 40° C. is for more than at or about 1 week, more than at or about 2 weeks or more than at or about 1 month.

In some of any embodiments, the phthalocyanine dye has a maximum absorption wavelength from or from about 600 nm to about 850 nm. In some of any embodiments, the phthalocyanine dye has a maximum absorption wavelength from or from about 650 nm to about 850 nm. In some of any embodiments, the phthalocyanine dye has a maximum absorption wavelength from or from about 680 nm to about 850 nm. In some of any embodiments, the phthalocyanine dye includes IR700.

In some of any embodiments, the molar ratio of dye to antibody is at least or at least about 1:1, at least or at least about 4:1 or is at least or at least about 10:1. In some of any embodiments, the molar ratio of dye to antibody is from or from about 1:1 to 10:1. In some of any embodiments, the conjugate is formulated to a concentration that is from or from about 1.0 to about 5.0 mg/mL.

In some of any embodiments, the composition is formulated in a pharmaceutically acceptable buffer. In some of any embodiments, the pharmaceutically acceptable buffer is sodium phosphate. In some of any embodiments, the pharmaceutically acceptable buffer is phosphate buffered saline. In some of any embodiments, the pharmacologically acceptable buffer has a pH from or from about pH 6.0 to about pH 8.0. In some of any embodiments, the pharmaceutically acceptable buffer has a pH of from or from about pH 6.8 to pH 7.4. In some of any embodiments, the pharmaceutically acceptable buffer has a pH of from or from about pH 7.1 to pH 7.3. In some of any embodiments, the pharmaceutically acceptable buffer has a pH of or of about pH 6.8, 6.9, 7.0, 7.1, 7.2, 7.3 or 7.4.

Also provided in some embodiments are containers containing any of the pharmaceutical compositions described herein. In some of any embodiments, the container is a vial, a tube, a syringe, a bag, a pouch or a box. In some of any embodiments, the container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some of any embodiments, the container protects from transmission of light such that the percentage of light transmission is less than 50%, less than 40%, less than 30%, less than 20%, less than 10% or less than 5%. In some of any embodiments, the container is green, blue, amber, translucent, opaque, or is covered by a material with light transmission of less than 50%, less than 40%, less than 30%, less than 20%, less than 10% or less than 5%.

Also provided in some embodiments are methods of treating a lesion in a subject that involves administering to the subject a therapeutically effective amount of any of the compositions provided herein; and after administering the conjugate, irradiating the lesion at a wavelength to induce phototoxic activity of the conjugate.

In some of any embodiments, irradiating the lesion is carried out at a wavelength of 500 nm to 900 nm, inclusive, at a dose of at least 1 J cm$^{-2}$ or 1 J/cm of fiber length. In some of any embodiments, irradiating the lesion is carried out at wavelength of 600 nm to 850 nm. In some of any embodiments, irradiating the lesion is carried out at a wavelength of 690±50 nm or at a wavelength of or about 690±20 nm. In some of any embodiments, the irradiating step is carried out at a wavelength of about 690 nm. In some of any embodiments, irradiating the lesion is carried out at a dose of from or from about 2 J cm$^{-2}$ to about 400 J cm$^{-2}$ or from or from about 2 J/cm fiber length to about 500 J/cm fiber length. In some of any embodiments, irradiating of the lesion is carried out at a dose of at least or at least about 2 J cm$^{-2}$, 5 J cm$^{-2}$, 10 J cm$^{-2}$, 25 J cm$^{-2}$, 50 J cm$^{-2}$, 75 J cm$^{-2}$, 100 J cm$^{-2}$, 150 J cm$^{-2}$, 200 J cm$^{-2}$, 300 J cm$^{-2}$, 400 J cm$^{-2}$, or 500 J cm$^{-2}$; or irradiating of the lesion is carried out at a dose of at least or at least about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length.

In some of any embodiments, the irradiating step is carried out at a dose of from or from about 25 J/cm$^2$ to about 100 J/cm$^2$. In some of any embodiments, the irradiating step is carried out with a frontal light diffuser at a dose of or of about 50 J/cm$^2$. In some of any embodiments, the irradiating step is carried out with a frontal light diffuser or by superficial illumination. In some of any embodiments, the irradiating step is carried out with a cylindrical light diffuser at a dose of from or from about 50 J/cm fiber length to about 150 J/cm fiber length. In some of any embodiments, the irradiating step is carried out with a cylindrical light diffuser at a dose of or of about 100 J/cm fiber length. In some of any embodiments, the irradiating step is carried out with a cylindrical light diffuser or by interstitial illumination.

In some of any embodiments, the lesion is fibrosis, premalignant dysplasia, carcinoma in situ, hyperplasia, neoplasm, a tumor, or a tumor that is associated with a cancer. In some of any embodiments, the tumor is a sarcoma or carcinoma. In some of any embodiments, the tumor is a carcinoma that is a squamous cell carcinoma, basal cell carcinoma or adenocarcinoma. In some of any embodiments, the tumor is a carcinoma that is a carcinoma of the bladder, pancreas, colon, ovary, lung, breast, stomach, prostate, cervix, esophagus or head and neck. In some of any embodiments, the cancer is a cancer located at the head and neck, breast, liver, colon, ovary, prostate, pancreas, brain, cervix, bone, skin, eye, bladder, stomach, esophagus, peritoneum, or lung.

In some of any of the methods provided herein, the conjugate is IR700-cetuximab. In some of any embodiments, the cancer is a cancer located at the head and neck, and the conjugate is IR700-cetuximab.

In some of any embodiments, irradiating of the lesion is carried out between or between about 30 minutes and about 96 hours after administering the conjugate. In some of any embodiments, the irradiating step is carried out between or between or between about 10 and about 40 hours after administering the conjugate. In some of any embodiments, the irradiating step is carried out between or between or between about 20 and about 28 hours after administering the conjugate. In some of any embodiments, the irradiating step is carried out at about 24 hours after administering the conjugate. In some of any embodiments, the irradiating step is carried out at about 24±4 hours after administering the conjugate.

In some of any embodiments, the conjugate is administered at a dose from or from about 50 mg/m$^2$ to about 5000 mg/m$^2$, from about 250 mg/m$^2$ to about 2500 mg/m$^2$, from about 750 mg/m$^2$ to about 1250 mg/m$^2$, from about 160 mg/m$^2$ to 640 mg/m$^2$, from about 160 mg/2 to 1000 mg/2, from about 500 mg/m$^2$ to about 1000 mg/m$^2$, from about 500 mg/m$^2$ to about 750 mg/m$^2$ or from about 100 mg/m$^2$ to about 1000 mg/m$^2$. In some of any embodiments, the conjugate is administered at a dose of about 500 mg/m$^2$, 550 mg/m$^2$, 600 mg/m$^2$, 620 mg/m$^2$, 640 mg/m$^2$, 660 mg/m$^2$, 680 mg/m$^2$, or 700 mg/m$^2$. In some of any embodiments, the conjugate is administered at a dose of or of about 160 mg/m$^2$, 320 mg/m$^2$, 640 mg/m$^2$, or 1280 mg/m$^2$. In some of any embodiments, the conjugate is administered at a dose of or of about 640 mg/m$^2$.

In some of any embodiments, the method further includes administering an additional therapeutic agent or anti-cancer treatment. In some of any embodiments, the anti-cancer treatment includes radiation therapy. In some of any embodiments, the additional therapeutic agent comprises an immune modulating agent. In some of any embodiments, the immune modulating agent is an immune checkpoint inhibitor.

Also provided herein are methods of treating a tumor or cancer in a subject that involves (a) intravenously administering to a subject having a tumor or cancer a composition comprising a cetuximab-IR700 conjugate in a formulation comprising 10 mM sodium phosphate, 0.02% (w/v) polysorbate 80 and 9% (w/v) trehalose at pH 7.1, wherein the conjugate is administered in an amount that is or is about 640 mg/m$^2$; and (b) after administering the conjugate, irradiating the lesion at about 24±4 hours at a wavelength of 690±20 nm at a dose of at least or about at least 50 J cm$^{-2}$ or 100 J/cm of fiber length, thereby treating the tumor or cancer in the subject.

Also provided herein are methods of treating a tumor or cancer in a subject that involves (a) intravenously administering to a subject having a head or neck cancer a composition comprising a cetuximab-IR700 conjugate in a formulation comprising 10 mM sodium phosphate, 0.02% (w/v) polysorbate 80 and 9% (w/v) trehalose at pH 7.1, wherein the conjugate is administered in an amount that is or is about 640 mg/m$^2$; and (b) after administering the conjugate, irradiating the lesion at about 24±4 hours at a wavelength of 690±20 nm at a dose of at least or about at least 50 J cm$^{-2}$ or 100 J/cm of fiber length, thereby treating the cancer in the subject.

In some of any embodiments of the provided methods, the composition comprises 5 mg/mL cetuximab-IR700 conjugate.

BRIEF DESCRIPTION OF THE DRAWINGS

FIGS. 6A-6C display HPLC-SEC of cetuximab-IR680 (FIG. 6A), cetuximab-IR700 (FIG. 6B) and cetuximab-IR800 (FIG. 6C), formulated in PBS or in trehalose and Polysorbate 80 formulation, after incubation at 40° C. or 5° C. for 1 month.

FIG. 7A-7C display HPLC-SEC results from PBS and Polysorbate 80 formulations for cetuximab-IR680 (FIG. 7A), cetuximab-IR700 (FIG. 7B), and cetuximab-IR800 (FIG. 7C) conjugates after agitation.

DETAILED DESCRIPTION

Figure 1A:
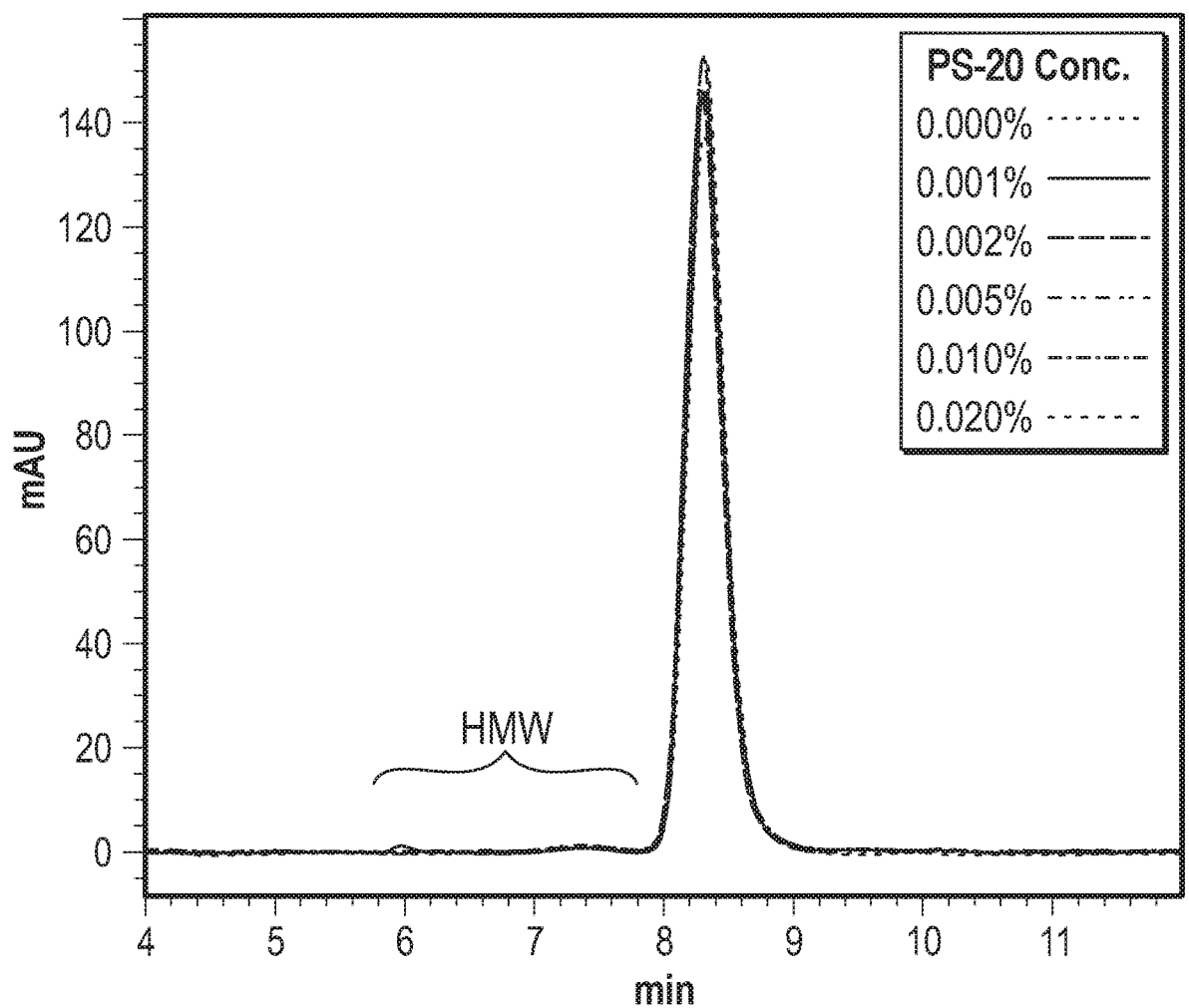
FIG. 1A displays size-exclusion high performance liquid chromatography (SE-HPLC) profiles for cetuximab in the presence or absence of various concentrations of polysorbate 20. HMW corresponds to high molecular weight peaks.

Provided herein are compositions containing stabilizing agents and phthalocyanine dye-antibody conjugates, such as an antibody-IR700 conjugate. In some embodiments, the stabilizing agents reduce or prevent aggregation or degradation, such as under certain conditions in which the antibody-IR700 conjugate, such as a cetuximab-IR700 conjugate or a conjugate containing a biosimilar, interchangeable, or biobetter of cetuximab and IR700, may be susceptible to aggregation or degradation. In some embodiments, the stabilizing agents include one or more surfactants, such as non-ionic surfactants or zwitterionic surfactants, and/or protectants. In some embodiments, the one or more stabilizing agent reduces aggregation that may occur following exposure to agitation, particular temperature, e.g., high temperature or thermal stress conditions, and/or pH. The provided compositions containing a dye-conjugate can be stable for greater than 3 months, and generally greater than 6 months or greater than 12 months, including a dye-conjugate that is stable under conditions of storage.

In some embodiments, the provided pharmaceutical compositions contain a phthalocyanine dye-antibody conjugate that can be used in photoimmunotherapy methods. In some embodiments, the provided pharmaceutical compositions comprising an antibody-IR700 conjugate allows stable storage, for example, under particular storage conditions, before using in photoimmunotherapy methods. Photoimmunotherapy is a molecular targeted therapy that utilizes a target-specific photosensitizer based on phthalocyanine dye, such as the IR700 phthalocyanine dye, conjugated to an antibody, such as an antibody targeting to a cell surface protein on tumor cells. For example, in some cases a phthalocyanine dye-conjugate used in photoimmunotherapy can include conjugation to a monoclonal antibody (mAb), such as Cetuximab, or a biosimilar, interchangeable, or biobetter thereof, targeting tumor-specific cell surface proteins, e.g., a tumor-specific cell surface receptor. In some embodiments, activation of the dye-conjugate by irradiation with absorbing light excites the photosensitizer and results in cell killing. In some cases, the use of light in the appropriate range leads to deeper tissue penetration resulting in successful eradication of tumors after only a single dose of external light irradiation.

Typically, PIT results in cell death primarily of those cells to which the phthalocyanine-dye conjugate, such as antibody-IR700 conjugate, binds after the cells are irradiated, while cells that do not express the cell surface protein recognized the antibody are not killed in significant numbers. Thus, because the therapy is targeted specifically to disease cells, such as tumor cells, its effects are highly selective to disease tissue compared to healthy tissue or cells. For example, although a targeted photosensitizer can distribute throughout the body, it is only active where intense light is applied, reducing the likelihood of off-target effects.

Generally, targeted phototoxicity appears to be primarily dependent on binding of the dye-conjugate to the cell membrane via the specific targeting molecule (e.g., antibody). For example, studies using an exemplary antibody-IR700 molecule indicate that the conjugate must be bound to the cellular membrane to be active, and that cell killing does not require intracellular localization (e.g., internalization) to be effective (see. e.g., U.S. Pat. No. 8,524,239 and U.S. published application No. US20140120119). Photo-activation of the conjugate-bound cells results in rapid cell death and necrosis.

Generally, phthalocyanine dyes, and in particular IR700, are extremely photostable dyes. For example, IR700 is reported to be 45 to 128 times more photostable than other near-infrared dyes and is free of aggregation (Peng et al. (2006) Proc. SPIE 6097, 60970E; see also www.licor.com/bio/products/reagents/irdye/700dx/photostability.html). Peng et al. reports that when IR700 is conjugated to an antibody, it exhibits virtually the same fluorescence excitation and absorption spectra as the non-conjugated dye, thereby indicating the conjugate retains its fluorescent properties. In some aspects, the photostability of IR700 can permit its use in applications in which the dye is exposed to continuous excitation with light for extended time periods and without the need to be protected from light. This is in contrast to other fluorophore dyes that are not photostable and cannot remain fluorescent when exposed to light for an extended period.

Conjugating the dye to an antibody, which is necessary for PIT activity, can reduce the stability of the dye, such that the conjugate (e.g., antibody-IR700 conjugate) can be more prone to aggregation, which can lead to a decreased activity (e.g., PIT activity). Exemplary causes of aggregation include shear stress, reactive oxygen species, pH, temperature (e.g., thermal stress), and light exposure. For example, it is found herein that shear stress, such as shaking, can cause monomeric antibodies to form higher molecular weight multimers and/or precipitate out of solution. In some aspects, thermal stress conditions, such as exposure to relatively high temperature, can also result in formation of higher molecular weight multimers and/or precipitation of the conjugates out of solution. Aggregation can reduce the potency, activity, or purity of a pharmaceutical composition.

This effect occurs even though the dye in the monomer retains its photostability and fluorescent properties. In some cases, particularly for therapeutic applications, this can reduce the activity and thereby limit the efficacy of the conjugate as a PIT agent. This result is not shown for other dye conjugates (e.g., IRDye 680 conjugates) where such dyes exhibit less photostability but are not prone to aggregate when conjugated to another molecule. Thus, it is found therein that conjugates of certain phthalocyanine dyes, such as IR700, used for PIT are particular sensitive to soluble and insoluble aggregate formation when exposed to certain conditions compared to conjugates of other dyes, including other 700 nm dyes. In some aspects, this is a problem because the fraction of monomer purity and pharmacological activity (e.g., PIT activity) are necessary for therapeutic use of the phthalocyanine dye conjugate (e.g., IR700 conjugate), since changes in purity or activity can lead to a significant impact on the light-activated killing activity and stability of the conjugate during storage.

These observations are based, in part, on visual analysis and HPLC-SEC analysis of dye conjugates prepared or exposed to different conditions. For example, the Examples provided herein demonstrate that aggregation of the bound dye portion of an antibody-dye conjugate can occur when the conjugate is exposed to shaking for several hours or to temperature stress (e.g., thermal stress). In some embodiments, the general instability of the dye conjugate is evident when the conjugate is formulated at acidic pH. For example, the dye conjugate can exhibit increased aggregation at pH less than 6.0. In some cases, the susceptibility of the dye conjugate to aggregation can minimize its use in PIT and/or reduce the activity or function of the conjugate for PIT.

The provided observations establish that, in some cases, compositions of phthalocyanine dye conjugates with one or more stabilizing agents that minimize aggregation and retain activity can overcome the problems described above and ensure consistency in product manufacturing, such as used in accord with good manufacturing production (GMP) methods. Examples of stabilizing agents include, but are not limited to, surfactants, such as non-ionic surfactants or zwitterionic surfactants and/or protectants. Thus, provided herein are formulations to reduce conjugate aggregation and to improve the integrity, purity, activity, or potency, of the dye conjugate, in particular, conjugates of IR700 to an antibody, such as cetuximab-IR700.

The section headings used herein are for organizational purposes only and are not to be construed as limiting the subject matter described.

I. PHARMACEUTICAL COMPOSITIONS AND ARTICLES OF MANUFACTURE

Provided herein are pharmaceutical compositions containing a phthalocyanine-dye antibody conjugate (e.g., antibody-IR700 conjugate) and one or more stabilizing agents. In some embodiments, the compositions can be used in methods of PIT as described herein. The phthalocyanine dye-antibody conjugate can be, for example, an IR700-antibody conjugate, such as cetuximab-IR700. Generally, the stabilizing agents are present in an amount effective to reduce or prevent aggregation of the conjugate. In some embodiments, the compositions contain an effective amount of the conjugate along with one or more stabilizing agents, such as surfactants, e.g., non-ionic surfactants or zwitterionic surfactants, and/or protectants.

A. Conjugates Containing a Phthalocyanine Dye and an Antibody

The pharmaceutical compositions provided herein contain a conjugate containing a photosensitizer, such as a phthalocyanine dye, for example IR700, and an antibody, such as an antibody that binds to a cell surface protein. In some embodiments, the antibody that is conjugated to the photosensitizer, the IR700 dye, permits the targeting of the conjugate to a cell surface molecule, e.g., a cell surface receptor, of cells involved in a disease or condition, such as a tumor or cancer, infection, inflammatory disease or condition, neuronal disease or condition or other disease or condition. In some embodiments, cell targeting increases the efficacy of PIT induced upon local irradiation of the subject, such as irradiation of a tumor in the subject, at a wavelength that is absorbed by the phthalocyanine dye.

The phthalocyanine dye conjugates contained in the compositions provided herein include a dye molecule (e.g., IRDye 700DX, also known as IR700) conjugated to an antibody via a linker group. In one aspect, the conjugate is of Formula I:

A-[(L)$_n$-D]$_p$  (I)

wherein:
  A is an antibody that can bind to cells or tissues;
  L is an independently selected linker for each p;
  n is 1 or 2;
  D is an independently selected hydrophilic phthalocyanine dye for each p; and
  p is independently 1, 2, 3, 4, 5 or greater than 5, such as up to 1000. For example, p can be 1 to 1000, such as generally 1 to 10 or 2 to 5.

Phthalocyanines are a group of photosensitizer compounds having the phthalocyanine ring system. Phthalocyanines are azaporphyrins that contain four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center is occupied by a metal ion (either a diamagnetic or a paramagnetic ion) that may, depending on the ion, carry one or two ligands. In addition, the ring periphery may be either unsubstituted or substituted. The synthesis and use of a wide variety of phthalocyanines in photodynamic therapy, including IR700, are described in International Publication WO 2005/099689 and U.S. Pat. No. 7,005,518.

In some embodiments, the phthalocyanine dye containing the reactive group is IR700 NHS ester, such as IRDye 700DX NHS ester (LiCor 929-70010, 929-70011). Thus, in some embodiments, the dye is a compound having the following formula:

Chemical Formula: $C_{74}H_{96}N_{12}Na_4O_{27}S_6Si_3$
Exact Mass: 1952.37
Molecular Weight: 1954.22
IRDye 700DX NHS Ester For purposes herein, the terms "IR700," and "IRDye 700DX" refer to the above formula when the dye is conjugated such as to an antibody, e.g., via a reactive group. Generally, IR700 has several favorable chemical properties. Amino-reactive IR700 is a relatively hydrophilic dye and can be covalently conjugated with an antibody using the NHS ester of IR700. Typically, IR700 also has more than 5-fold higher extinction coefficient ($2.1 \times 10^5$ M$^{-1}$ cm$^{-1}$ at the absorption maximum of 689 nm), than conventional photosensitizers such as the hematoporphyrin derivative Photofrin® ($1.2 \times 10^3$ M$^{-1}$ cm$^{-1}$ at 630 nm), meta-tetrahydroxyphenylchlorin; Foscan® ($2.2 \times 10^4$ M$^{-1}$ cm$^{-1}$ at 652 nm), and mono-L-aspartylchlorin e6; NPe6/Laserphyrin® ($4.0 \times 10^4$ M$^{-1}$ cm$^{-1}$ at 654 nm).

The phthalocyanine dyes described herein can be made with commercially available starting material. The core structure is synthesized by condensation of two or more different diiminoisoindolines. Synthetic strategies using different dinitriles or diiminoisoindolines can lead to various degrees of substitution of the phthalocyanine and/or distribution of regioisomers. Exemplary synthetic schemes for generating the dyes are described in U.S. Pat. No. 7,005,518. Exemplary synthetic schemes for preparing and characterizing conjugates to dyes such as IR700 are described in WO 2017/031363.

In some embodiments, a dual-label conjugate is provided in which an antibody or antigen-binding antibody fragment is conjugated to IR700 and also is conjugated to another second fluorescent dye. In some embodiments, the dual-label conjugate can be used to both monitor PIT therapy as described above and also to treat with PIT by activating the IR700 dye. In some embodiments, the second dye is selected to minimize energy transfer between it and the IR700, for example, second dye is selected to avoid or minimize overlapping emission and absorption spectra with IR700.

In some embodiments, the phthalocyanine dye is conjugated to an antibody via a reactive group of the dye

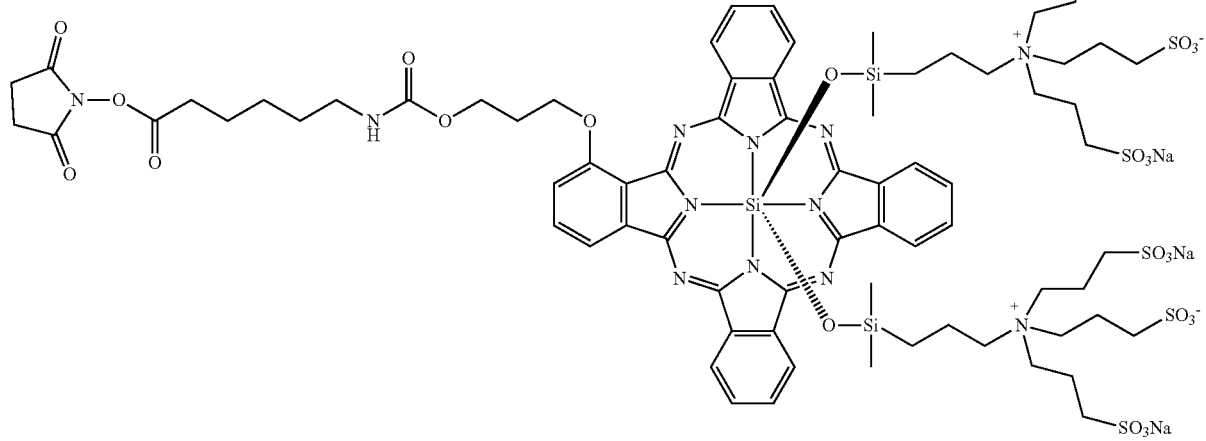

molecule. In some embodiments, the antibody contained in the compositions described herein is one that is able to target the conjugate to a cell or pathogen, for example, by binding to a cell surface molecule (e.g., cell surface receptor) on the cell or pathogen. In some embodiments, the antibody can selectively bind to a desired cell type, cells with a particular phenotype, or cells displaying one or more cell surface markers or antigens. In some cases, the antibody binds to a cell that is a cancer cell, a tumor cell, an inflammatory cell, an immune cell, a neuron, a stem cell, a proliferating cell, or a cell in a hyperplasia. In some cases, the antibody binds to a pathogen or a pathogen infected cell. In some embodiments, the cell is an inflammatory cell, such a leukocyte, for example, a neutrophil, an eosinophil, a basophil, a lymphocyte, or a monocyte. In some embodiments, the cell is an immune cell, such as a T cell, a B cell, a Natural Killer (NK) cell, a dendritic cell, a macrophage, or a neutrophil. In some embodiments, the cell is a neuron that is a peripheral nervous system neuron or a central nervous system neuron, such as a nociceptor, for example, thermal nociceptors, mechanical nociceptors, chemical nociceptors, or polymodal nociceptors. In some cases, the antibody binds to a pathogen or a pathogenic cell, such as a virus, bacterium, fungus, biofilm or other prokaryotic cell system.

In some embodiments, the antibody binds a cell surface target molecule on a surface of a cell or a pathogen. In some embodiments, the cell is a stem cell, a proliferating cell, a cell in a hyperplasia, or a pathogen infected cell. In some embodiments, the cell is a cancer cell, a tumor cell, a cell present in a tumor microenvironment, an inflammatory cell, an immune cell, or a neuron. In some embodiments, the cell is present in the microenvironment of a lesion associated with a disease or condition. In some embodiments, the lesion is a tumor and the cell is a cancer cell or a tumor cell. In some embodiments, the cell is a cancer stem cell or a circulating tumor cell.

In some embodiments, the antibody of the phthalocyanine dye conjugate contained in the compositions described herein binds to a protein on the surface of a cell or cells present in a microenvironment of a lesion that is associated with or present as a result of a disease or condition and/or a cell associated with a disease, disorder or a condition. For example, in some embodiments, the conjugate binds to a protein on the surface of a cell or cells present in a tumor microenvironment associated with or present in a tumor. In some embodiments, the conjugate binds to a protein present in the extracellular matrix in the microenvironment of the tumor.

As used herein, a "cell present in the microenvironment of a lesion" refers to any cell present in the cellular environment associated with a lesion, a disease or a disorder, such as any cell present in or immediately adjacent to a tumor, such as cells present in a tumor microenvironment, or the extracellular matrix in the tumor microenvironment.

As used herein, a "cell present in a tumor microenvironment" refers to any cell present in the cellular environment in which the tumor exists, such as any cell present in or immediately adjacent to the tumor, including the proliferating tumor cells (e.g., cancer cells), the tumor stroma, blood vessels, infiltrating inflammatory cells (e.g., immune cells) and a variety of associated tissue cells (e.g., fibroblasts). Thus, it is understood that reference to the tumor refers not only to the tumor cells, which can include malignant or cancer cells, but also to other cells present in the tumor microenvironment that regulate the growth of the tumor, including immune cells. In some cases, immune cells present in a tumor microenvironment can include T lymphocytes, including regulatory T lymphocytes (Treg), dendritic cells, natural killer (NK) cells, B cells, macrophages and other immune cells (Whiteside (2008) Oncogene, 27:5904-5912). It is recognized that, in some aspects, many non-cancerous cells present in and around the tumor can regulate the proliferation, angiogenesis, invasion, and/or metastasis of tumor cells, thereby promoting the growth of the tumor. Thus, in some cases, targeting such non-cancerous cells, such as immune cells (e.g., T cells, such as regulatory T cells), present in a tumor can be an effective therapy for killing a tumor by PIT.

Generally, cancerous cells contain tumor-specific antigens that should be recognized by the immune system. Typically, in an active immune system, immune cells, such as cytotoxic T cells, attack and eradicate these cancerous cells. Under normal physiological conditions, the T cell-mediated immune response is initiated by antigen recognition by the T cell receptor (TCR) and is regulated by a balance of co-stimulatory and inhibitory signals (e.g., immune checkpoint proteins). In particular, CD4+ and CD8+ T cells expressing a TCR can become activated upon recognition of antigenic peptides presented on antigen-presenting cells on major histocompatibility complex (MHC) class I or class II molecules, respectively. In some aspects, activated CD8+ cells, or cytotoxic T cells, can kill tumor cells expressing the antigen, which can be helped by the presence of CD4+ T cells.

In the case of tumors, however, the tumor microenvironment has mechanisms to suppress the immune system, thereby evading immune recognition and preventing or reducing killing of tumor cells. For example, in some cases, immune checkpoint proteins can be dysregulated in tumors, thereby resulting in a suppression of the immune response in the tumor microenvironment as a mechanism of evading the immune system. In some cases, tumor-infiltrating lymphocytes can include Tregs (e.g., $CD4^+CD25^+$ T cells), which are cells that are capable of suppressing proliferation of other T cells in the microenvironment (Whiteside, TL (2008) Oncogene, 27:5904-5912). In some cases, other mechanisms can act to inhibit access of immune cells to tumor antigens, thereby also contributing to the tumors ability to evade the immune system.

In some embodiments, the antibody is a molecule that binds to a cell surface protein on a tumor or cancer cell. In some embodiments, the antibody binds to a cell surface protein on the surface of a T lymphocyte, such as a Treg, a dendritic cell, a natural killer (NK) cell, a B cell, a macrophage or other immune cell that is present in a tumor microenvironment. For example, the tumor or cancer cell can be one associated with a cancer located at the head and neck, breast, liver, colon, ovary, prostate, pancreas, brain, cervix, bone, skin, eye, bladder, stomach, esophagus, peritoneum, or lung. In some embodiments, the antibody binds a cell is a cancer stem cell or a circulating tumor cell.

In some embodiments, the antibody contained in the compositions described herein can selectively bind to a desired cell type, cells with a particular phenotype, or cells displaying one or more cell surface markers or antigens. In some embodiments, the antibody is a tumor targeting molecule. In some embodiments, the antibody can bind to tumor or cancer cells. In some embodiments, the antibody targets or binds to a marker or antigen on a cell surface, for example, a cell surface of a tumor cell.

In some embodiments, the antibody contained in the compositions described herein targets or binds to an antigen, such as any structural substance that serves as a target capable of being bound by the molecule. In some embodiments, the antigen is or is comprised as part of a cell surface molecule, such as a protein, e.g., a receptor, that is expressed on a cell surface. In some embodiments, for example, the antigen is or is comprised as part of a molecule expressed on the surface of a cell associated or a cell present in a tumor, including any cell present in the tumor microenvironment. Examples of cell surface molecules to which an antibody can bind, include, but are not limited to, an antigen, peptides, lipids, polysaccharides, carbohydrate, or nucleic acids containing antigenic determinants, such as those recognized by an immune cell. In some examples, an antigen includes a tumor-specific peptide (such as one found on the surface of a cancer cell) or immunogenic fragment thereof.

In some embodiments, the compositions described herein include an antibody or antibody fragment that specifically binds to an antigen, such as a cell surface molecule on a tumor cell. Included among such antibodies are antibodies or antigen-binding antibody fragments capable of binding to a cell surface molecule, such as a cell surface protein, e.g., cell surface receptor, described herein. In some cases, the antibody can bind to an antigen of a protein expressed on a cell in a tumor, including a tumor-specific protein (e.g., tumor-specific antigen).

An "antibody" as used herein is a polypeptide ligand comprising at least a light chain or heavy chain immunoglobulin variable region that specifically recognizes and binds an epitope of an antigen, such as a tumor-specific protein. Generally, antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

An "antibody" as used herein includes intact immunoglobulins and fragments of antibodies that exhibit antigen-binding, such as Fab fragments, Fab' fragments, F(ab)'$_2$ fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies, for example, humanized murine antibodies, and heteroconjugate antibodies, such as bispecific antibodies. See also, *Pierce Catalog and Handbook,* 1994-1995 (Pierce Chemical Co., Rockford, Ill.); Kuby, J. *Immunology,* 3$^{rd}$ Ed., W. H. Freeman & Co., New York, 1997

Typically, a naturally occurring immunoglobulin has heavy (H) chains and light (L) chains interconnected by disulfide bonds. There are two types of light chain, lambda (2) and kappa (κ). There are five main heavy chain classes, or isotypes, which determine the functional activity of an antibody molecule: IgM, IgD, IgG, IgA, and IgE.

Each heavy and light chain contains a constant region and a variable region, also known as "domains." In combination, the heavy and the light chain variable regions generally specifically bind the antigen. Light and heavy chain variable regions may contain a "framework" region interrupted by three hypervariable regions, also called "complementarity-determining regions" or "CDRs." The extents of the framework region and CDRs have been defined (see, Kabat et al., *Sequences of Proteins of Immunological Interest,* U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are typically responsible for binding to an epitope of an antigen. The CDRs of each chain are typically referred to as CDR1, CDR2, and CDR3, numbered sequentially starting from the N-terminus, and are also generally identified by the chain in which the particular CDR is located. Thus, a $V_H$CDR3 is located in the variable domain of the heavy chain of the antibody in which it is found, whereas a $V_L$CDR1 is the CDR1 from the variable domain of the light chain of the antibody in which it is found. Antibodies with different specificities, such as different combining sites for different antigens, have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

Among the provided antibodies contained in the compositions described herein are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. Other antibody fragments or multispecific antibodies formed from antibody fragments include a multivalent scFv, a bispecific scFv or an scFv-$C_H$3 dimer. Antibody fragments can be made by various techniques, including but not limited to proteolytic digestion of an intact antibody as well as production by recombinant host cells.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs, which generally confer antigen binding, from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In some embodiments, the CDRs are from the donor immunoglobulin in a humanized immunoglobulin. Constant regions need not be present, but if they are, they may be substantially identical to human immunoglobulin constant regions, such as at least about 85-90%, such as about 95% or more identical. Hence, parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and CDRs from a human immunoglobulin. In some embodiments, the framework and the CDRs are from the same originating human heavy and/or light chain amino acid sequence. However, frameworks from one human antibody can be engineered to include CDRs from a different human antibody. Parts of a human immunoglobulin may be substantially identical to corresponding parts of natural human immunoglobulin sequences.

"Specifically binds" refers to the ability of a molecule, such as an antibody or antigen-binding fragment, to specifically bind an antigen, such as a tumor-specific antigen, relative to binding to unrelated proteins, such as non-tumor proteins, for example β-actin. In some embodiments, a molecule, such as an antibody or fragment, including a molecule, such as an antibody or fragment, attached to a phthalocyanine dye molecule, specifically binds to a target, such as a cell surface protein, with a binding constant that is at least $10^3$ $M^{-1}$ greater, $10^4$ $M^{-1}$ greater or $10^5$ $M^{-1}$ greater than a binding constant for other molecules in a sample or subject. In some embodiments, a molecule, such as an antibody or fragments thereof, has an equilibrium association constant ($K_A$) of greater than or equal to at or about $10^6$ $M^{-1}$, greater than or equal to at or about $10^7$ $M^{-1}$, greater than or equal to at or about $10^8$ $M^{-1}$, or greater than or equal to at or about $10^9$ $M^{-1}$, $10^{10}$ $M^{-1}$, $10^{11}$ $M^{-1}$ or $10^{12}$ $M^{-1}$. Antibodies also can be characterized by an equilibrium dissociation constant ($K_D$) of at or about or less than at or about $10^{-6}$ M, $10^{-7}$ M, $10^{-8}$ M, $10^{-10}$ M, $10^{-11}$ M or $10^{-12}$ M or lower. In some embodiments, an equilibrium dissociation constant ($K_D$) can be 1 nM or less. Affinity constants, such as $K_D$ or $K_A$, can be estimated empirically or affinities can be determined comparatively, e.g., by comparing the affinity of one antibody and another antibody for a particular antigen. For example, such affinities can be readily determined using techniques known in the art, such as, for example, by competitive ELISA (enzyme-linked immunosorbent assay) or using a surface-plasmon resonance device, such as the Biacore T100 (available from Biacore, Inc., Piscataway, N.J), a radioimmunoassay using radiolabeled target antigen, or by another method known to the skilled artisan.

In some embodiments, the phthalocyanine dye (e.g., IR700) is conjugated to an antibody or an antigen-binding antibody fragment. For example, in some aspects, the phthalocyanine dye-antibody conjugate is an IR700-antibody conjugate.

In some embodiments, the antibody is selected from among cetuximab, panitumumab, zalutumumab, nimotuzumab, trastuzumab, Ado-trastuzumab emtansine, Tositomomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, BMS-935559, MPDL3280A, Pidilizumab (CT-011), AMP-224, MSB001078C, and MEDI4736, or is an antigen-binding fragment thereof.

In some embodiments, the cell surface molecule is HER1 (also known as epidermal growth factor receptor, ErbB-1, and EGFR). In some embodiments, the antibody in the conjugate is cetuximab, or a biosimilar, an interchangeable or a biobetter of cetuximab. In some embodiments, the antibody in the conjugate is a copy biological or a biogeneric of cetuximab. In some embodiments, the antibody in the conjugate is Erbitux®. In some embodiments, the conjugate is cetuximab-IR700, or a conjugate of a biosimilar, interchangeable or biobetter of cetuximab and IR700. In some embodiments, the antibody in the conjugate is an antigen-binding fragment of cetuximab, or a biosimilar, interchangeable or biobetter of cetuximab.

In some embodiments, the conjugate contained in the compositions described herein contains a number of dye residues per antibody molecule that is from or from about 1 to or to about 1000, such as from or from about 1 to or to about 100, from or from about 1 to or to about 50, from or from about 1 to or to about 25, from or from about 1 to or to about 10, from or from about 1 to or to about 5. In some embodiments, the ratio of dye molecules to antibody is or is about 2:1, 3:1, 4:1, 5:1, 10:1, 15:1, 20:1, 25:1, 50:1, 75:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1 or 1000:1, or is between or between about any two of such values. In some embodiments, the antibody may contain up to 2, 3, 4, 5, 6, 7, 8, 9, 10, 15, 20, 50, 75, 100, 150, 200, 250, 300, 350, 400, 450, 500, 550, 600, 650, 700, 750, 800, 850, 900, 950, or 1000 dye molecules. In some embodiments, the antibody molecule may contain more than 1000 dye molecules or less than 10 dye molecules. In some embodiments, the number of dye molecule per antibody can be from or from about 2 to or to about 5, such as from or from about 2 to or to about 4, for example about 3 or 3.

In some embodiments, the pharmaceutical compositions provided herein, which include a phthalocyanine dye-antibody conjugate, such as an IR700-antibody conjugate, are produced under light-protected conditions. In some embodiments, antibody is conjugated to a phthalocyanine dye under conditions to produce or generate the conjugate, and formulating, purifying and/or isolating the conjugate to produce a composition containing the drug substance, where one or more of the steps, such as in some cases all of the steps, are performed with minimal exposure of the dye or the conjugate containing the dye to environmental light.

B. Compositions, Formulations and Dosage Forms

In particular embodiments, a conjugate provided herein, e.g., a conjugate containing a phthalocyanine dye and an antibody (e.g., cetuximab-IR700), is formulated in a pharmaceutical composition. In some aspects, the pharmaceutical compositions provided herein contain one or more stabilizing agents, such as those that reduce or are capable of reducing conjugate aggregation and those that may improve the integrity, purity, activity, or potency, of the dye conjugate, e.g., conjugates of IR700 to an antibody, such as cetuximab-IR700. In particular embodiments, the one or more stabilizing agents are or include a surfactant, such as a non-ionic surfactant or a zwitterionic surfactant. In some embodiments, the one or more stabilizing agents are or include a protectant.

In some embodiments, the provided compositions contain one or more stabilizing agent that is a surfactant. In some embodiments, the provided compositions contain one or more stabilizing agent that is a non-ionic surfactant. In some embodiments, the non-ionic surfactant comprises a polysorbate, a lecithin, a polyethylene glycol (PEG), a polyethylene glycol alkyl ether, a polyethylene glycol octylphenyl ether, a polyoxyethylene glycol sorbitan alkyl ester, a block copolymer of polyethylene glycol and polypropylene glycol, or a combination thereof. In some embodiments, the non-ionic surfactant is selected from among a polysorbate, a polyethylene glycol (PEG), a block copolymer of polyethylene glycol and polypropylene glycol or a polyethylene glycol octylphenyl ether, or a combination thereof. Non-limiting examples of non-ionic surfactants for use in the compositions provided herein include polyethylene glycol p-(1,1,3,3-tetramethylbutyl)-phenyl ether (Triton X-100®), a polyethylene glycol (PEG), such as PEG 8000, polyoxyethylene-polyoxypropylene block copolymer (Pluronic® F-68), poly (ethylene glycol)-block-poly (propylene glycol)-block-poly (ethylene glycol) (Pluronic® L-121), poloxamer 407 (Pluronic® F127), and/or polyethylene glycol dodecyl ether (Brij® 35).

In particular embodiments, the pharmaceutical composition contains a polysorbate. In particular embodiments, the non-ionic surfactant is a polysorbate. In some embodiments, the polysorbate comprises polysorbate 20, polysorbate 40, polysorbate 60, and/or polysorbate 80. In some embodiments, the polysorbate comprises polysorbate 20. In some embodiments, the polysorbate comprises polysorbate 80. In certain embodiments, the pharmaceutical composition contains polysorbate 20 (PS-20). In particular embodiments, the pharmaceutical composition contains polysorbate 80 (PS-80).

In some embodiments, the pharmaceutical composition contains a polyethylene glycol (PEG). In particular embodiments, the non-ionic surfactant is a PEG. In some embodiments, the polyethylene glycol (PEG) is PEG 300, PEG 400, PEG 600, PEG 1000, PEG 1500, PEG 3000, PEG 3350, PEG 4000, PEG 6000, or PEG 8000.

In some embodiments, the pharmaceutical composition contains a block copolymer of polyethylene glycol and polypropylene glycol. In particular embodiments, the non-ionic surfactant is a block copolymer of polyethylene glycol and polypropylene glycol. In some embodiments, the block copolymer of polyethylene glycol and polypropylene glycol is selected from polyoxyethylene-polyoxypropylene block copolymer (Pluronic® F-68), poly (ethylene glycol)-block-poly (propylene glycol)-block-poly (ethylene glycol) (Pluronic®) L-121), poloxamer 407 (Pluronic® F127), or combinations thereof. In some embodiments, the block copolymer of polyethylene glycol and polypropylene glycol is Pluronic® F-68.

In some embodiments, the pharmaceutical composition contains polyethylene glycol octylphenyl ether. In particular embodiments, the non-ionic surfactant is a polyethylene glycol octylphenyl ether. In some embodiments, the polyethylene glycol octylphenyl ether is Triton X-100®.

In some embodiments, the one or more stabilizing agents include a zwitterionic surfactant. In some embodiments, the pharmaceutical composition contains a zwitterionic surfactant such as 3-[(3-Cholamidopropyl) dimethylammonio]-1-propanesulfonate (CHAPS). In some embodiments, the surfactant is a zwitterionic detergent, such as Zwittergent®.

In some embodiments, the surfactant, such as the non-ionic surfactant or the zwitterionic surfactant, is present at a percentage by volume (w/v) of at least or at least about 0.001%, 0.002%, 0.005%, 0.010%, 0.020%, 0.030%, 0.035%, 0.04%, 0.045%, 0.05%, 0.055%, 0.060%, 0.065%, 0.070%, 0.075%, 0.080%, 0.085%, 0.090%, 0.095%, or 0.100%. In some embodiments, the non-ionic surfactant is present at a percentage by volume (w/v) of between 0.001% and 0.10%, between 0.001% and 0.075%, between 0.001% and 0.05%, between 0.001% and 0.01%, between 0.001% and 0.005%, between 0.005% and 0.10%, between 0.005% and 0.075%, between 0.005% and 0.05%, between 0.005% and 0.01%, between 0.01% and 0.10%, between 0.01% and 0.075%, between 0.01% and 0.05%, between 0.05% and 0.1%, between 0.05% and 0.075% and between 0.075% and 0.10%, each inclusive. In some embodiments, the surfactant, such as the non-ionic surfactant or the zwitterionic surfactant, is present at a percentage by weight to volume (w/v) of between 0.01% and 10%, between 0.025% and 7.5%, between 0.05% and 5%, between 0.05% and 2.5%, between 0.05% and 1%, between 0.05% and 0.75%, between 0.05% and 0.5%, between 0.05% and 0.25%, between 0.1% and 7.5%, between 0.1% and 5%, between 0.1% and 2.5%, between 0.1% and 1%, between 0.1% and 0.75%, between 0.1% and 0.5%, between 0.1% and 0.25%, between 0.5% and 7.5%, between 0.5% and 5%, between 0.5% and 2.5%, between 0.5% and 1%, between 0.5% and 0.75%, between 1% and 7.5%, between 1% and 5% and between 1% and 2.5%, each inclusive. In some embodiments, the surfactant, such as the non-ionic surfactant or the zwitterionic surfactant, is present at a percentage by weight to volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive. In some embodiments, the surfactant, such as the non-ionic surfactant or the zwitterionic surfactant, is present in the composition at a percentage by volume (w/v) of at least or at least about 0.01%, 0.02%, 0.5%, 0.10%, 0.20%, 0.30%, 0.4%, 0.5%, 0.60%, 0.70%, 0.80%, 0.90%, or about 1%, 2%, 3%, 4%, 5%, 6%, 7%, 8%, 9%, or 10%. In some embodiments, the surfactant, such as the non-ionic surfactant or the zwitterionic surfactant, is present at a percentage by weight to volume (w/v) of between 0.01% and 10%, between 0.01% and 15%.

In some embodiments, the surfactant, such as the non-ionic surfactant or the zwitterionic surfactant, is present at a percentage by volume (w/v) of at least or at least about 0.02%, 0.03%, 0.04%, or 0.05%. In some embodiments, the surfactant, such as the non-ionic surfactant or the zwitterionic surfactant, is present at a concentration of a percentage by volume (w/v) of between 0.02% and 0.06%, between 0.02% and 0.05%, between 0.02% and 0.04%, between 0.02% and 0.03%, between 0.03% and 0.06%, between 0.03% and 0.05%, between 0.03% and 0.04%, between 0.04% and 0.06%, between 0.04% and 0.05%, between 0.05% and 0.06%, each inclusive.

In some embodiments a stock solution is created containing the formulation and/or formulation with the antibody-conjugate. In some embodiments, the stock solution contains between at or about 0.01% and at or about 30% surfactant, at or about 0.01% and at or about 20% surfactant, or at or about 0.01% and at or about 15% surfactant. In some embodiments, the stock solution contains the surfactant, e.g., non-ionic surfactant or zwitterionic surfactant, for up to at or about 30%, 25%, 15%, 10%, or 5% weight to volume (w/v), or within a range defined by any of the foregoing.

In particular embodiments, the pharmaceutical composition contains a polysorbate, e.g., polysorbate 20 or polysorbate 80, that is present in the composition at a percentage by volume (w/v) of at least or at least about 0.001%, 0.002%, 0.005%, 0.010%, 0.020%, 0.030%, 0.035%, 0.04%, 0.045%, 0.05%, 0.055%, 0.060%, 0.065%, 0.070%, 0.075%, 0.080%, 0.085%, 0.090%, 0.095%, or 0.100%. In various embodiments, the polysorbate, e.g., polysorbate 20 or polysorbate 80, is present at a percentage by weight to volume (w/v) of between 0.001% and 0.10%, between 0.001% and 0.075%, between 0.001% and 0.05%, between 0.001% and 0.01%, between 0.001% and 0.005%, between 0.005% and 0.10%, between 0.005% and 0.075%, between 0.005% and 0.05%, between 0.005% and 0.01%, between 0.01% and 0.10%, between 0.01% and 0.075%, between 0.01% and 0.05%, between 0.05% and 0.1%, between 0.05% and 0.075% and between 0.075% and 0.10%, each inclusive. In particular embodiments, the polysorbate, e.g., polysorbate 20 or polysorbate 80, is present at a percentage by weight to volume (w/v) of at least or at least about 0.02%, 0.03%, 0.04%, or 0.05%. In some embodiments, the polysorbate, e.g., polysorbate 20 or polysorbate 80, is present at a percentage by weight to volume (w/v) of between 0.02% and 0.06%, between 0.02% and 0.05%, between 0.02% and 0.04%, between 0.02% and 0.03%, between 0.03% and 0.06%, between 0.03% and 0.05%, between 0.03% and 0.04%, between 0.04% and 0.06%, between 0.04% and 0.05%, between 0.05% and 0.06%, each inclusive. In some embodiments, the polysorbate, e.g., polysorbate 20 or polysorbate 80, is present at a percentage by weight to volume (w/v) of at or about or at least or at least about 0.05%, 0.5% or 1%. In some embodiments, the composition comprises polysorbate 80 at or at about 0.02% w/v.

In particular embodiments, the pharmaceutical composition contains a polyethylene glycol (PEG), e.g., PEG 300, PEG 400, PEG 600, PEG 1000, PEG 1500, PEG 3000, PEG 8000, that is present in the composition at a percentage by volume (w/v) of at least or at least about 0.01%, 0.02%, 0.5%, 0.10%, 0.20%, 0.30%, 0.4%, 0.5%, 0.60%, 0.70%, 0.80%, 0.90%, or about 1%, 2%, 3%, 4%, 5%, 6%, 7%, 8%, 9%, or 10%. In various embodiments, the PEG is present at a percentage by weight to volume (w/v) of between 0.01% and 10%, between 0.01% and 15%. In particular embodiments, the pharmaceutical composition contains a polyethylene glycol (PEG), e.g., PEG 300, PEG 400, PEG 600, PEG 1000, PEG 1500, PEG 3000, PEG 8000, that is present in the composition at a percentage by volume (w/v) of between 0.01% and 10%, between 0.025% and 7.5%, between 0.05% and 5%, between 0.05% and 2.5%, between 0.05% and 1%, between 0.05% and 0.75%, between 0.05% and 0.5%, between 0.05% and 0.25%, between 0.1% and 7.5%, between 0.1% and 5%, between 0.1% and 2.5%, between 0.1% and 1%, between 0.1% and 0.75%, between 0.1% and 0.5%, between 0.1% and 0.25%, between 0.5% and 7.5%, between 0.5% and 5%, between 0.5% and 2.5%, between 0.5% and 1%, between 0.5% and 0.75%, between 1% and 7.5%, between 1% and 5% and between 1% and 2.5%, each inclusive. In some embodiments, the PEG, e.g., PEG 8000, is present at a percentage by weight to volume (w/v) of at or about or at least or at least about 0.05%, 0.5% or 1%. In some embodiments, the composition comprises PEG 8000 at or at about 0.02% w/v.

In particular embodiments, the pharmaceutical composition contains a block copolymer of polyethylene glycol and polypropylene glycol, e.g., polyoxyethylene-polyoxypropylene block copolymer (Pluronic® F-68), that is present in the composition at a percentage by volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive. In some embodiments, the block copolymer of polyethylene glycol and polypropylene glycol, e.g., Pluronic® F-68, is present at a percentage by weight to volume (w/v) of at or about or at least or at least about 0.05%, 0.5% or 1%. In some embodiments, the composition comprises Pluronic® F-68 at or at about 0.02% w/v.

In particular embodiments, the pharmaceutical composition contains a polyethylene glycol octylphenyl ether, e.g., polyethylene glycol octylphenyl ether is polyethylene glycol p-(1,1,3,3-tetramethylbutyl)-phenyl ether (Triton X-100®), that is present in the composition at a percentage by volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive. In some embodiments, the polyethylene glycol octylphenyl ether, e.g., Triton X-100®, is present at a percentage by weight to volume (w/v) of at or about or at least or at least about 0.05%, 0.5% or 1%. In some embodiments, the composition comprises Triton X-100® at or at about 0.02% w/v.

In particular embodiments, the pharmaceutical composition contains a zwitterionic surfactant, e.g., 3-[(3-Cholamidopropyl) dimethylammonio]-1-propanesulfonate (CHAPS), that is present in the composition at a percentage by volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive. In some embodiments, the zwitterionic surfactant, e.g., CHAPS, is present at a percentage by weight to volume (w/v) of at or about or at least or at least about 0.05%, 0.5% or 1%. In some embodiments, the composition comprises CHAPS at or at about 0.02% w/v.

In some embodiments, the formulation or formulation with conjugate is made as a concentrate, e.g., a stock solution, for later dilution and use. In some embodiments, the stock solution contains the surfactant, e.g., non-ionic surfactant or zwitterionic surfactant for up to at or about 30%, 25%, 15%, 10%, or 5% weight to volume (w/v), or within a range defined by any of the foregoing. In some embodiments, the stock solution contains polysorbate, e.g., polysorbate 20 or polysorbate 80, for up to at or about 30%, 25%, 15%, 10%, or 5% weight to volume (w/v), or within a range defined by any of the foregoing. In some embodiments, the stock solution contains PEG for up to about 30%, 25%, 15%, 10%, or 5% weight to volume (w/v). In some embodiments, the stock solution contains polysorbate, e.g., polysorbate 20 or polysorbate 80, for up to at or about 30%, 25%, 15%, 10%, or 5% weight to volume (w/v), or within a range defined by any of the foregoing. In some embodiments, the stock solution contains Pluronic® F-68, Triton X-100® or 3-[(3-Cholamidopropyl) dimethylammonio]-1-propanesulfonate (CHAPS) for up to at or about 30%, 25%, 15%, 10%, or 5% weight to volume (w/v), or within a range defined by any of the foregoing.

In some embodiments, the stabilizing agent is one or more protectants. Exemplary protectants for use with the compositions herein include trehalose, sucrose sorbitol, mannitol, xylitol, glycerol, and/or alkyl saccharides. In some embodiments, the protectant is present in the composition at a concentration of a percentage by volume (w/v) of between 1% and 20%, between 1% and 10%, between 5% and 20%, between 5% and 15%, between 5% and 10%, 5% and 9%, between 5% and 8%, between 5% and 7%, and between 5% and 6%. In some embodiments, the protectant is present in the composition at a concentration of a percentage by volume (w/v) of or of about 1%, 2%, 3%, 4%, 5%, 6%, 7%, 8%, 9%, 10%, 11%, 12% 13%, 14% or 15%, or within a range defined by any of the foregoing. In some embodiments, the stabilizing agents include a protectant and a surfactant, e.g., non-ionic surfactant or a zwitterionic surfactant.

In particular embodiments, the one or more protectants of the pharmaceutical compositions are or include trehalose. In certain embodiments, the trehalose is present in the composition at a percentage by volume (w/v) of between 1% and 20%, between 1% and 5%, between 1% and 10%, between 5% and 10%, between 8% and 10%, and between 5% and 9%. In some embodiments, the trehalose is present at a percentage by volume (w/v) at, at least, or at about 1%, 2%, 3%, 4%, 5%, 6%, 7%, 8%, 9%, 10%, 11%, 12%, 13%, 14% or 15%, or within a range defined by any of the foregoing. In some embodiments, the composition comprises trehalose at or at about 9% w/v. In some embodiments, the stabilizing agents include a trehalose and a surfactant, e.g., a non-ionic surfactant or a zwitterionic surfactant. In some embodiments, the stabilizing agents include a trehalose and a non-ionic surfactant.

In particular embodiments, the one or more protectants of the pharmaceutical compositions are or include sucrose. In certain embodiments, the sucrose is present in the composition at a percentage by volume (w/v) of between 1% and 20%, between 1% and 5%, between 1% and 10%, between 5% and 10%, between 8% and 10%, and between 5% and 9%. In some embodiments, the sucrose is present at a percentage by volume (w/v) at, at least, or at about 1%, 2%, 3%, 4%, 5%, 6%, 7%, 8%, 9%, 10%, 11%, 12%, 13%, 14% or 15%, or within a range defined by any of the foregoing. In some embodiments, the composition comprises sucrose at or at about 9% w/v. In some embodiments, the stabilizing agents include a sucrose and a surfactant, e.g., a non-ionic surfactant or a zwitterionic surfactant. In some embodiments, the stabilizing agents include a sucrose and a non-ionic surfactant.

In particular embodiments, the one or more protectants of the pharmaceutical compositions are or include sorbitol. In certain embodiments, the sorbitol is present in the composition at a percentage by volume (w/v) of between 1% and 20%, between 1% and 5%, between 1% and 10%, between 5% and 10%, between 8% and 10%, and between 5% and 9%. In some embodiments, the sorbitol is present at a percentage by volume (w/v) at, at least, or at about 1%, 2%, 3%, 4%, 5%, 6%, 7%, 8%, 9%, 10%, 11%, 12%, 13%, 14% or 15%, or within a range defined by any of the foregoing. In some embodiments, the composition comprises sorbitol at or at about 9% w/v. In some embodiments, the stabilizing agents include a sorbitol and a surfactant, e.g., a non-ionic surfactant or a zwitterionic surfactant. In some embodiments, the stabilizing agents include a sorbitol and a non-ionic surfactant.

In particular embodiments, the one or more protectants of the pharmaceutical compositions are or include mannitol. In certain embodiments, the mannitol is present in the composition at a percentage by volume (w/v) of between 1% and 20%, between 1% and 5%, between 1% and 10%, between 5% and 10%, between 8% and 10%, and between 5% and 9%. In some embodiments, the mannitol is present at a percentage by volume (w/v) at, at least, or at about 1%, 2%, 3%, 4%, 5%, 6%, 7%, 8%, 9%, 10%, 11%, 12%, 13%, 14% or 15%, or within a range defined by any of the foregoing. In some embodiments, the composition comprises mannitol at or at about 9% w/v. In some embodiments, the stabilizing agents include a mannitol and a surfactant, e.g., a non-ionic surfactant or a zwitterionic surfactant. In some embodiments, the stabilizing agents include a mannitol and a non-ionic surfactant.

In some embodiments, the conjugate is formulated as a concentrate (stock solution) and the protectant, such as trehalose, sucrose, sorbitol or mannitol, is present at a percentage by weight to volume (w/v) at or at about 20%, 25%, 30%, 35%, 40% or 50%, or within a range defined by any of the foregoing.

In some embodiments, the stock solution contains the surfactant, e.g., non-ionic surfactant or zwitterionic surfactant, for up to at or about 30%, 25%, 15%, 10%, or 5% weight to volume (w/v), or within a range defined by any of the foregoing. In some embodiments, the stock solution contains polysorbate, e.g., polysorbate 20 or polysorbate 80, for up to at or about 30%, 25%, 15%, 10%, or 5% weight to volume (w/v), or within a range defined by any of the foregoing. In some embodiments, the stock solution contains PEG for up to about 30%, 25%, 15%, 10%, or 5% weight to volume (w/v). In some embodiments, the stock solution contains polysorbate, e.g., polysorbate 20 or polysorbate 80, for up to at or about 30%, 25%, 15%, 10%, or 5% weight to volume (w/v), or within a range defined by any of the foregoing. In some embodiments, the stock solution contains Pluronic® F-68, Triton X-100® or 3-[(3-Cholamidopropyl) dimethylammonio]-1-propanesulfonate (CHAPS) for up to at or about 30%, 25%, 15%, 10%, or 5% weight to volume (w/v), or within a range defined by any of the foregoing.

In some embodiments, the conjugate is formulated as a concentrate (e.g., stock solution) concentrate is diluted for use, such as dilution into a pharmaceutically acceptable aqueous diluent such as an aqueous infusion fluid, which may be used to facilitate subsequent systemic administration, such as by parenteral infusion, injection or intravenous (IV) infusion. Exemplary aqueous diluents include normal saline or dextrose in water. In some embodiments, the aqueous diluent further includes a small amount of amphiphilic polymer such as PEG, Tween, or Pluronic. In some embodiments, the concentrate is diluted 2-fold, 3-fold-, 4-fold, 5-fold, 10-fold or 20-fold into a pharmaceutically acceptable aqueous diluent prior to administration.

In particular embodiments, the stabilizing agents are or include a surfactant, e.g., a non-ionic surfactant or a zwitterionic surfactant, and a protectant. In some embodiments, the stabilizing agents include (i) a polysorbate, a lecithin, a polyoxyethylene glycol (PEG), a polyoxyethylene glycol sorbitan alkyl ester, a polyethylene glycol octylphenyl ether, a block copolymer of polyethylene glycol and polypropylene glycol, a polyethylene glycol alkyl ether, or combinations thereof, and (ii) a protectant. In some embodiments, the stabilizing agents include (i) a zwitterionic surfactant and (ii) a protectant. In certain embodiments, the stabilizing agents are or include (i) a polysorbate and (ii) a protectant. In various embodiments, the stabilizing agents are or include (i) a surfactant, e.g., a non-ionic surfactant or a zwitterionic surfactant, and (ii) a trehalose, sorbitol, sucrose, mannitol, xylitol or glycerol. In particular embodiments, the stabilizing agents are or include a polysorbate, e.g., polysorbate 80, and trehalose. In particular embodiments, the stabilizing agents are or include a PEG, e.g., PEG 8000, and trehalose. In particular embodiments, the stabilizing agents are or include a block copolymer of polyethylene glycol and polypropylene glycol, e.g., Pluronic® F-68, and trehalose. In particular embodiments, the stabilizing agents are or include a polyethylene glycol octylphenyl ether, e.g., Triton X-100®, and trehalose. In particular embodiments, the stabilizing agents are or include a zwitterionic surfactant, e.g., CHAPS, and trehalose. In particular embodiments, the stabilizing agents are or include a polysorbate, e.g., polysorbate 80, and sucrose. In particular embodiments, the stabilizing agents are or include a polysorbate, e.g., polysorbate 80, and sorbitol. In particular embodiments, the stabilizing agents are or include a polysorbate, e.g., polysorbate 80, and mannitol.

In some embodiments, the provided pharmaceutical compositions, e.g., compositions containing the dye conjugate, such as cetuximab-IR700, are formulated in a pharmaceutically acceptable buffer at a pH greater than 6.0, such as generally from or from about pH 6.0 to or to about 10. Pharmaceutically acceptable buffers may include, but are not limited to, sodium bicarbonate, sodium phosphate, dipotassium phosphate, potassium bicarbonate, sodium carbonate, potassium carbonate, and mixtures thereof. In particular embodiments, the pharmaceutical composition contains between or contains between about 100 nM and 1 M, between 100 µM and 100 mM, between 1 mM and 500 mM, between 1 mM and 50 mM, between 10 mM and 200 mM, between 5 mM and 100 mM, between 1 mM and 20 mM, between 5 mM and 25 mM, between 10 mM and 50 mM, each inclusive, or contains, contains about, or contains at least 100 µM, 500 µM, 1 mM, 5 mM, 10 mM, 50 mM, 100 mM, 150 mM, 200 mM, 250 mM, 300 mM, 350 mM, 400 mM, 450 mM, 500 mM, or greater than 500 mM of the pharmaceutically acceptable buffer.

In some embodiments, the pharmaceutically acceptable buffer is sodium phosphate. In particular embodiments, the composition, e.g., the pharmaceutical composition, contains between or between about 100 µM and 1 M, between 1 mM and 200 mM, between 1 mM and 50 mM, or between 5 mM and 25 mM, or contains, contains about, or contains at least 100 µM, 500 µM, 1 mM, 5 mM, 10 mM, 15 mM, 20 mM, 25 mM, 50 mM, or greater than 50 mM sodium phosphate.

In some embodiments, the pH of the composition, e.g., the pharmaceutical composition, provided herein is between or between about 6 and at or about 8.0, such as between or between about 6.9 and at or about 7.3, such as at or about pH 7.1. In some embodiments, the pH of the pharmaceutically acceptable buffer is at least or at or about 5, at least or at or about 6, at least or at or about 7, at least or at or about 8, at least or at or about 9 or at least or at or about 10, or is at or about 7.1. In some embodiments, the composition has a pH of at or of about pH 6.0 to at or about pH 8.0, inclusive. In some embodiments, the composition has a pH of at or of about pH 6.8 to at or about pH 7.4, inclusive. In some embodiments, the composition has a pH of from or from about pH 7.1 to or to about pH 7.3. In some embodiments, the composition has a pH of or of about 6.8, 6.9, 7.0, 7.1, 7.2, 7.3 or 7.4. In some embodiments, the composition has a pH of or of about pH 7.1.

In some embodiments, the provided pharmaceutical composition contains a conjugate, e.g., cetuximab-IR700 conjugate, and stabilizing agents that are or include a polysorbate, e.g., polysorbate 80, and a protectant, e.g., trehalose. In various embodiments, the pharmaceutical composition contains any of the conjugates described herein, e.g., cetuximab-IR700 conjugate, and stabilizing agents that are or include a polysorbate, e.g., polysorbate 80, and a protectant, e.g., trehalose. In some embodiments, the provided pharmaceutical composition contains a conjugate, e.g., cetuximab-IR700 conjugate, and stabilizing agents that are or include a PEG, e.g., PEG 8000, and a protectant, e.g., trehalose. In some embodiments, the provided pharmaceutical composition contains a conjugate, e.g., cetuximab-IR700 conjugate, and stabilizing agents that are or include a block copolymer of polyethylene glycol and polypropylene glycol, e.g., Pluronic® F-68, and a protectant, e.g., trehalose. In some embodiments, the provided pharmaceutical composition contains a conjugate, e.g., cetuximab-IR700 conjugate, and stabilizing agents that are or include a polyethylene glycol octylphenyl ether, e.g., Triton X-100®, and a protectant, e.g., trehalose. In some embodiments, the provided pharmaceutical composition contains a conjugate, e.g., cetuximab-IR700 conjugate, and stabilizing agents that are or include a zwitterionic surfactant, e.g., CHAPS, and a protectant, e.g., trehalose. In some embodiments, the provided pharmaceutical composition contains a conjugate, e.g., cetuximab-IR700 conjugate, and stabilizing agents that are or include a polysorbate, e.g., polysorbate 80, and a protectant, e.g., sucrose. In some embodiments, the provided pharmaceutical composition contains a conjugate, e.g., cetuximab-IR700 conjugate, and stabilizing agents that are or include a polysorbate, e.g., polysorbate 80, and a protectant, e.g., sorbitol. In some embodiments, the provided pharmaceutical composition contains a conjugate, e.g., cetuximab-IR700 conjugate, and stabilizing agents that are or include a polysorbate, e.g., polysorbate 80, and a protectant, e.g., mannitol.

In particular embodiments, the composition, e.g., pharmaceutical composition, contains (1) between 0.01 mg/mL and 500 mg/mL, between 0.1 mg/mL and 100 mg/mL, between 0.5 mg/mL and 50 mg/mL, between 1 mg/mL and 25 mg/mL, or between 2 mg/mL and 10 mg/mL (each inclusive) of a conjugate provided or described herein, such as cetuximab-IR700, (2) polysorbate 80, (3) trehalose, and (4) sodium phosphate. In certain embodiments, the composition, e.g., the pharmaceutical composition, contains (1) at, about, or at least 0.01 mg/mL, 0.05 mg/mL, 0.1 mg/mL, 0.5 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL or greater than 25 mg/mL of a conjugate provided or described herein, (2) polysorbate 80, (3) trehalose, and (4) sodium phosphate.

In particular embodiments, the composition, e.g., pharmaceutical composition, contains (1) a conjugate provided or described herein, such as cetuximab-IR700, (2) between 0.001% and 0.10%, between 0.001% and 0.075%, between 0.001% and 0.05%, between 0.001% and 0.01%, between 0.001% and 0.005%, 0.005% and 0.10%, between 0.005% and 0.075%, between 0.005% and 0.05%, between 0.005% and 0.01%, between 0.01% and 0.10%, between 0.01% and 0.075%, between 0.01% and 0.05%, between 0.05% and 0.1%, between 0.05% and 0.075% and between 0.075% and 0.10% polysorbate 80 by w/v (each inclusive), (3) trehalose, and (4) sodium phosphate. In various embodiments, the composition, e.g., the pharmaceutical composition, contains (1) a conjugate provided or described herein, (2) at, about, or at least 0.001%, 0.005%, 0.001%, 0.005%, 0.01%, 0.02%, 0.03%, 0.04%, 0.05%, 0.06%, 0.07%, 0.08%, 0.09%, 0.10%, 0.2%, 0.25%, or greater than 0.25% polysorbate 80 by w/v, (3) trehalose, and (4) sodium phosphate.

In particular embodiments, the composition, e.g., pharmaceutical composition, contains (1) a conjugate provided or described herein, such as cetuximab-IR700, (2) polysorbate 80, (3) between 1% and 20%, between 1% and 5%, between 1% and 10%, between 5% and 10%, between 8% and 10%, and between 5% and 9% trehalose by w/v, and (4) sodium phosphate. In certain embodiments, the composition, e.g., the pharmaceutical composition, contains (1) a conjugate provided or described herein, (2) polysorbate 80, (3) at, at least, or at about 1%, 2%, 3%, 4%, 5%, 6%, 7%, 8%, 9%, 10%, 11% 12%, 13%, 14%, 15%, 16%, 17%, 18%, 19%, or 20% trehalose, and (4) sodium phosphate.

In some embodiments, the composition, e.g., pharmaceutical composition, contains (1) a conjugate provided or described herein, such as cetuximab-IR700, (2) polysorbate 80, (3) trehalose (4) between 100 µM and 1 M, between 1 mM and 200 mM, between 1 mM and 50 mM, or between 5 mM and 25 mM sodium phosphate. In certain embodiments, the composition, e.g., the pharmaceutical composition, contains (1) a conjugate provided or described herein, (2) polysorbate 80, (3) at, at least, or at about 1%, 2%, 3%, 4%, 5%, 6%, 7%, 8%, 9%, 10%, 11% 12%, 13%, 14%, 15%, 16%, 17%, 18%, 19%, or 20% trehalose, and (4) at, at about, or at least 100 µM, 500 µM, 1 mM, 5 mM, 10 mM, 15 mM, 20 mM, 25 mM, 50 mM, or greater than 50 mM sodium phosphate.

In particular embodiments, the composition, e.g., pharmaceutical composition, contains (1) between 2 mg/mL and 10 mg/mL of a conjugate provided or described herein, such as cetuximab-IR700, (2) between 0.01% and 0.05% polysorbate 80 by w/v, (3) between 5% and 10% trehalose by w/v and (4) between 5 mM and 25 mM sodium phosphate.

In particular embodiments, the composition has a pH greater than 6.0, such as generally from or from about pH 6.0 to about 10, or between 6.0 and 8.0, 6.5 and 7.5, or at, at about, or at least 6.8, 6.9, 7.0, 7.1, 7.2, or 7.3.

In certain embodiments, the composition, e.g., pharmaceutical composition, contains (1) at or about 5 mg/mL of a conjugate, e.g., cetuximab-IR700, provided or described herein, (2) at or about 0.02% polysorbate 80 by w/v, (3) at or about 9% trehalose by w/v and (4) at or about 10 mM sodium phosphate, wherein the composition has a pH of or of about 7.1.

In particular embodiments, the composition, e.g., pharmaceutical composition, contains (1) between 0.01 mg/mL and 500 mg/mL, between 0.1 mg/mL and 100 mg/mL, between 0.5 mg/mL and 50 mg/mL, between 1 mg/mL and 25 mg/mL, or between 2 mg/mL and 10 mg/mL (each inclusive), such as at, about, or at least 0.01, 0.05, 0.1, 0.5, 1, 2, 3, 4, 5, 6, 7, 8, 9, 10, 15 mg/mL of a conjugate provided or described herein, such as cetuximab-IR700; (2) between 0.001% and 0.05%, between 0.005% and 0.05%, between 0.01% and 0.10%, between 0.01% and 0.075%, between 0.01% and 0.05%, between 0.05% and 0.1%, between 0.05% and 0.075% and between 0.075% and 0.10%, such as at, about, or at least 0.001%, 0.005%, 0.01%, 0.02%, 0.03%, 0.04%, 0.05%, 0.06%, 0.07%, 0.08%, 0.09%, 0.10%, 0.2%, 0.25%, or greater than 0.25% Pluronic® F-68 by w/v (each inclusive), (3) between 1% and 20%, between 1% and 10%, between 5% and 10%, between 8% and 10%, and between 5% and 9%, such as at, at least, or at about 1%, 2%, 3%, 4%, 5%, 6%, 7%, 8%, 9%, 10%, 11% 12%, 13%, 14%, 15%, 16%, 17%, 18%, 19%, or 20% trehalose by w/v, and (4) between 100 µM and 1 M, between 1 mM and 200 mM, between 1 mM and 50 mM, or between 5 mM and 25 mM, such as at, at about, or at least 100 µM, 500 µM, 1 mM, 5 mM, 10 mM, 15 mM, 20 mM, 25 mM, 50 mM, or greater than 50 mM sodium phosphate.

In particular embodiments, the composition, e.g., pharmaceutical composition, contains (1) between 2 mg/mL and 10 mg/mL of a conjugate provided or described herein, such as cetuximab-IR700, (2) between 0.01% and 0.05% Pluronic® F-68 by w/v, (3) between 5% and 10% trehalose by w/v and (4) between 5 mM and 25 mM sodium phosphate. In certain embodiments, the composition, e.g., pharmaceutical composition, contains (1) at or about 5 mg/mL of a conjugate, e.g., cetuximab-IR700, provided or described herein, (2) at or about 0.02% Pluronic® F-68 by w/v, (3) at or about 9% trehalose by w/v and (4) at or about 10 mM sodium phosphate, wherein the composition has a pH of or of about 7.1.

In particular embodiments, the composition, e.g., pharmaceutical composition, contains (1) between 0.01 mg/mL and 500 mg/mL, between 0.1 mg/mL and 100 mg/mL, between 0.5 mg/mL and 50 mg/mL, between 1 mg/mL and 25 mg/mL, or between 2 mg/mL and 10 mg/mL (each inclusive), such as at, about, or at least 0.01, 0.05, 0.1, 0.5, 1, 2, 3, 4, 5, 6, 7, 8, 9, 10, 15 mg/mL of a conjugate provided or described herein, such as cetuximab-IR700; (2) between 0.001% and 0.05%, between 0.005% and 0.05%, between 0.01% and 0.10%, between 0.01% and 0.075%, between 0.01% and 0.05%, between 0.05% and 0.1%, between 0.05% and 0.075% and between 0.075% and 0.10%, such as at, about, or at least 0.001%, 0.005%, 0.01%, 0.02%, 0.03%, 0.04%, 0.05%, 0.06%, 0.07%, 0.08%, 0.09%, 0.10%, 0.2%, 0.25%, or greater than 0.25% PEG 8000 by w/v (each inclusive), (3) between 1% and 20%, between 1% and 10%, between 5% and 10%, between 8% and 10%, and between 5% and 9%, such as at, at least, or at about 1%, 2%, 3%, 4%, 5%, 6%, 7%, 8%, 9%, 10%, 11% 12%, 13%, 14%, 15%, 16%, 17%, 18%, 19%, or 20% trehalose by w/v, and (4) between 100 UM and 1 M, between 1 mM and 200 mM, between 1 mM and 50 mM, or between 5 mM and 25 mM, such as at, at about, or at least 100 µM, 500 µM, 1 mM, 5 mM, 10 mM, 15 mM, 20 mM, 25 mM, 50 mM, or greater than 50 mM sodium phosphate.

In particular embodiments, the composition, e.g., pharmaceutical composition, contains (1) between 2 mg/mL and 10 mg/mL of a conjugate provided or described herein, such as cetuximab-IR700, (2) between 0.01% and 0.05% PEG 8000 by w/v, (3) between 5% and 10% trehalose by w/v and (4) between 5 mM and 25 mM sodium phosphate. In certain embodiments, the composition, e.g., pharmaceutical composition, contains (1) at or about 5 mg/mL of a conjugate, e.g., cetuximab-IR700, provided or described herein, (2) at or about 0.02% PEG 8000 by w/v, (3) at or about 9% trehalose by w/v and (4) at or about 10 mM sodium phosphate, wherein the composition has a pH of or of about 7.1.

In particular embodiments, the composition, e.g., pharmaceutical composition, contains (1) between 0.01 mg/mL and 500 mg/mL, between 0.1 mg/mL and 100 mg/mL, between 0.5 mg/mL and 50 mg/mL, between 1 mg/mL and 25 mg/mL, or between 2 mg/mL and 10 mg/mL (each inclusive), such as at, about, or at least 0.01, 0.05, 0.1, 0.5, 1, 2, 3, 4, 5, 6, 7, 8, 9, 10, 15 mg/mL of a conjugate provided or described herein, such as cetuximab-IR700; (2) between 0.001% and 0.05%, between 0.005% and 0.05%, between 0.01% and 0.10%, between 0.01% and 0.075%, between 0.01% and 0.05%, between 0.05% and 0.1%, between 0.05% and 0.075% and between 0.075% and 0.10%, such as at, about, or at least 0.001%, 0.005%, 0.01%, 0.02%, 0.03%, 0.04%, 0.05%, 0.06%, 0.07%, 0.08%, 0.09%, 0.10%, 0.2%, 0.25%, or greater than 0.25% polysorbate 80 by w/v (each inclusive), (3) between 1% and 20%, between 1% and 10%, between 5% and 10%, between 8% and 10%, and between 5% and 9%, such as at, at least, or at about 1%, 2%, 3%, 4%, 5%, 6%, 7%, 8%, 9%, 10%, 11% 12%, 13%, 14%, 15%, 16%, 17%, 18%, 19%, or 20% sucrose by w/v, and (4) between 100 μM and 1 M, between 1 mM and 200 mM, between 1 mM and 50 mM, or between 5 mM and 25 mM, such as at, at about, or at least 100 μM, 500 μM, 1 mM, 5 mM, 10 mM, 15 mM, 20 mM, 25 mM, 50 mM, or greater than 50 mM sodium phosphate.

In particular embodiments, the composition, e.g., pharmaceutical composition, contains (1) between 2 mg/mL and 10 mg/mL of a conjugate provided or described herein, such as cetuximab-IR700, (2) between 0.01% and 0.05% polysorbate 80 by w/v, (3) between 5% and 10% sucrose by w/v and (4) between 5 mM and 25 mM sodium phosphate. In certain embodiments, the composition, e.g., pharmaceutical composition, contains (1) at or about 5 mg/mL of a conjugate, e.g., cetuximab-IR700, provided or described herein, (2) at or about 0.02% polysorbate 80 by w/v, (3) at or about 9% sucrose by w/v and (4) at or about 10 mM sodium phosphate, wherein the composition has a pH of or of about 7.1.

In particular embodiments, the composition, e.g., pharmaceutical composition, contains (1) between 0.01 mg/mL and 500 mg/mL, between 0.1 mg/mL and 100 mg/mL, between 0.5 mg/mL and 50 mg/mL, between 1 mg/mL and 25 mg/mL, or between 2 mg/mL and 10 mg/mL (each inclusive), such as at, about, or at least 0.01, 0.05, 0.1, 0.5, 1, 2, 3, 4, 5, 6, 7, 8, 9, 10, 15 mg/mL of a conjugate provided or described herein, such as cetuximab-IR700; (2) between 0.001% and 0.05%, between 0.005% and 0.05%, between 0.01% and 0.10%, between 0.01% and 0.075%, between 0.01% and 0.05%, between 0.05% and 0.1%, between 0.05% and 0.075% and between 0.075% and 0.10%, such as at, about, or at least 0.001%, 0.005%, 0.01%, 0.02%, 0.03%, 0.04%, 0.05%, 0.06%, 0.07%, 0.08%, 0.09%, 0.10%, 0.2%, 0.25%, or greater than 0.25% polysorbate 80 by w/v (each inclusive), (3) between 1% and 20%, between 1% and 10%, between 5% and 10%, between 8% and 10%, and between 5% and 9%, such as at, at least, or at about 1%, 2%, 3%, 4%, 5%, 6%, 7%, 8%, 9%, 10%, 11% 12%, 13%, 14%, 15%, 16%, 17%, 18%, 19%, or 20% sorbitol by w/v, and (4) between 100 UM and 1 M, between 1 mM and 200 mM, between 1 mM and 50 mM, or between 5 mM and 25 mM, such as at, at about, or at least 100 μM, 500 μM, 1 mM, 5 mM, 10 mM, 15 mM, 20 mM, 25 mM, 50 mM, or greater than 50 mM sodium phosphate.

In particular embodiments, the composition, e.g., pharmaceutical composition, contains (1) between 2 mg/mL and 10 mg/mL of a conjugate provided or described herein, such as cetuximab-IR700, (2) between 0.01% and 0.05% polysorbate 80 by w/v, (3) between 5% and 10% sorbitol by w/v and (4) between 5 mM and 25 mM sodium phosphate. In certain embodiments, the composition, e.g., pharmaceutical composition, contains (1) at or about 5 mg/mL of a conjugate, e.g., cetuximab-IR700, provided or described herein, (2) at or about 0.02% polysorbate 80 by w/v, (3) at or about 9% sorbitol by w/v and (4) at or about 10 mM sodium phosphate, wherein the composition has a pH of or of about 7.1.

In particular embodiments, the composition, e.g., pharmaceutical composition, contains (1) between 0.01 mg/mL and 500 mg/mL, between 0.1 mg/mL and 100 mg/mL, between 0.5 mg/mL and 50 mg/mL, between 1 mg/mL and 25 mg/mL, or between 2 mg/mL and 10 mg/mL (each inclusive), such as at, about, or at least 0.01, 0.05, 0.1, 0.5, 1, 2, 3, 4, 5, 6, 7, 8, 9, 10, 15 mg/mL of a conjugate provided or described herein, such as cetuximab-IR700; (2) between 0.001% and 0.05%, between 0.005% and 0.05%, between 0.01% and 0.10%, between 0.01% and 0.075%, between 0.01% and 0.05%, between 0.05% and 0.1%, between 0.05% and 0.075% and between 0.075% and 0.10%, such as at, about, or at least 0.001%, 0.005%, 0.01%, 0.02%, 0.03%, 0.04%, 0.05%, 0.06%, 0.07%, 0.08%, 0.09%, 0.10%, 0.2%, 0.25%, or greater than 0.25% polysorbate 80 by w/v (each inclusive), (3) between 1% and 20%, between 1% and 10%, between 5% and 10%, between 8% and 10%, and between 5% and 9%, such as at, at least, or at about 1%, 2%, 3%, 4%, 5%, 6%, 7%, 8%, 9%, 10%, 11% 12%, 13%, 14%, 15%, 16%, 17%, 18%, 19%, or 20% mannitol by w/v, and (4) between 100 μM and 1 M, between 1 mM and 200 mM, between 1 mM and 50 mM, or between 5 mM and 25 mM, such as at, at about, or at least 100 μM, 500 μM, 1 mM, 5 mM, 10 mM, 15 mM, 20 mM, 25 mM, 50 mM, or greater than 50 mM sodium phosphate.

In particular embodiments, the composition, e.g., pharmaceutical composition, contains (1) between 2 mg/mL and 10 mg/mL of a conjugate provided or described herein, such as cetuximab-IR700, (2) between 0.01% and 0.05% polysorbate 80 by w/v, (3) between 5% and 10% mannitol by w/v and (4) between 5 mM and 25 mM sodium phosphate. In certain embodiments, the composition, e.g., pharmaceutical composition, contains (1) at or about 5 mg/mL of a conjugate, e.g., cetuximab-IR700, provided or described herein, (2) at or about 0.02% polysorbate 80 by w/v, (3) at or about 9% mannitol by w/v and (4) at or about 10 mM sodium phosphate, wherein the composition has a pH of or of about 7.1.

In particular embodiments, the composition, e.g., pharmaceutical composition, is formulated as a concentrate and the concentrate is diluted for use, such as dilution into a pharmaceutically acceptable aqueous diluent such as an aqueous infusion fluid, which may be used to facilitate subsequent systemic administration, such as by parenteral infusion, injection or intravenous (IV) infusion. Exemplary aqueous diluents include normal saline or dextrose in water. In some embodiments, the aqueous diluent further includes a small amount of amphiphilic polymer such as PEG, Tween, or Pluronic. In some embodiments, the concentrate is diluted 2-fold, 3-fold-, 4-fold, 5-fold, 10-fold or 20-fold into a pharmaceutically acceptable aqueous diluent prior to administration.

In some embodiments, the composition contains conventional pharmaceutical carriers and excipients appropriate for the type of administration contemplated. For example, in some embodiments, parenteral formulations may contain a sterile aqueous solution or suspension of the conjugate. In some embodiments, compositions for enteral administration may contain an effective amount of the conjugate in aqueous solution or suspension that may optionally include buffers, surfactants, thixotropic agents, and flavoring agents.

In some embodiments, the compositions that include the compounds, such as a conjugate, can be formulated in a pharmaceutically acceptable buffer, such as that containing a pharmaceutically acceptable carrier or vehicle. Generally, the pharmaceutically acceptable carriers or vehicles, such as those present in the pharmaceutically acceptable buffer, can be any known in the art. Remington's Pharmaceutical Sciences, by E. W. Martin, Mack Publishing Co., Easton, Pa., 19th Edition (1995), describes compositions and formulations suitable for pharmaceutical delivery of one or more therapeutic compounds. Pharmaceutically acceptable compositions generally are prepared in view of approvals for a regulatory agency or other agency prepared in accordance with generally recognized pharmacopeia for use in animals and in humans.

Pharmaceutical compositions can include carriers such as a diluent, adjuvant, excipient, or vehicle with which the compound is administered. Examples of suitable pharmaceutical carriers are described in "Remington's Pharmaceutical Sciences" by E. W. Martin. Such compositions will contain a therapeutically effective amount of the compound, generally in purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A composition, if desired, also can contain minor amounts of wetting or emulsifying agents, or pH buffering agents, for example, acetate, sodium citrate, cyclodextrin derivatives, sorbitan monolaurate, triethanolamine sodium acetate, triethanolamine oleate, and other such agents.

In some embodiments, pharmaceutical preparation can be in liquid form, for example, solutions, syrups, or suspensions. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). In some cases, pharmaceutical preparations can be presented in lyophilized form for reconstitution with water or other suitable vehicle before use.

In some embodiments, the nature of the pharmaceutically acceptable buffer, or carrier, depends on the particular mode of administration being employed. For instance, in some embodiments, parenteral formulations may comprise injectable fluids that include pharmaceutically and physiologically acceptable fluids such as water, physiological saline, balanced salt solutions, aqueous dextrose, or glycerol as a vehicle. In some embodiments, for solid compositions, for example powder, pill, tablet, or capsule forms, non-toxic solid carriers can include, for example, pharmaceutical grades of mannitol, lactose, starch, or magnesium stearate. In addition to biologically-neutral carriers, pharmaceutical compositions to be administered can in some embodiments contain minor amounts of non-toxic auxiliary substances, such as wetting or emulsifying agents, preservatives, and pH buffering agents, for example sodium acetate or sorbitan monolaurate.

The compositions containing the compounds can be formulated into suitable pharmaceutical preparations such as solutions, suspensions, tablets, dispersible tablets, pills, capsules, powders, sustained release formulations or elixirs, for oral administrate, as well as transdermal patch preparation and dry powder inhalers. Typically, the compositions containing the compounds are formulated into pharmaceutical compositions using techniques and procedures well known in the art (see e.g., Ansel Introduction to Pharmaceutical Dosage Forms, Fourth Edition, 1985, 126). Generally, the mode of formulation is a function of the route of administration.

Compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. Other modes of administration also are contemplated. Administration can be local, topical, or systemic depending upon the locus of treatment. Local administration to an area in need of treatment can be achieved by, for example, but not limited to, local infusion during surgery, topical application, e.g., in conjunction with a wound dressing after surgery, by injection, by means of a catheter, by means of a suppository, or by means of an implant.

Parenteral administration, generally characterized by injection, either subcutaneously, intramuscularly, intratumorally, intravenously or intradermally is contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol, or ethanol. In addition, if desired, the pharmaceutical compositions to be administered may also contain an activator in the form of a solvent such as pH buffering agents, metal ion salts, or other such buffers. The pharmaceutical compositions also may contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. The percentage of active compound contained in such parenteral compositions is highly dependent on the specific nature thereof, as well as the activity of the compound and the needs of the subject.

Injectables are designed for local and systemic administration. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous. If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations of the provided compositions include aqueous vehicles, nonaqueous vehicles, antimicrobial agents, isotonic agents, buffers, antioxidants, local anesthetics, suspending and dispersing agents, emulsifying agents, sequestering or chelating agents, and other pharmaceutically acceptable substances. Examples of aqueous vehicles include sodium chloride injection, ringers injection, isotonic dextrose injection, sterile water injection, dextrose, and lactated ringers injection. Nonaqueous parenteral vehicles include fixed oils of vegetable origin, cottonseed oil, corn oil, sesame oil, and peanut oil. Antimicrobial agents in bacteriostatic or fungistatic concentrations can be added to parenteral preparations packaged in multiple-dose containers, which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate.

If administered intravenously, suitable carriers include physiological saline, phosphate buffered aqueous solutions or phosphate buffered saline (PBS), and solutions containing thickening and solubilizing agents, such as glucose, polyethylene glycol, and polypropylene glycol and mixtures thereof.

The compositions provided herein can be formulated for single dosage administration or for multiple dosage administration. The agents can be formulated for direct administration. The composition can be provided as a liquid or lyophilized formulation. Where the composition is provided in lyophilized form it can be reconstituted just prior to use by an appropriate buffer, for example, a sterile saline solution.

The compositions provided herein can also be administered with other biologically active agents, either sequentially, intermittently or in the same composition. Administration also can include controlled release systems including controlled release formulations and device controlled release, such as by means of a pump.

The most suitable route in any given case depends on a variety of factors, such as the nature of the disease, the progress of the disease, the severity of the disease and the particular composition which is used. For example, compositions are administered systemically, for example, via intravenous administration. Subcutaneous methods also can be employed, although increased absorption times can be necessary to ensure equivalent bioavailability compared to intravenous methods.

The pharmaceutical compositions provided herein can be formulated in dosage forms appropriate for each route of administration. Pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle, or diluent. Unit dosage forms, include, but are not limited to, tablets, capsules, pills, powders, granules, sterile parenteral solutions or suspensions, frozen solutions and suspensions and oral solutions or suspensions, and oil water emulsions containing suitable quantities of the compounds or pharmaceutically acceptable derivatives thereof. Unit dose forms can be contained ampoules and syringes or individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules, or bottles of pints or gallons. Hence, multiple dose form is a multiple of unit doses that are not segregated in packaging. Generally, dosage forms or compositions containing active ingredient in the range of 0.005% to 100% with the balance made up from non-toxic carrier can be prepared. Pharmaceutical compositions can be formulated in dosage forms appropriate for each route of administration.

The concentration of the pharmaceutically active compound contained in the compositions provided herein is adjusted so that an injection provides an effective amount to produce the desired pharmacological effect. The exact dose depends on the age, weight and condition of the patient or animal as is known in the art. The unit-dose parenteral preparations are packaged in an ampoule, a vial, or a syringe with a needle. The volume of liquid solution or reconstituted powder preparation, containing the pharmaceutically active compound, is a function of the disease to be treated and the particular article of manufacture chosen for package. All preparations for parenteral administration must be sterile, as is known and practiced in the art.

In some embodiments, the compositions provided herein are stable ready for use liquid compositions. In some embodiments, such liquid compositions contain the dye conjugate, e.g., conjugates of IR700 to an antibody, such as cetuximab-IR700, in dissolved or solubilized form and are intended to be used directly or upon further dilution with a diluent. Such liquid ready to use compositions include compositions that are ready to be directly administered to a subject without requiring an additional step such as reconstitution or dilution. In some embodiments, the IR700-antibody conjugate, such as cetuximab-IR700, in the provided compositions, e.g., ready to use liquid compositions, are stable for prolonged periods of time, for example for at or about or greater than 6 months, 7 months, 8 months, 9 months, 10 months, 11 months, 12 months, 18 months, 24 months or more. The stability can be manifested as reduced aggregation after exposure to particular conditions, such as agitation, pH, temperature, or storage for a period of time. In some embodiments, the IR700-antibody conjugate, such as cetuximab-IR700, in the provided compositions, e.g., ready to use liquid compositions, are stable when stored at 2° C. to 8° C. temperature, such as for prolonged periods of time, for example for at or about or greater than 6 months, 7 months, 8 months, 9 months, 10 months, 11 months, 12 months, 18 months, 24 months or more. In some embodiments, the IR700-antibody conjugate, such as cetuximab-IR700, in the provided compositions are stable when stored under thermal stress conditions, such as under higher temperature, e.g., at or about or more than 25° C., 30° C., 32° C., 35° C., 37° C. or 40° C., such as for prolonged periods of time, for example for at or about or greater than 1 day, 2 days, 3 days, 4 days, 5 days, 6 days, 7 days, 8 days, 9 days, 10 days, 11 days, 12 days, 13 days, 14 days, 1 week, 2 weeks, 3 weeks, 4, weeks, 5 weeks, 6 weeks, 7 weeks, 8 weeks, 1 month, 2 months, 3 months, 4 months, 5 months or 6 months or more, or within a range defined by any of the foregoing values.

In some embodiments, the compositions can be provided as a lyophilized powder, which can be reconstituted for administration as solutions, emulsions and other mixtures. They may also be reconstituted and formulated as solids or gels. The lyophilized powders can be prepared from any of the solutions described above. The sterile, lyophilized powder can be prepared by dissolving a phthalocyanine dye-antibody conjugate, such as cetuximab-IR700, in a buffer solution. The buffer solution may contain an excipient which improves the stability of other pharmacological components of the powder or reconstituted solution, prepared from the powder.

In some embodiments, subsequent sterile filtration of the solution followed by lyophilization under standard conditions known to those of skill in the art provides the desired formulation. Briefly, the lyophilized powder is prepared by dissolving an excipient, such as dextrose, sorbitol, fructose, corn syrup, xylitol, glycerin, glucose, sucrose, or other suitable agent, in a suitable buffer, such as citrate, sodium or potassium phosphate or other such buffer known to those of skill in the art. Then, a selected enzyme is added to the resulting mixture, and stirred until it dissolves. The resulting mixture is sterile filtered or treated to remove particulates and to ensure sterility, and apportioned into vials for lyophilization. Each vial can contain a single dosage (1 mg-1 g, generally 1-100 mg, such as 1-5 mg) or multiple dosages of the compound. The lyophilized powder can be stored under appropriate conditions, such as at about 4° C. to room temperature. Reconstitution of this lyophilized powder with a buffer solution provides a formulation for use in parenteral administration. The precise amount depends upon the indication treated and selected compound. Such amount can be empirically determined.

The compositions provided herein can be formulated for single dosage administration or for multiple dosage administration. The agents can be formulated for direct administration.

In some embodiments, the compositions provided herein are formulated in an amount for direct administration of the active compound, such as phthalocyanine dye-antibody conjugate, in a range from or from about 0.01 mg to or to about 3000 mg, from about 0.01 mg to or to about 1000 mg, from about 0.01 mg to or to about 500 mg, from about 0.01 mg to or to about 100 mg, from about 0.01 mg to or to about 50 mg, from about 0.01 mg to or to about 10 mg, from about 0.01 mg to or to about 1 mg, from about 0.01 mg to or to about 0.1 mg, from about 0.1 mg to or to about 2000 mg, from about 0.1 mg to or to about 1000 mg, from about 0.1 mg to or to about 500 mg, from about 0.1 mg to or to about 100 mg, from about 0.1 mg to or to about 50 mg, from about 0.1 mg to or to about 10 mg, from about 0.1 mg to or to about 1 mg, from about 1 mg to or to about 2000 mg, from about 1 mg to or to about 1000 mg, from about 1 mg to or to about 500 mg, from about 1 mg to or to about 100 mg, from about 1 mg to or to about 10 mg, from about 10 mg to or to about 2000 mg, from about 10 mg to or to about 1000 mg, from about 10 mg to or to about 500 mg, from about 10 mg to or to about 100 mg, from about 100 mg to or to about 2000 mg, from about 100 mg to or to about 1000 mg, from about 100 mg to or to about 500 mg, from about 500 mg to or to about 2000 mg, from about 500 mg to or to about 1000 mg, and from about 1000 mg to or to about 3000 mg. In some embodiments, the volume of the composition can be at or about 0.5 mL to at or about 1000 mL, such as at or about 0.5 mL to at or about 100 mL, at or about 0.5 mL to at or about 10 mL, at or about 1 mL to at or about 500 mL, at or about 1 mL to at or about 10 mL, such as at least or at least about or at or about 0.5 mL, 1 mL, 2 mL, 3 mL, 4 mL, 5 mL, 6 mL, 7 mL, 8 mL, 9 mL, 10 mL, 15 mL, 20 mL, 30 mL, 40 mL, 50 mL or more, or within a range defined by any of the foregoing. For example, the composition is formulated for single dosage administration of an amount between or between about 100 mg and at or about 500 mg, or between or between about 200 mg and at or about 400 mg. In some embodiments, the composition is formulated for single dosage administration of an amount between or between about 500 mg and at or about 1500 mg, 800 mg and 1200 mg or 1000 mg and 1500 mg. In some embodiments, the volume of the composition is between or between about 10 mL and at or about 1000 mL or 50 mL and 500 mL; or the volume of the composition is at least at or about 10 mL, 20 mL, 30 mL, 40 mL, 50 mL, 75 mL, 100 mL, 150 mL, 200 mL, 250 mL, 300 mL, 400 mL, 500 mL or 1000 mL, or within a range defined by any of the foregoing.

In some embodiments, the amount of the conjugate in the provided compositions is greater than or greater than about 1 mg, 1 gram, greater than or greater than about 2 grams, greater than or greater than about 3 grams, greater than or greater than about 4 grams, greater than or greater than about 5 grams or greater than or greater than about 10 grams. In some embodiments, the conjugate is produced using good manufacturing practice (GMP).

In some embodiments, the compositions provided herein are manufactured in an amount of the active compound, such as phthalocyanine dye-antibody conjugate, in a range from or from about 1 mg to or to about 10,000 grams.

In some embodiments, the conjugate (e.g., antibody-IR700) in a composition has a concentration within a range from at or about 0.1 mg/mL to at or about 1000 mg/mL, from at or about 0.1 mg/mL to at or about 500 mg/mL, from at or about 0.1 mg/mL to at or about 200 mg/mL, from at or about 0.1 mg/mL to at or about 100 mg/mL, from at or about 0.1 mg/mL to at or about 50 mg/mL, from at or about 0.1 mg/mL to at or about 10 mg/mL, from at or about 0.5 mg/mL to at or about 10 mg/mL, from at or about 0.5 mg/mL to at or about 5 mg/mL, from at or about 4.8 mg/mL to at or about 5.2 mg/mL, from at or about 10 mg/mL to at or about 50 mg/mL, from at or about 10 mg/mL to at or about 30 mg/mL, from at or about or 1.8 mg/mL to at or about 2.1 mg/mL. In some embodiments, the conjugate has a concentration of about 5.0 mg/mL, or has a concentration of 5.0 mg/mL. In some embodiments, the conjugate has a concentration of about 10.0 mg/mL, or has a concentration of 10.0 mg/mL. In some embodiments, the conjugate is cetuximab-IR700 and the composition is formulated for single dosage administration of an amount from at or about 100 mg/m$^2$ to at or about 1000 mg/m$^2$, from at or about 500 mg/m$^2$ to at or about 1000 mg/m$^2$, from at or about 500 mg/m$^2$ to 7 at or about 50 mg/m$^2$, or a single dosage administration of an amount of or of about 600 mg/m$^2$, 610 mg/m$^2$, 620 mg/m$^2$, 630 mg/m$^2$, 640 mg/m$^2$, 650 mg/m$^2$, 660 mg/m$^2$, 670 mg/m$^2$, 680 mg/m$^2$, 690 mg/m$^2$, or 700 mg/m$^2$, or within a range defined by any of the foregoing values. In some embodiments, the conjugate is cetuximab-IR700 and the composition is formulated for single dosage administration of an amount of or of about 100 mg/m$^2$, 160 mg/m$^2$, 320 mg/m$^2$, 400 mg/m$^2$, 450 mg/m$^2$, 500 mg/m$^2$, 600 mg/m$^2$, 640 mg/m$^2$, or 1280 mg/m$^2$, or within a range defined by any of the foregoing values.

In some embodiments the light dose to at or about be used with the composition ranges from at or about 1 J/cm$^2$ to at or about 150 J/cm$^2$, from at or about 10 J/cm$^2$ to at or about 100 J/cm$^2$, from at or about 25 J/cm$^2$ to at or about 75 J/cm$^2$, or is 50 J/cm$^2$ for frontal diffuser illumination. In some embodiments the light dose to at or about be used with the composition ranges from at or about 1 J/cm to at or about 400 J/cm for cylindrical fiber illumination, from at or about 10 J/cm to at or about 300 J/cm, from at or about 50 J/cm to at or about 200 J/cm, from at or about 75 J/cm to at or about 150 J/cm, or is 100 J/cm for cylindrical fiber illumination. In some embodiments, the light dose is carried out with a frontal light diffuser. In some embodiments, the light dose is carried out by superficial illumination. In some embodiments, the light dose is carried out by interstitial illumination. In some embodiments, the light dose is carried out with a cylindrical light diffuser at a dose of from at or about 50 J/cm fiber length to at or about 150 J/cm fiber length. In some embodiments, the light dose is carried out with a cylindrical light diffuser at a dose of or of about 100 J/cm fiber length. In some embodiments, the light dose is carried out with a frontal light diffuser at a dose of from at or about 25 J/cm$^2$ to at or about 100 J/cm$^2$. In some embodiments, the light dose is carried out with a frontal light diffuser at a dose of or of about 50 J/cm$^2$.

In some embodiments, the antibody of the conjugate is a biosimilar, interchangeable or biobetter of cetuximab. Such antibodies also include copy biologicals and biogenerics of cetuximab.

In some embodiments, the conjugate in the provided compositions has a molar ratio of dye to antibody molecule (e.g., IR700 to antibody) that is from or from about 1:1 to or to about 1000:1, from or from about 1:1 to or to about 100:1, from or from about 1:1 to or to about 10:1, from or from about 1:1 to or to about 4:1, from or from about 2:1 to or to about 3:1, or about 4:1 or 4:1 or about 3:1 or 3:1, or about 2:1 or 2:1. In some embodiments, the conjugate in the provided compositions has a molar ratio of dye to antibody molecule the is or is about 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0.

In some embodiments, the entire vial contents of the formulations of the compositions provided herein can be withdrawn for administration, or can be divided up into a plurality of dosages for multiple administrations. Upon withdrawal of an amount of drug for administration, the formulation can be further diluted if desired, such as diluted in water, saline (e.g., 0.9%) or other physiological solution.

C. Features of Phthalocyanine Dye-Antibody Conjugates

In some embodiments, the phthalocyanine dye-antibody conjugate in the provided compositions, such as an antibody-IR700 (e.g., cetuximab-IR700 conjugate), exhibits reduced aggregation after exposure to particular conditions, such as agitation, pH, temperature, or storage for a period of time.

In some embodiments, the stabilizing agent reduces aggregation by greater than or greater than about 1%, 5%, 10%, 20%, 30%, 40%, 50%, 60%, 70%, 80%, 90%, 95%, 99%, or more compared to aggregation in a composition comprising the conjugate but lacking the non-ionic surfactant and/or the protectant. In some embodiments, the aggregation can be caused by exposure to shear stress and/or agitation. In some embodiments, the aggregation can be caused by exposure to an acidic pH. In some embodiments, the aggregation can be caused by exposure to a temperature greater than about 25° C. In some embodiments, the aggregation can be caused to combinations of factors, including exposure to shear stress and/or agitation, acidic pH, and/or temperatures greater than about 25° C.

In some embodiments, the reduced aggregation is present after sheer stress and/or agitation; after exposure to a pH of less than or less than about pH 6.0; after 3 months at a temperature greater than or greater than about 25° C.

In some embodiments, the one or more stabilizing agent reduces aggregation that may occur following exposure to agitation, temperature and/or pH, thereby resulting in a phthalocyanine dye-antibody conjugate, for example cetuximab-IR700 conjugate, that is stable. In some embodiments, the purity, impurities, integrity, and/or potency of the conjugate in the provided compositions is not changed greater than acceptable specifications for manufacturing purposes to support clinical or commercial uses. In embodiments, the conjugate in the provided compositions is stable and exhibits reduced, including minimal, aggregation and retains potency and activity, such as after exposure to certain conditions as described, e.g., agitation, pH, temperature, including conditions associated with processing, manufacture, or storage of the dye.

In some embodiments, the phthalocyanine dye-antibody conjugate (e.g., cetuximab-IR700 conjugate) in the provided compositions displays minimal aggregation, such as agitation-induced aggregation, pH-induced aggregation, and/or aggregation during or following storage, such as for 3 months or more at a temperature of less than or about 30° C., less than or about 25° C., such as a temperature of 2-8° C. Thus, in some embodiments, the conjugate is stable for at least 3, 4, 5, 6, 7, 8, or 9 months, or is stable for about or at least a year or more at a temperature of less than or about 30° C., such as less than or about 25° C., such as generally a temperature of 2-8° C. In some embodiments, the conjugate is stable for more than 1 year at a temperature of less than or about 30° C., such as less than or about 25° C., such as generally a temperature of 2-8° C. In some embodiments, the IR700- antibody conjugate, such as cetuximab-IR700, in the provided compositions displays minimal aggregation and/or is stable, when stored under thermal stress conditions, such as under higher temperature, e.g., at or about or more than 25° C., 30° C., 32° C., 35° C., 37° C. or 40° C., such as for prolonged periods of time, for example for at or about or greater than 1 day, 2 days, 3 days, 4 days, 5 days, 6 days, 7 days, 8 days, 9 days, 10 days, 11 days, 12 days, 13 days, 14 days, 1 week, 2 weeks, 3 weeks, 4, weeks, 5 weeks, 6 weeks, 7 weeks, 8 weeks, 1 month, 2 months, 3 months, 4 months, 5 months or 6 months or more, or within a range defined by any of the foregoing values.

In some embodiments, after exposure to certain conditions as described, e.g., agitation, pH, temperature, including conditions associated with processing, manufacture, or storage of the dye, greater than about 90% of the conjugate in the composition is present as a main monomer component as a percentage of the total molecular weight of the conjugate present in the sample, no more than 10.0% of the conjugate exists as a high molecular weight component as a percentage of the total molecular weight of the conjugate present in the sample and/or the conjugate retains at least 20% and up to 100% of its integrity, such as its physical and functional qualities, including one or more of its purity (e.g., percent monomer content vs. aggregates, such as content of higher molecular weight components), identity (e.g., chemical composition, such as structural characteristics), potency (e.g., concentration or amount required to produce a pharmacologic response) or activity (e.g., PIT killing) compared to the conjugate prior to the exposure.

In some embodiments, after exposure to certain conditions as described, e.g., agitation, pH, temperature, including conditions associated with processing, manufacture, or storage of the dye, greater than 90% of the conjugate exists as a main monomer component as a percentage of the total molecular weight of the conjugate present in the sample, such as greater than 91%, greater than 92%, greater than 93%, greater than 94%, greater than 95%, greater than 96%, greater than 97%, greater than 98% or more exists as a main monomer component as a percentage of the total molecular weight of the conjugate present in the sample. In some embodiments, after exposure to certain conditions as described, e.g., agitation, pH, temperature, including conditions associated with processing, manufacture, or storage of the dye, no more than 10.0% of the conjugate exists as a high molecular weight component as a percentage of the total molecular weight of the conjugate present in the sample, and generally no more than 9.0%, no more than 8.0%, no more than 7.0%, no more than 6.0%, no more than 5.0%, no more than 4.0% or no more than 3.0% exists as a high molecular weight (HMW) component as a percentage of the total molecular weight of the conjugate present in the sample. In some embodiments, the presence of a high molecular weight component or a main monomer component can be identified using any method that can separate molecules based on size, such as by performing HPLC-SEC.

In some embodiments, after exposure to certain conditions as described, e.g., agitation, pH, temperature, including conditions associated with processing, manufacture, or storage of the dye, the integrity, purity, identity, potency, or activity of the conjugate in the composition is retained to at least or at least about 30%, 40%, 50%, 60%, 70%, 80%, 90% or 95% of the integrity, purity, identity, potency, or activity, respectively, of the conjugate prior to the exposure. In some embodiments, the potency of the conjugate can relate to the affinity of the conjugate for binding to its target molecule. In some embodiments, the potency can be assessed by its $ED_{50}$, i.e. the measure of the dose or amount of the conjugate that is pharmacologically effective or that exhibits a desired effect in 50% of the subjects exposed to the conjugate. In some embodiments, the activity relates to the biological activity, including the therapeutic effect and pharmacologic activity, of the conjugate that results upon in vivo administration, such as the activity of the conjugate to induce PIT killing. In some embodiments, biological activity can be observed in in vitro systems designed to test such activities. In some embodiments, the purity of the conjugate is related to the presence of monomers of the conjugate as compared to aggregates (e.g., high molecular weight components). In some embodiments, the purity can be assessed based on the percentages of monomers (e.g., main monomer peak) versus aggregates (e.g., high molecular weight components) in the composition. In some embodiments, the presence of a high molecular weight component or a main monomer component can be identified using any method that can separate molecules based on size, such as by performing HPLC-SEC.

In some embodiments, the main monomer component of a dye conjugate generally refers to a molecular weight species of the dye conjugate that represents the combined molecular weight of the dye and antibody present in the conjugate. Generally, the main monomer component is the species present in the greatest amount in a sample of a dye conjugate. For example, by HPLC-SEC methods, the main monomer component is generally the species of dye conjugate present as the largest peak in a preparation of a dye conjugate. Its exact molecular weight range in a dye-conjugate sample depends upon the particular sample (e.g., the particular dye and antibody) and the methods of preparation (e.g., the ratio of dye to antibody). The skilled artisan will recognize such a species. For example, for a conjugate containing an IR700 dye (having a molecular weight of about 1954.22 Da) and an antibody (having an average molecular weight of about 150,000 Da for a full-length antibody), the molecular weight range of the main monomer component typically is about 151,000 Da to 165,000 Da, such as 154,000 Da to 158,000 Da. In the exemplary experiment depicted in FIGS. 1A and 1B, the main monomer component of an exemplary antibody-dye conjugate include those that elute by HPLC-SEC between 8 and 9 minutes.

In some embodiments, the high molecular weight component of a dye conjugate generally refers to the molecular weight species of the dye conjugate that exhibit a molecular weight that is greater than the molecular weight of the main monomer component. In some embodiments, the increased or greater molecular weight can be due to aggregation of the dye conjugate. In some embodiments, the aggregation can be due to the formation of dimers, trimers or higher ordered oligomers. The exact molecular weight range of a high molecular weight component in a dye-conjugate sample will depend upon the particular sample (e.g., the particular dye and antibody), the methods of preparation (e.g., the ratio of dye to antibody) and, in some cases, the degree or extent of aggregation. The skilled artisan will recognize such a species. In some embodiments, for a dye conjugate of a full-length antibody and dye, such as IR700 dye, the high molecular weight component can be due to the presence of a dimer, trimer or higher ordered oligomer any that has a molecular weight generally greater than 200,000 Da, such as greater than 300,000 Da, 350,000 Da, 400,000 Da, 450,000 Da, 500,000 Da or greater. In the exemplary experiment depicted in FIGS. 1A and 1B, the high molecular components of an exemplary antibody-dye conjugate include those that elute by HPLC-SEC before 8 minutes, such as between 6 minutes and 8 minutes.

In some embodiments, stability of the conjugate in the provided compositions can be measured by assessing the percent monomer content of the conjugate. In some embodiments, the conjugate displays greater than 90% monomer content, such as at least 91%, 92%, 93%, 94%, 95%, 96%, 97%, 98%, or 99% monomer content at or greater than 3 months or more following preparation or storage. In some embodiments, stability of the conjugate is present if the conjugate displays less than 10% high molecular weight (HMW) species, such as less than 9%, 8%, 7%, 6%, 5%, 4%, 3%, 2%, or 1% HMW at 3 months or more following preparation or storage.

In some embodiments, potency or activity of the conjugate in the provided compositions can be measured by assessing the ED50 of the conjugate or by assessing the ability of the conjugate to induce or mediate PIT killing. In some embodiments, the conjugate displays greater than or greater than about 30% of the potency or activity, such as greater than or greater than about 40%, 50%, 60%, 70%, 80%, 90% or 95% of the potency or activity, at or greater than 3 months or more following storage compared to the conjugate prior to the storage, e.g., compared to a conjugate at t=0.

In some embodiments, compositions containing the stabilizing agent exhibit a larger percent recovery of the conjugate compared to the percent recovery of a conjugate contained in the composition lacking the stabilizing agent. In some embodiments, the recovery of the conjugate is greater than 90%, 91%, 92%, 93%, 94%, 95%, 96%, 97%, 98%, 99%, 99.5%, 99.9%, or 100% after exposure to sheer stress and/or agitation; after exposure to a pH less than or less than about pH 6.0; and/or after 3 months at a temperature greater than or greater than about 25° C.

In some embodiments, compositions containing the stabilizing agent exhibit a larger percentage of the conjugate in monomeric form compared to a composition lacking the stabilizing agent. In some embodiments, the percent of monomeric form of the conjugate in the composition is at least 90%, 91%, 92%, 93%, 94%, 95%, 96%, 97%, 98%, 99% after exposure to sheer stress and/or agitation; after exposure to a pH of less than or less than about pH 6.0; and/or after 3 months at a temperature greater than or greater than about 25° C.

In some embodiments, compositions containing the stabilizing agent exhibit a higher percentage of the conjugate contained in the main peak as determined by high performance liquid chromatography (HPLC), including size exclusion HPLC, as compared to a composition lacking the stabilizing agent. In some embodiments, the percent main peak of the conjugate as determined by HPLC is greater than 90%, 91%, 92%, 93%, 94%, 95%, 96%, 97%, 98%, or 99% after exposure to sheer stress and/or agitation; after exposure to a pH of less than or less than about pH 6.0; and/or after exposure for more than or about 3 months to a temperature greater than or greater than about 25° C.

In some embodiments, compositions containing the stabilizing agent retain more potency, activity, or purity after exposure to light, sheer stress and/or agitation, a pH of less than 6.0, or a temperature greater than about 25° C., as compared to a composition lacking the stabilizing agent. In some embodiments, the composition retains greater than or greater than about 30%, 40%, 50%, 60%, 70%, 80%, 90%, 91%, 92%, 93%, 94%, 95%, 96%, 97%, 98%, 99%, 99.5%, 99.9% or 100% of its potency, activity or purity after sheer stress and/or agitation; after exposure to a pH of less than or less than about pH 6.0; after exposure for more than or about 3 months to a temperature greater than or greater than about 25° C.

In some embodiments, a factor influencing the stability of the conjugate is protection of the conjugate from shear stress, and thus, shear stress-induced aggregation. Thus, in some embodiments, stability of the conjugated is imparted by protecting it from agitation. In some embodiments, the exposure to shear stress and/or agitation is caused by shaking. In some embodiments, the shaking is caused by mixing the composition, transporting the composition, dropping the composition, or other types of shaking or agitation. In some embodiments, the shaking comprises shaking on a machine configured to shake the composition, such as an orbital shaker, a vortexer, a platform shaker, or a pneumatic shaker.

In some embodiment, the shaking is at a speed greater than 25 rpm, greater than 50 rpm, greater than 75 rpm, greater than 100 rpm, greater than 125 rpm, greater than 150 rpm, greater than 175 rpm, greater than 200 rpm, greater than 225 rpm, greater than 250 rpm, greater than 275 rpm, or greater than 300 rpm.

In some embodiments, the shaking is carried out for a period of time is greater than 1 minute, greater than 5 minutes, greater than 10 minutes, greater than 15 minutes, greater than 20 minutes, greater than 25 minutes, greater than 30 minutes, greater than 45 minutes, greater than 60 minutes, greater than 90 minutes, greater than 120 minutes, greater than 150 minutes, greater than 180 minutes, greater than 210 minutes, greater than 240 minutes, greater than 270 minutes, greater than 300 minutes, greater than 330 minutes, greater than 360 minutes, greater than 390 minutes, greater than 420 minutes, greater than 450 minutes, greater than 480 minutes, greater than 510 minutes, greater than 540 minutes, greater than 570 minutes, or greater than 600 minutes.

In some embodiments, the exposure to shear stress and/or agitation is caused by freezing the composition and subsequently thawing the composition. Exemplary, non-limiting reasons why a composition undergoes a freeze-thaw cycle include storing the composition in one container and moving or aliquoting it into different containers; transporting or storing the composition with or without refrigeration or freezing, preparing individual or multiple doses of the composition over time; assessing the quality, purity, or potency of the composition, or combinations of these. In some embodiments, the composition undergoes one or more free-thaw cycles, including 2, 3, 4, 5, 6, 7, 8, 9, or 10 freeze thaw cycles.

In some embodiments, a factor influencing the stability of the conjugate is the protection of the conjugate from acidic conditions, such as a low pH. In some embodiments, the low pH is less than 6.0, such as less than or about 5.0, less than or about 4.0 or less than or about 3.0.

In some embodiments, a factor influencing the stability of the conjugate is protection of the conjugate from heat, and thus, heat-induced aggregation. Thus, in some embodiments, stability of the conjugated is imparted by protecting it from heat, or certain temperatures above 25° C. In some embodiments, the exposure to a temperature greater than 25° C. includes exposure to a temperature greater than or greater than about 30° C., 32° C., 35° C., 37° C., or 40° C. In some embodiments, the composition is exposed to one or more temperatures above 25° C. for more than three months, more than 4 months, more than five months, more than six months, more than nine months, more than 12 months, more than 18 months, or more than 24 months. In some embodiments, the composition is exposed to a temperature above 25° C. intermittently for a period of time as described above.

In some embodiments, the stability of the composition containing the conjugate is present after storage in a light protected container. In some embodiments, the composition containing the conjugate is protected from light using containers that protect contents from light, or certain wavelengths or intensities of light. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 500 nm and 725 nm, such as between or between about 650 nm and 725 nm, or does not transmit an intensity of light greater than 700 lux, 600 lux, 500 lux, 400 lux, 300 lux, 200 lux, or 100 lux. In some embodiments, the composition containing the conjugate is stored in a translucent or opaque container. In some embodiments, the container is green or amber. In some embodiments, the container is covered with an opaque substance, such as a foil, such as aluminum foil.

In some embodiments, the stability of the composition containing the conjugate is present following storage of the conjugate at a temperature less than or equal to or about 26° C., such as less than or equal to or about 20° C., 15° C., 8° C., 0° C., −20° C., or −80° C. In some embodiments, the temperature is from or from about 20 to 26° C., such as 23±3° C., or from or from about 2 to 8° C., such as 5±3° C., such as at or about 4° C. or at or about 5° C., or is less than 0° C., such as about −20 or −80° C.

In some embodiments, a stable composition containing the conjugate is provided that is stable for greater than 3 months, such as when manufactured and stored with a stabilizing agent as described above, under conditions of light protection as described above, and/or conditions of agitation as described, at a temperature less than 26° C., such as 2 to 8° C., and when formulated at a pH of greater than 6.0, such as a pH of 6.0 to 8.0.

D. Packaging of Compositions to Produce Drug Product

In some embodiments, the provided pharmaceutical compositions containing the phthalocyanine dye-antibody conjugate (e.g., ceuximab-IR700 conjugate), can be provided in one or more containers. In some embodiments, the container is a vial, a tube, a syringe, a bag, a pouch or a box or combinations thereof. In some embodiments, the container is a light protected container.

Also provided are articles of manufacture containing packaging materials, any pharmaceutical compositions or combinations provided herein, and a label that indicates that the compositions and combinations are to be used for treatment of a disease or condition, such as a cancer. Exemplary articles of manufacture are containers including single chamber and dual chamber containers. The containers include, but are not limited to, tubes, bottles, and syringes. The containers can further include a needle for subcutaneous administration.

In some embodiments, the compositions containing the conjugates are provided in a plurality of sealable containers. For example, the containers can each individually comprising a fraction of a single administration dose of a composition containing a conjugate that includes a phthalocyanine dye linked to an antibody. In some embodiments, the combined amount of the conjugate in the plurality of sealable containers is between or between about 100 mg and 1500 mg, or 100 mg and 1200 mg. In some embodiments, the combined amount of the conjugate in the plurality of sealable container is between or between about 100 mg and 500 mg, between or between about 200 mg and 400 mg, between or between about 500 mg and 1500 mg, between or between about 800 mg and 1200 mg or between or between about 1000 mg and 1500 mg.

In some embodiments, the article of manufacture contains packaging material and a label or package insert containing instructions for combining the contents of the plurality of vials to prepare a single dosage formulation of the composition.

In some embodiments, the compositions used for administration of agents, such as the phthalocyanine dye-antibody conjugate contain an effective amount of each agent along with conventional pharmaceutical carriers and excipients appropriate for the type of administration contemplated.

In some embodiments, a single dosage amount of the composition containing the agent, such as the phthalocyanine dye-antibody conjugate, is comprised within a single container, such as a container in which the agent is stored. In some embodiments, a single dosage amount of the composition containing the agent is comprised in a plurality of containers. Thus, in some embodiments, a plurality of containers, such as vials, are combined, in a container to be used for administration of the composition, such as an intravenous (IV) bag. In some embodiments, the container used for administration, such as IV bag, is prepared by opening one or a plurality of containers comprising the composition and placing the contents in the bag, such as until a desired dose of the agent for administration, e.g., infusion, is achieved.

Also provided are methods of preparing a composition that contains any of the conjugates described herein, or conjugates prepared using the methods provided herein, for administration, to a subject, such as any of the phthalocyanine dye-antibody conjugates (e.g., cetuximab-IR700 conjugate). In some embodiments, preparation of the composition for administration takes place under light-protected conditions. In some embodiments, the method of preparing the compositions for administration includes: unpacking one or more of any of the containers described herein or one or more of any of the packaging system described herein that includes any of the containers described herein; and transferring the composition present in the one or more containers into a device capable of administering the composition to a subject, wherein the only light to which the composition is exposed has a wavelength within a range from at or about 400 nm to at or about 650 nm, or the only light to which the composition is exposed has an intensity of less than 500 lux, such as less than 200 lux or less than 100 lux.

In some embodiments, the method of preparing the composition for administration to a subject is performed in a biosafety cabinet, biosafety hood or a sterile environment. In some embodiments, the one or more containers together comprise a therapeutically effective dose of the phthalocyanine-dye conjugate. In some embodiments, the one or more containers include at least or at least about or 2, 4, 6, 8, 10, 12, 18 or 24 containers.

In some embodiments, the provided method of preparing the composition containing the phthalocyanine-dye antibody conjugate (e.g., cetuximab-IR700 conjugate) for administration is carried out for no more than 1 hour, no more than 30 minutes or no more than 15 minutes; or the total exposure of the composition to any light during the method is no more than 500 lux hours, no more than 250 lux hours, no more than 100 lux hours, no more than 50 lux hours or no more than 25 lux hours.

Also provided are light-protected devices that include the provided compositions. In some embodiments, the light-protective device is used for administration of the compositions or conjugates described herein.

In some embodiments, the administration device is an intravenous infusion bag or a syringe. In some embodiments, the administration device comprises a light-protected cover capable of covering the device. In some embodiments, the light-protected cover protects from transmission of light having a wavelength from or from about 250 nm to at or about 800 nm, from about 250 nm to at or about 450 nm, from about 400 nm to at or about 800 nm, from about 450 nm to at or about 650 nm, or from about 600 nm to at or about 720 nm. In some embodiments, the light-protected cover protects from transmission of light such that the percentage of light transmission is less than at or about 50%, less than at or about 40%, less than at or about 30%, less than at or about 20%, less than at or about 10%, or less than at or about 5%. In some embodiments, the light-protected cover is green, blue, amber, translucent, opaque, or is covered by a material with light transmission of less than at or about 50%, less than at or about 40%, less than at or about 30%, less than at or about 20%, less than at or about 10%, or less than at or about 5%.

Also provided herein are containers, such as light-protected containers, and/or devices, such as light-protected devices, that contain any of the conjugates or compositions described provided herein. Also provided herein are packaging systems for protecting any of the conjugates or compositions described herein. In some embodiments, such packaging systems comprise one or more of the containers described herein.

Also provided are kits or articles of manufacture containing the provided container, device, and/or packaging system, for protection of the conjugates or compositions, and for storage and/or administration. The kit may include a container and/or packaging system, a light-protected cover capable of covering a device capable of administering a composition comprising a phthalocyanine dye-antibody conjugate. The kit, and optionally includes instructions for use. The kit can also contain a label or package insert on or associated with the contents of the kit. The kit or article of manufacture may further include a package insert indicating instructions for use, storage, or administration of the conjugate or composition contained in the container and/or packaging system.

In some embodiments, the conjugate composition is packaged into one or more containers, such as a light-protected container. In some embodiments, the container is a vial, such as a depyrogenated, glass vial. In some embodiments, the container, such as a vial, blocks light of a particular wavelength, such as a wavelength of light that is absorbed by the dye or dye-antibody conjugate. Thus, in some embodiments, the container protects the conjugate of the composition contained therein from light with a wavelength less than or less than about 250 nm or between or between about 550 nm and 750 nm. In some embodiments, the container protects from transmittance of light having a wavelength between or between about 500 nm and 725 nm, such as between or between about 650 nm and 725 nm. In some embodiments, the container only permits the transmittance of certain wavelengths of light, such as those from or from about 400 nm to 600 nm, such as from or from about 425 nm to 575 nm or from or from about 450 nm to 550 nm. In some embodiments, the container is green, blue, amber, translucent, opaque, or is wrapped in an opaque material, such as a foil, such as aluminum foil. In some embodiments, the container is sterile or depyrogenated. In some embodiments, the container protects from transmission of light such that the percentage of light transmission is less than 50%, less than 40%, less than 30%, less than 20%, less than 10% 10%, or less than 5%.

In some embodiments, the container has a maximum volume of at least or about 5 mL, at least or about 10 mL, at least or about 25 mL, at least or about 50 mL, such as 51±1 mL, at least or about 100 mL, at least or about 250 mL, at least or about 500 mL, or at least or about 1 L.

In some embodiments, such as where the containers are vials, the vials are stoppered and crimped prior to the fill. In some embodiments, the mean empty vial weight is determined and is used to determine the weigh range for filled vials.

In some embodiments, the packaging includes a semi-automated, aseptic fill. For example, in some embodiments, the conjugate composition is filled into the containers, e.g., vials, using a peristaltic pump and filling needle assembly. In some embodiments, the conjugate composition containing the conjugate is aseptically filtered prior to filling, such as through an about 0.2 µm filter, such as a 0.22 µm filter. In some embodiments, the sterile filtrate is weighed to determine the approximate number of containers, e.g., vials, to be filled.

In some embodiments, the method includes filling a vial with a volume amount of a provided dye-conjugate drug composition that is at least at or about 0.2 mL, 0.3 mL, 0.4 mL, 0.5 mL, 1 mL, 1.5 mL, 2.0 mL, 3.0 mL, 5.0 mL, 10.0 mL, 20.0 mL, 30.0 mL, 40.0 mL, 50.0 mL or more, such as generally 0.5 mL to 50 mL or 1 mL to 10 mL. In some embodiments, all vials that are filled are filled to contain the same volume and amount of the composition containing the dye conjugate. In some embodiments, the provided compositions can be provided in a plurality of vials, such as at least 2, 3, 4, 5, 6, 7, 8, 9, 10, 15, 20, 30, 40, 50 or more vials.

In some embodiments, a single dosage amount of the conjugate composition is contained in a single container. In some embodiments, a single dosage amount is provided in a plurality of containers, such as 2, 3, 4, 5, 6, 7, 8, 9, 10, or more containers.

In some embodiments, following the filling step, the containers, e.g., vials, are stoppered, sealed, and crimped. In some embodiments, the containers are stored protected from light, such as in a non-transparent bin, such as at a temperature less than or equal to or about 26° C., such as less than or equal to at or about 20° C., 15° C., 8° C., 0° C., −20° C., or −80° C. In some embodiments, the temperature is from or from about 20 to 26° C., such as 23±3° C., or from or from about 2 to 8° C., such as 5±3° C., such as at or about 4° C. or at or about 5° C., or less than 0° C., such as about −20 or −80° C.

In some embodiments, the containers, such as vials, are labeled. In some embodiments, labeling is performed at room temperature and care is taken to avoid the time of exposure of the conjugate to room temperature. For example, in some embodiments, the containers are exposed to ambient temperature for less than or about 30 minutes, such as less than or about 20 minutes, less than or about 10 minutes, less than or about 2 minutes, or less than or about 1 minute.

In some embodiments, the containers are further packaged to protect the contents from light. In some embodiments, a packaging system is provided that includes an internal packaging material comprising a container comprising the phthalocyanine dye-antibody conjugate (e.g., cetuximab-IR700 conjugate). In some embodiments, the internal packaging material has a light transmittance of less than 20%, such as less than 15%, less than 10%, less than 5%, or less than 1%. In some embodiments, the packaging system includes an external packaging material comprising the internal packaging material. In some embodiments, the external packaging material has a light transmittance of less than 20%, such as less than 15%, less than 10%, less than 5%, or less than 1%. In some embodiments, the internal or external packaging material includes an opaque foil, such as aluminum foil. In some embodiments, the container is covered by material with light transmission of less than at or about 50%, less than at or about 40%, less than at or about 30%, less than at or about 20%, less than at or about 10%, or less than at or about 5%. In some embodiments, the secondary packaging material is an aluminum pouch. In some embodiments, the external packaging material comprises cardboard.

In some embodiments, the internal and/or external packaging material is suitable for storage of the conjugate composition. In some embodiments, the internal and/or external packaging material is suitable for shipping of the conjugate composition.

Also provided is a packaging system for protecting a composition containing a phthalocyanine dye-antibody conjugate from light that includes one or more containers, such as one, two, three, or more containers. Each or all of the containers in the packaging system provided herein can be light-protected containers, such as any light-protected containers described herein.

In some embodiments, the packaging system includes two containers: a first container comprising any of the containers described herein, and a second container comprising the first container, wherein the second container protects from transmission of light having a wavelength from or from about 250 nm to or to about 800 nm, from about 250 nm to or to about 450 nm, from about 400 nm to or to about 800 nm, from about 450 nm to or to about 650 nm, or from about 600 nm to or to about 720 nm.

In some embodiments, the second container protects from transmission of light such that the percentage of light transmission is light transmission of less than at or about 50%, less than at or about 40%, less than at or about 30%, less than at or about 20%, less than at or about 10%, or less than at or about 5%. In some embodiments, the second container is green, blue, amber, translucent, opaque, or is covered by a material with light transmission of less than at or about 50%, less than at or about 40%, less than at or about 30%, less than at or about 20%, less than at or about 10%, or less than at or about 5%. In some embodiments, the first and second containers are independently selected from among a vial, a tube, a syringe, a bag, a pouch, and a box.

In some embodiments, any of the provided packaging system further includes a third container comprising the second container, wherein the third container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the third container protects from transmission of light such that the percentage of light transmission is less than at or about 50%, less than at or about 40%, less than at or about 30%, less than at or about 20%, less than at or about 10%, or less than at or about 5%. In some embodiments, the third container is green, blue, amber, translucent, opaque, or is covered by a material with light transmission of less than at or about 50%, less than at or about 40%, less than at or about 30%, less than at or about 20%, less than at or about 10%, or less than at or about 5%. In some embodiments, the third container is selected from among a vial, a tube, a syringe, a bag, a pouch, and a box.

In some embodiments, the containers or containers or packaging systems comprising the composition containing the conjugate, such as a single container or plurality of containers comprising a single dosage amount, are packaged in a kit. Thus, in some embodiments, the kit includes one or more single dosage amount. In some embodiments, the kit includes instructions, such as for administering the conjugate, such as under light-protected conditions. In some embodiments, the kit contains materials to be used for light protection of the conjugate, such as opaque foil, opaque containers, opaque intravenous (IV) bags, or opaque sleeves, such as for covering the IV bag.

For example, in some embodiments, the kit includes any of the containers described herein or any of the packaging systems described herein; a light-protected cover capable of covering a device capable of administering a composition comprising a phthalocyanine dye-antibody conjugate; and optionally instructions for use. In some embodiments, the administration device is an intravenous infusion bag or a syringe. In some embodiments, the light-protected cover protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the light-protected cover protects from transmission of light such that the percentage of light transmission is less than at or about 50%, less than at or about 40%, less than at or about 30%, less than at or about 20%, less than at or about 10%, or less than at or about 5%. In some embodiments, the light-protected cover is green, blue, amber, translucent, opaque, or is covered by a material with light transmission of less than at or about 50%, less than at or about 40%, less than at or about 30%, less than at or about 20%, less than at or about 10%, or less than at or about 5%.

In some embodiments, prior to, during, and following the preparation (e.g., conjugation), manufacturing or production, formulation and/or packaging of the composition containing the conjugate, the conjugate composition is protected from environmental light, such as light in the red light range. In some embodiments, the only light to which the dye and conjugate are exposed prior to, during, and following the preparation (e.g., conjugation), manufacturing or production, formulation and/or packaging of the composition is green light. In some embodiments, the only light to which the dye and conjugate are exposed prior to, during, and following the preparation (e.g., conjugation), manufacturing or production, formulation and/or packaging of the composition has a wavelength in a range from at or about 400 nm to at or about 600 nm, such as from at or about 425 nm to at or about 575 nm or from at or about 450 nm to at or about 550 nm. In some embodiments, the only light to which the dye and conjugate are exposed prior to, during, and following the preparation (e.g., conjugation), manufacturing or production, formulation and/or packaging of the composition has a wavelength that is not absorbed by the dye or is not substantially absorbed by the dye.

In some embodiments, prior to, during, and following the preparation (e.g., conjugation), manufacturing or production, formulation and/or packaging of the composition, the dye and conjugate are not exposed to any environmental light or are not exposed to light with an intensity greater than 700 lux, greater than 600 lux, greater than 500 lux, greater than 400 lux, greater than 300 lux, greater than 200 lux, or greater than 100 lux. In some embodiments, the total exposure of the dye and/or conjugate in the composition to any light during the preparation (e.g., conjugation), manufacturing or production, formulation and/or packaging is for no more than 5000 lux hours, no more than 2500 lux hours, no more than 1000 lux hours, no more than 500 lux hours, no more than 250 lux hours, no more than 100 lux hours or no more than 80 lux hours, no more than 50 lux hours or no more than 25 lux hours.

III. METHODS OF TREATMENT

In some embodiments, provided are methods for using and uses of the provided compositions containing a phthalocyanine dye-antibody conjugate that targets to a cell or pathogen associated with a disease or condition, such as via binding to a cell surface molecule, cell surface protein or cell surface receptor expressed on a cell. Among the provided methods are methods for using and uses of the provided compositions containing cetuximab-IR700 conjugate. Such methods and uses include therapeutic methods and uses, for example, involving administration of the molecules to a subject having a disease, condition, or disorder followed by irradiation to achieve photoimmunotherapy, thereby resulting in photolysis of such cells or pathogens to effect treatment of the disease or disorder. Uses include uses of the conjugates in such methods and treatments, and in the preparation of a medicament in order to carry out such therapeutic methods. In some embodiments, provided are methods for using and uses of such molecules for treating a tumor in a subject with a phthalocyanine dye-antibody conjugate (e.g., cetuximab-IR700 conjugate) to treat a tumor in a subject. In some embodiments, the phthalocyanine-antibody molecule conjugate is a stable conjugate, such as any described herein. In some embodiments, the phthalocyanine dye-antibody conjugate is produced using the methods as described herein. In some embodiments, the methods thereby treat the disease or condition or disorder in the subject.

In some embodiments, the treatment methods include administration of a provided composition containing phthalocyanine dye-antibody conjugate to the subject under conditions in which, generally, a cell targeted for killing is contacted with the conjugate. In some embodiments, the methods result in the binding of the antibody (e.g., cetuximab) portion of the conjugate to a cell surface protein associated with a tumor or cancer. After contacting or administering the conjugate, a local area of the subject containing the targeted cells, e.g., the tumor, is exposed or irradiated with light absorbed by the dye, thereby activating the conjugate to effect specific cell killing. For example, in some embodiments, the methods further include local irradiation of the disease region in the subject, such as local irradiation of the tumor. In some embodiments, irradiation is performed at a wavelength of 600 to 850 nm at a dose of at least 1 J cm$^{-2}$. In some embodiments, the conjugate is targeted to the diseased cell, such as tumor, and the irradiation results in cell killing, such as by photoimmunotherapy (PIT). In some embodiments, the methods include methods described in U.S. Pat. No. 8,524,239 or U.S. Publication No. US2014/0120119.

In some embodiments, administration of the provided compositions containing the conjugate takes place under light-protected conditions. In some embodiments, the administration is performed under fluorescent lighting or LED lighting. In some embodiments, the administration is performed in the absence of direct or indirect sunlight.

In some embodiments, prior to and during administration, the composition containing the conjugate is not exposed to environmental light or is not exposed to environmental light with an intensity greater than 700 lux, greater than 600 lux, greater than 500 lux, greater than 400 lux, greater than 300 lux, greater than 200 lux, or greater than 100 lux or greater than 50 lux.

In some embodiments, the composition containing the conjugate is not exposed to light with an intensity of greater than 700 lux, greater than 600 lux, greater than 500 lux, greater than 400 lux, greater than 300 lux, greater than 200 lux, or greater than 100 lux or greater than 50 lux for more than 20 minutes, 10 minutes, or for more than 5 minutes. In some embodiments, the dye and/or conjugate is not exposed to light with an intensity of greater than 200 lux for more than 10 minutes, or for more than 5 minutes. In some embodiments, prior to and during administration, any exposure of the conjugate to light is for less than 20 minutes, less than 15 minutes, less than 10 minute, less than 5 minutes, less than 4 minutes, less than 3 minutes, less than 2 minutes, or less than 1 minute. In some embodiments, the total exposure of the dye and/or conjugate to any light prior to or during administration is for no more than 5000 lux hours, no more than 2500 lux hours, no more than 1000 lux hours, no more than 500 lux hours, no more than 250 lux hours, no more than 100 lux hours or no more than 80 lux hours, no more than 50 lux hours or no more than 25 lux hours.

In some embodiments, the composition containing the conjugate is protected from environmental light, such as light in red light range. In some embodiments, the only light to which the conjugate is exposed has a wavelength that is not absorbed by the conjugate or is not substantially absorbed by the conjugate.

In some embodiments, the prior to administration to the subject, the composition containing the conjugate is protected from light using containers that protect contents from light, or certain wavelengths or intensities of light. The container can be a tube, syringe, infusion bag or other container that is compatible with injection of transfer of the conjugate to the subject. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 500 nm and at or about 725 nm, such as between or between about 650 nm and at or about 725 nm, or does not transmit an intensity of light greater than at or about 700 lux, 600 lux, 500 lux, 400 lux, 300 lux, 200 lux, or 100 lux. In some embodiments, the conjugate is administered from or in a translucent or opaque container. In some embodiments, the container is green or amber. In some embodiments, the container is covered with an opaque substance, such as a foil, such as aluminum foil. In some embodiments, the container is an intravenous (IV) bag and the bag is covered in an opaque sleeve, such as foil, such as aluminum foil.

The target cell can be a cell that is not desired or whose growth is not desired, such as a tumor cell. In some embodiments, the cells can be growing in culture, or present in a mammal to be treated, such as a subject with cancer. Any target cell can be treated with the provided compositions. In some embodiments, the target cell expresses a cell surface protein that is not substantially found on the surface of other normal cells. In some embodiments, an antibody can be selected that specifically binds to such protein and a phthalocyanine dye-antibody conjugate may be generated for that protein. In some embodiments, the cell surface protein is a tumor-specific protein. In some embodiments, the cell surface protein is CD25, which can be used to target cells associated with undesired transplant rejection.

Also provided are methods of removing unwanted cells or pathogens, such as a diseased cell, or a pathogen infected cell, from a subject, using any of the compositions containing a conjugate described herein. For example, in some embodiments, unwanted cells can include a stem cell, a proliferating cell, a cell in a hyperplasia, an inflammatory cell, a negative regulatory immune cell, which optionally is a T cell, a pathogen infected cell, a neuron, a fat cell or adipocyte. In some embodiments, the unwanted cell is a cancer cell or a tumor cell. In some embodiments, the unwanted cell is a cancer stem cell or a circulating tumor cell or a cell present in the tumor microenvironment. In some embodiments, the unwanted pathogen can be a virus, a bacterial cell, or a fungal cell.

In some embodiments, provided are methods of removing unwanted cells or pathogens, such as a diseased cell, or a pathogen infected cell, from a sample, using any of the compositions containing a conjugate described herein. For example, the unwanted cells or pathogens are removed from a biological sample from a subject, such as a blood sample or bone marrow sample or a biopsy. In some embodiments, the sample is a blood sample or a tissue sample. In some embodiments, the unwanted cells or pathogens are removed from a tissue, such as a tissue temporarily removed from a subject during surgery or treatment. In some embodiments, the unwanted cells are removed from a sample associated with a device, such as a biofilm on medical devices.

In some embodiments, the irradiation for removal or treatment is effected in vivo, e.g., administered directly to the subject. In some embodiments, the method is performed in vitro, or ex vivo, e.g., outside of the body of the subject. In some embodiments, the method is performed using an extracorporeal device. Exemplary extracorporeal devices include devices used for hemodialysis, extracorporeal oxygenation, $CO_2$ removal, and apheresis, or instruments that receive blood removed from a subject, processes (e.g., filters, purifies, treats, administers therapeutic agents to, etc.) the blood, and then returns the blood to the subject.

In some embodiments of the methods provided herein, removal of unwanted cells or pathogens from a sample, such as a blood sample or a tissue sample, include methods for treatment, such as treatment of a hyperplasia, a tumor or an infection.

In some embodiments, the unwanted cell is associated with, causes or contributes to the etiology of a disease or condition. In some embodiments, the disease of condition is a tumor or cancer, an infection, an inflammatory disease or condition, or a neuronal disease or condition. In some embodiments, the cell is a neuron and the disease or condition is a neurological disorder, which optionally is pain; the cell is a fat cell or adipocyte and the disease or condition involves excess fat; the cell is a pathogen infected cell and the disease or condition is an infection; the cell is a pathogen and the disease or condition is an infection; the cell is an inflammatory cell and the disease or condition is an inflammatory disease; the cell is a an immune cell, which optionally is a regulatory T cell, and the disease or condition is a tumor or cancer; or the cell is a tumor or cancer cell and the disease or condition is a tumor or a cancer. In some embodiments, the cell is present in the microenvironment of a lesion associated with a disease or condition or is in a hyperplasia. In some embodiments, the lesion is a tumor and the disease or condition is a tumor or cancer. In some embodiments, the cell is present in the microenvironment of a tumor. In some embodiments, the method treats the disease or condition.

The methods generally include administering to a subject compositions containing a conjugate as provided herein, and irradiating the unwanted cells or pathogens to activate the conjugate and thereby removing the cells.

In some embodiments, the method of removing unwanted cells or pathogens in a subject includes: (a) administering a composition comprising a phthalocyanine-dye conjugate from any of the light-protected device provided herein to a subject, wherein prior to and during the administration step the composition is not exposed to an intensity of environmental light greater than 500 lux; and (b) irradiating the unwanted cells or pathogens at a wavelength of 660 to 740 nm at a dose of at least 1 J $cm^{-2}$ or 1 J/cm of fiber length thereby removing the unwanted cell in the subject.

In some embodiments, the method of removing unwanted cells or pathogens in a subject includes: a) administering to a subject a therapeutically effective amount of any of the compositions containing a conjugate described herein, wherein prior to and during the administration step the conjugate is not exposed to an intensity of environmental light greater than 500 lux; and b) irradiating the unwanted cells or pathogens at a wavelength of 660 to 740 nm at a dose of at least 1 J $cm^{-2}$ or 1 J/cm of fiber length thereby removing the unwanted cell in the subject.

In some embodiments, the method of removing unwanted cells or pathogens in a subject includes: a) administering to a subject a therapeutically effective amount of a composition containing a conjugate comprising IR700 linked to an antibody capable of binding an unwanted cell or pathogen, wherein prior to and during the administration step the conjugate is not exposed to an intensity of environmental light greater than 500 lux; and b) irradiating the unwanted cells or pathogens at a wavelength of 600 to 800 nm at a dose of at least 1 J $cm^{-2}$ or 1 J/cm of fiber length thereby removing the unwanted cells or pathogens in the subject.

In some embodiments, the method includes removing or killing unwanted cells, where the unwanted cells are tumor cells. In some embodiments, the conjugate used in such methods is antibody-IR700 conjugate. In some embodiments, the conjugate used in such methods is cetuximab-IR700 conjugate. In some embodiments, the conjugate used in such methods is cetuximab-IR700 conjugate formulated as a composition that includes one or more stabilizing agents in an amount effective to reduce or prevent aggregation of the conjugate, wherein the one or more stabilizing agents include a surfactant, such as a non-ionic surfactant or a zwitterionic surfactant, and/or a protectant.

In some embodiments, the one or more stabilizing agents comprised in the compositions used in the methods include a surfactant, such as a non-ionic surfactant. In some embodiments, the non-ionic surfactant is a polysorbate, a lecithin, a polyethylene glycol (PEG), a polyoxyethylene glycol sorbitan alkyl ester, a polyethylene glycol octylphenyl ether, a block copolymer of polyethylene glycol and polypropylene glycol, a polyethylene glycol alkyl ether, or combinations thereof.

In some embodiments, the polyoxyethylene glycol sorbitan alkyl ester is a polysorbate, such as a polysorbate 20, polysorbate 40, polysorbate 60, polysorbate 80, or combinations thereof. In some embodiments, the polysorbate is polysorbate 20. In some embodiments, the polysorbate is polysorbate 80. In some embodiments, the polyethylene glycol octylphenyl ether includes polyethylene glycol p-(1,1,3,3-tetramethylbutyl)-phenyl ether (Triton X-100®). In some embodiments, the block copolymer of polyethylene glycol and polypropylene glycol includes polyoxyethylene-polyoxypropylene block copolymer (Pluronic® F-68), poly (ethylene glycol)-block-poly (propylene glycol)-block-poly (ethylene glycol) (Pluronic® L-121), poloxamer 407 (Pluronic® F127), or combinations thereof. In some embodiments, the polyethylene glycol alkyl ether includes polyethylene glycol dodecyl ether (Brij® 35).

In some embodiments, the surfactant, e.g., non-ionic surfactant or a zwitterionic surfactant comprised in the compositions used in the methods is present at a percentage by volume (w/v) of at least or at least about 0.001%, 0.002%, 0.005%, 0.010%, 0.020%, 0.030%, 0.035%, 0.04%, 0.045%, 0.05%, 0.055%, 0.060%, 0.065%, 0.070%, 0.075%, 0.080%, 0.085%, 0.090%, 0.095%, or 0.100%. In some embodiments, the surfactant, e.g., non-ionic surfactant or a zwitterionic surfactant, is present at a percentage by weight to volume (w/v) of between 0.001% and 0.10%, between 0.001% and 0.075%, between 0.001% and 0.05%, between 0.001% and 0.01%, between 0.001% and 0.005%, 0.005% and 0.10%, between 0.005% and 0.075%, between 0.005% and 0.05%, between 0.005% and 0.01%, between 0.01% and 0.10%, between 0.01% and 0.075%, between 0.01% and 0.05%, between 0.05% and 0.1%, between 0.05% and 0.075% and between 0.075% and 0.10%, each inclusive. In some embodiments, the surfactant, e.g., non-ionic surfactant or a zwitterionic surfactant, is present at a percentage by weight to volume (w/v) of at least or at least about 0.02%, 0.03%, 0.04%, or 0.05%. In some embodiments, the surfactant, e.g., non-ionic surfactant or a zwitterionic surfactant is present at a percentage by weight to volume (w/v) of between 0.02% and 0.06%, 0.02% and 0.05%, between 0.02% and 0.04%, between 0.02% and 0.03%, between 0.03% and 0.06%, between 0.03% and 0.05%, between 0.03% and 0.04%, between 0.04% and 0.06%, between 0.04% and 0.05%, between 0.05% and 0.06%, each inclusive.

In some embodiments, the one or more stabilizing agents comprised in the compositions used in the methods include a protectant such as a tonicity agent. In some embodiments, the protectant is trehalose, sorbitol, sucrose, mannitol, xylitol or glycerol. In some embodiments, the protectant is present at a percentage by weight to volume (w/v) of between 1% and 20%, between 1% and 5%, between 1% and 10%, between 8% and 10%, and between 5% and 9%. In some embodiments, the protectant is present at a percentage by weight to volume (w/v) at or at about 5%, 6%, 7%, 8%, 9%, 10%, 11% 12%, 13%, 14% or 15%. In some embodiments, the one or more stabilizing agents include a protectant and a surfactant, e.g., a non-ionic surfactant or a zwitterionic surfactant.

In some embodiments, the subject to be treated, or the subject where unwanted cells or pathogens are removed, has a tumor, and the phthalocyanine dye-antibody conjugate is targeted to a pre-cancerous lesion or a tumor. In some embodiments, the tumor is a cancer. In some embodiments, the cancer is a cancer of the head and neck, breast, liver, colon, ovary, prostate, pancreas, brain, cervix, bone, skin, lung, or blood. In some embodiments, cancer may include a malignant tumor characterized by abnormal or uncontrolled cell growth. Other features that may be associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. Metastatic disease may refer to cancer cells that have left the original tumor site and migrated to other parts of the body, for example via the bloodstream or lymph system. In some embodiments, a cell targeted by the disclosed methods is a cancer cell. In some embodiments, the targeted cell is a cancer stem cell or a circulating tumor cell.

In some embodiments, the conjugate is targeted to a protein expressed in the tumor. In some embodiments, the protein on the cell surface of the target cell to be targeted is not present in significant amounts on other cells. For example, the cell surface protein can be a receptor that is only found on the target cell type.

In some embodiments, the protein expressed in the tumor, e.g., tumor-specific protein. In some embodiments, the cell surface protein is a tumor-specific protein or tumor-specific antigen, such as members of the EGF receptor family (e.g., HER1, 2, 3, and 4). In some embodiments, tumor specific proteins are those proteins that are unique to cancer cells or are much more abundant on them, as compared to other cells, such as normal cells. For example, HER2 is generally found in breast cancers, while HER1 is typically found in adenocarcinomas, which can be found in many organs, such as the pancreas, breast, prostate, and colon.

In some embodiments, the method includes treating a pre-cancerous lesion or cancer with the formulated cetuximab-IR700 conjugate such as a cancer that where the cancer expresses epidermal growth factor receptor (EGFR or HER1) antigens. Such cancers may include, but are not limited to, head and neck cancer, pre-malignant dysplasia, glioblastoma, esophageal cancer, laryngeal cancer, medullary thyroid cancer, non-melanoma cutaneous SCC, breast cancer, non-small cell lung cancer (NSCLC), stomach cancer, colorectal cancer, kidney cancer, bladder cancer, pancreatic cancer, ovarian cancer, endometrial cancer, cervical cancer, vulvar cancer, prostate cancer, penile cancer, testicular cancer and anal cancer.

In some embodiments, the method includes treating a cancer with the formulated conjugate such as a head or neck cancer. In some embodiments, the method of treating unwanted cells from a head or neck cancer in a subject includes: (a) administering a composition comprising a cetuximab-IR700 conjugate to a subject, and (b) irradiating the unwanted cells at a wavelength of 660 to 740 nm at a dose of at least 1 J $cm^{-2}$ or 1 J/cm of fiber length thereby removing or killing the unwanted cell in the subject. In some embodiments, the method includes administering the cetuximab-IR700 conjugate from any of the light-protected device provided herein and/or wherein prior to and during the administration step the composition is not exposed to an intensity of environmental light greater than 500 lux. In some embodiments, the irradiation is performed at 690 nm or at 690 nm±50 nm.

In some embodiments the method of treating a head or neck cancer in a subject includes: (a) intravenously administering to a subject having a head or neck cancer a formulated composition comprising a cetuximab-IR700 conjugate wherein the conjugate is administered in an amount that is or is about 640 mg/m$^2$; and b) after administering the conjugate, irradiating the lesion at a wavelength of 690±20 nm at a dose of at least or at least about or about 50 J $cm^{-2}$ or 100 J/cm of fiber length, thereby treating the cancer in the subject. In some embodiments of the method, light illumination is administered for irradiating the lesion at or at about 20, 21, 22, 23, 24, 25, 26, 27, 28, 29, 30, 31, or 32 hours following the administration of the cetuximab-IR700. In some embodiments of the method, light illumination is administered for irradiating the lesion at or at about 20±4 hours following the administration of the cetuximab-IR700. In some embodiments of the method, light illumination is administered for irradiating the lesion at or at about 24±4 hours following the administration of the cetuximab-IR700. In some embodiments of the method, light illumination is administered for irradiating the lesion at or at about 24±3 hours following the administration of the cetuximab-IR700.

In some embodiments of the method, the cetuximab-IR700 conjugate to be administered is formulated in a composition comprising a non-ionic surfactant and/or a protectant. In some embodiments, cetuximab-IR700 conjugate is formulated in a composition comprising a polysorbate and optionally a protectant such as trehalose, sorbitol, xylitol, mannitol, or sucrose. In some embodiments, cetuximab-IR700 conjugate is formulated in a composition comprising a polysorbate and trehalose. In some embodiments, cetuximab-IR700 conjugate is formulated in a composition comprising polysorbate 80 and trehalose. In some embodiments, cetuximab-IR700 conjugate is formulated in a composition comprising 10 mM sodium phosphate, 0.02% (w/v) polysorbate 80 and 9% (w/v) trehalose at pH 7.1.

In some embodiments, the subject is a human or non-human mammal. In some embodiments, the subject is a human or veterinary subject, such as a mouse. In some embodiments, the subject is a mammal, such as a human, who has cancer, or is being treated for cancer. In some embodiments the disclosed compositions are used to treat a subject who has a tumor, such as a tumor described herein. In some embodiments, the tumor has been previously treated, such as surgically or chemically removed, and the disclosed compositions are used subsequently to kill any remaining undesired tumor cells that may remain in the subject.

The disclosed compositions containing a conjugate can be used to treat any mammalian subject, such as a human, who has a tumor, such as a cancer, or has had such previously removed or treated. Subjects in need of the disclosed therapies can include human subjects having cancer, wherein the cancer cells express a tumor-specific protein on their surface that can specifically bind to phthalocyanine dye-antibody conjugate. For example, the disclosed compositions can be used as initial treatment for cancer either alone, or in combination with radiation or other chemotherapy. The disclosed compositions can also be used in patients who have failed previous radiation or chemotherapy. Thus, in some embodiments, the subject is one who has received other therapies, but those other therapies have not provided a desired therapeutic response. The disclosed compositions can also be used in patients with localized and/or metastatic cancer.

In some embodiments, the method includes selecting a subject that will benefit from the disclosed therapies and compositions, such as selecting a subject having a tumor that expresses a cell surface protein, such as a tumor-specific protein, that can specifically bind to a phthalocyanine dye-antibody conjugate. For example, if the subject is determined to have a breast cancer that expresses HER1, the subject may be selected to be treated with an anti-HER1-IR700 molecule, such as cetuximab-IR700. In some embodiments, the subject is determined to have a head and neck cancer that expressed HER1, the subject may be selected to be treated with an anti-HER 1 antibody-phthalocyanine dye conjugate (e.g., anti-HER1 antibody-IR700 conjugate such as cetuximab-IR700). In some embodiments, the method includes administering to a subject a therapeutically effective amount of the compositions containing a conjugate drug product. In some embodiments, the method includes administering to a subject a therapeutically effective amount of a conjugate containing a dye conjugated to an antibody, e.g., an antibody-IR700 conjugate such as for example, cetuximab-IR700. In some embodiments, the antibody-IR700 conjugate is targeted to the tumor.

In some embodiments, a therapeutically effective amount is an amount of a composition that when activated with light treatment, or together with an additional therapeutic agent, such as a chemotherapeutic agent, is sufficient to achieve a desired effect in a subject, or in a cell, being treated with the composition. The effective amount of the therapeutic agent, such as the phthalocyanine dye-antibody conjugate, can be dependent on several factors, including, but not limited to the subject or cells being treated, the particular therapeutic agent, and the manner of administration of the therapeutic composition. In some embodiments, a therapeutically effective amount or concentration is one that is sufficient to prevent advancement, such as metastasis, delay progression, or to cause regression of a disease, or which is capable of reducing symptoms caused by the disease, such as cancer. In some embodiments, a therapeutically effective amount or concentration is one that is sufficient to increase the survival time of a patient with a tumor.

In some embodiments, a desired response of treatment using the compositions described herein is to reduce or inhibit one or more symptoms associated with pre-cancer or cancer. In some embodiments, the one or more symptoms do not have to be completely eliminated for the composition to be effective. For example, administration of a composition containing the phthalocyanine dye-antibody conjugate followed by irradiation can decrease the size of a tumor, such as the volume or weight of a tumor, or metastasis of a tumor, for example by at least 20%, at least 50%, at least 80%, at least 90%, at least 95%, at least 98%, or at least 100%, as compared to the tumor size, volume, weight, or metastasis in the absence of the conjugate.

In some embodiments, a desired response of treatment according to the provided methods is to kill a population of cells by a desired amount, for example by killing at least 20%, at least 50%, at least 60%, at least 70%, at least 80%, at least 90%, at least 95%, at least 98%, or at least 100% of the cells, as compared to cell killing in the absence of the conjugate and irradiation. In some embodiments, a desired response is to increase the survival time of a patient with a tumor, or who has had a tumor recently removed, by a desired amount, for example to increase survival by at least 20%, at least 50%, at least 60%, at least 70%, at least 80%, at least 90%, at least 95%, at least 98%, or at least 100%, as compared to the survival time in the absence of the conjugate and irradiation.

The amount of composition containing an agent that includes the phthalocyanine dye-antibody conjugate that is administered to a human or veterinary subject will vary depending upon a number of factors associated with that subject, for example the overall health of the subject. In some embodiments, an effective amount of the composition can be determined by varying the dosage of the product and measuring the resulting therapeutic response, such as the regression of a tumor. In some embodiments, effective amounts can be determined through various in vitro, in vivo, or in situ immunoassays. In some embodiments, the disclosed compositions can be administered in a single dose, or in several doses, as needed to obtain the desired response. In some embodiments, the effective amount is dependent on the source applied, the subject being treated, the severity and type of the condition being treated, and the manner of administration.

In some embodiments, a therapeutically effective amount of the composition includes a dose of the conjugate that is at least at or about 0.5 milligram per 60 kilogram (mg/kg), at least at or about 5 mg/60 kg, at least at or about 10 mg/60 kg, at least at or about 20 mg/60 kg, at least at or about 30 mg/60 kg, at least at or about 50 mg/60 kg, for example between at or about 0.5 and at or about 50 mg/60 kg, such as a dose of 1 mg/60 kg, 2 mg/60 kg, 5 mg/60 kg, 20 mg/60 kg, or 50 mg/60 kg, for example when administered intravenously. In some embodiments, the dose of the conjugate is at least at or about 10 µg/kg, such as at least at or about 100 µg/kg, at least at or about 500 µg/kg, or at least at or about 500 g/kg, for example between at or about 10 µg/kg and at or about 1000 µg/kg, such as a dose of at or about 100 µg/kg, 250 µg/kg, about 500 µg/kg, 750 µg/kg, or 1000 µg/kg, for example when administered intratumorally or IP. In some embodiments, the dose is at least at or about 1 µg/ml, such as at least at or about 500 µg/ml, such as between at or about 20 µg/ml and at or about 100 µg/ml, such as at or about 10 µg/ml, 20 µg/ml, 30 µg/ml, 40 µg/ml, 50 µg/ml, 60 µg/ml, 70 µg/ml, 80 µg/ml, 90 µg/ml or 100 µg/ml, for example administered in topical solution.

In some embodiments, a therapeutically effective amount of the composition includes a dose of the conjugate that is between or between about 10 mg/m$^2$ and at or about 2000 mg/m$^2$, such as between or between about 10 mg/m$^2$ and at or about 1500 mg/m$^2$. between at or about 25 mg/m$^2$ and at or about 2000 mg/m$^2$. between at or about 200 mg/m$^2$ and at or about 1250 mg/m$^2$. between at or about 500 mg/m$^2$ and at or about 1250 mg/m$^2$. between at or about 500 mg/m$^2$ and at or about 750 mg/m$^2$. between at or about or 750 mg/m$^2$ and at or about 1250 mg/m$^2$. In some embodiments, a therapeutically effective amount of the composition includes a dose of the conjugate that is or is about 600 mg/m², 610 mg/m², 620 mg/m², 630 mg/m², 640 mg/m², 650 mg/m², 660 mg/m², 670 mg/m², 680 mg/m², 690 mg/m², or 700 mg/m². In some embodiments, a therapeutically effective amount of the composition includes a dose of the conjugate that is or of about 100 mg/m², 160 mg/m², 320 mg/m², 400 mg/m², 450 mg/m², 500 mg/m², 600 mg/m², 640 mg/m², or 1280 mg/m². In some embodiments, the therapeutically effective amount of the composition includes a dose of the conjugate that is at or about 640 mg/m².

In some embodiments, the therapeutically effective amount is at least or at least about 0.01 mg, 0.1 mg, 0.5 mg, 1 mg, 5 mg, 10 mg, 50 mg, 100 mg, 200 mg, 500 mg, 600 mg, 700 mg, 800 mg, 900 mg, 1000 mg, 2000 mg, 3000 mg or more.

One skilled in the art will recognize that higher or lower dosages also could be used, for example depending on the particular conjugate. In some embodiments, dosages, such as daily dosages, are administered in one or more divided doses, such as 2, 3, or 4 doses, or in a single formulation. The disclosed conjugate can be administered alone, in the presence of a pharmaceutically acceptable carrier, or in the presence of other therapeutic agents, such as other antineoplastic agents.

In some embodiments, prior to administration of the composition containing the conjugate, the subject is administered the antibody alone in a form that is non-conjugated, such as cetuximab. Generally, the antibody that is administered prior to the composition containing the conjugate is the same antibody that will be administered as part of the conjugate. In some embodiments, the dose of antibody administered is between or between about 10 mg/m² and 2000 mg/m², such as between or between about 10 mg/m² and 1500 mg/m², 25 mg/m² and 2000 mg/m², 200 mg/m² and 1250 mg/m², 500 mg/m² and 1250 mg/m², 500 mg/m² and 750 mg/m², or 25 mg/m² and 100 mg/m².

In some embodiments, the composition containing the antibody is administered at least 1 week, at least 6 days, at least 5 days, at least 96 hours, at least 72 hours, at least 48 hours, at least 24 hours, or at least 12 hours prior to administration of the conjugate. In some embodiments, the composition containing the antibody is administered within a range from or from about 1 hour to 1 week prior to administration of the conjugate, such as within a range from or from about 1 hour to 96 hours, 1 hour to 48 hours, 1 hour to 24 hours, 24 hours to 96 hours, or 24 hours to 48 hours. In some embodiments, the composition containing the antibody is administered at or about 96 hours prior to the administration of the conjugate.

In some embodiments, the composition containing the conjugate may be administered either systemically or locally to the organ or tissue to be treated. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes. In some embodiments, the composition containing the conjugate is administered intravenously. In some embodiments, the composition containing the conjugate is administered parenterally. In some embodiments, the composition containing the conjugate is administered enterally. In some embodiments, the composition containing the conjugate is administered by local injection. In some embodiments, the composition containing the conjugate is administered as a topical application.

The composition comprising the conjugate can be administered locally or systemically using any method known in the art, for example to subjects having a tumor, such as a cancer, or who has had a tumor previously removed, for example via surgery. Although specific examples are provided, one skilled in the art will appreciate that alternative methods of administration of the disclosed conjugate can be used. Such methods may include for example, the use of catheters or implantable pumps to provide continuous infusion over a period of several hours to several days into the subject in need of treatment.

In some embodiments, the composition containing the conjugate is administered by parenteral means, including direct injection direct injection or infusion into a tumor, such as intratumorally. In some embodiments, the composition containing the conjugate is administered to the tumor by applying the conjugate to the tumor, for example by bathing the tumor in a solution containing the phthalocyanine dye-antibody conjugate or by pouring the conjugate onto the tumor.

In addition, or alternatively, the disclosed compositions can be administered systemically, for example intravenously, intramuscularly, subcutaneously, intradermally, intraperitoneally, subcutaneously, or orally, to a subject having a tumor, such as cancer.

The dosages of the composition containing the conjugate to be administered to a subject are not subject to absolute limits, but will depend on the nature of the composition and its active ingredients and its unwanted side effects, such as immune response against the antibody, the subject being treated, and the type of condition being treated and the manner of administration. Generally, the dose will be a therapeutically effective amount, such as an amount sufficient to achieve a desired biological effect, for example an amount that is effective to decrease the size, such as volume and/or weight, of the tumor, or attenuate further growth of the tumor, or decrease undesired symptoms of the tumor.

In some embodiments, for example for intravenous administration of the composition containing the conjugate, exemplary dosages of the conjugate for administration to a subject for a single treatment can range from 0.5 to 100 mg/60 kg of body weight, 1 to 100 mg/60 kg of body weight, 1 to 50 mg/60 kg of body weight, 1 to 20 mg/60 kg of body weight, for example, about 1 or 2 mg/60 kg of body weight. In some embodiments, a therapeutically effective amount of intraperitoneally or intratumorally administered conjugate can vary from 10 µg to 5000 µg of conjugate to 1 kg of body weight, such as 10 µg/kg to 1000 µg/kg, 10 µg/kg to 500 µg/kg, or 100 µg/kg to 1000 µg/kg. In some embodiments, the conjugate is administered in an amount that is from or from about 0.5 mg/kg to about 100 mg/kg or 20 mg/m² to about 4000 mg/m². In some embodiments, the conjugate is administered in an amount that is at least or at least about or is or is about 0.5 mg/kg, 2.0 mg/kg, 4.0 mg/kg, 8.0 mg/kg, 16.0 mg/kg, 32.0 mg/kg or 64 mg/kg; or the conjugate is administered in an amount that is at least or at least about or is or is about 20 mg/m², 40 mg/m², 160 mg/m², 320 mg/m², 640 mg/m², 1280 mg/m² or 2560 mg/m².

In some embodiments, the dose of conjugate in the composition administered to a human patient is at least 25 mg, 50 mg, such as at least 100 mg, at least 300 mg, at least 500 mg, at least 750 mg, or even 1 g.

Treatments with disclosed compositions containing the conjugate can be completed in a single day, or may be done repeatedly on multiple days with the same or a different dosage. Repeated treatments may be done on the same day, on successive days, or every 1-3 days, every 3-7 days, every 1-2 weeks, every 2-4 weeks, every 1-2 months, or at even longer intervals.

In some embodiments, the method includes irradiating the tumor. In some embodiments, the irradiation is effected between or between about 30 minutes and 96 hours after administering the conjugate, such as between 30 minutes and 48 hours, 30 minutes and 24 hours or 12 hours and 48 hours, such as generally at least 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more after administering the conjugate. For example, the irradiation can be performed within about 24 hours after administering the conjugate or within about 20±4 hours after administering the conjugate. For example, the irradiation can be performed within about 24 hours after administering the conjugate or within about 24±4 hours after administering the conjugate.

In some embodiments, after the cells are contacted with the phthalocyanine dye-antibody conjugate, they are irradiated. Methods of irradiation are known in the art. As only cells expressing the cell surface protein will typically be recognized by the antibody, generally only those cells will have sufficient amounts of the conjugate bound to it. This may decrease the likelihood of undesired side effects, such as killing of normal cells, as the irradiation may only kill the cells to which the conjugate is bound, and generally not other cells.

In some embodiments, cells are irradiated in vitro, such as in a tissue culture dish. In some embodiments, a cell is irradiated in vivo, for example irradiating a subject who has previously been administered a composition containing the phthalocyanine dye-antibody conjugate. In some embodiments, the subject is irradiated, for example a tumor in the subject can be irradiated.

In some embodiments, a light or laser may be applied to the dye molecules, such as cells containing the conjugate, for from about 5 seconds to about 5 minutes. For example, in some embodiments, the light or laser is applied for or for about 5, 10, 15, 20, 25, 30, 35, 40, 45 50 or 55 seconds, or for within a range between any of two such values, to activate the dye molecules. In some embodiments, the light or laser is applied for or for about 1, 1.5, 2, 2.5, 3, 3.5, 4, 4.5 or 5 minutes, or more, or within a range between any two of such values. In some embodiments, the length of time a light or laser is applied can vary depending, for example, on the energy, such as wattage, of the light or laser. For example, lights or lasers with a lower wattage may be applied for a longer period of time in order to activate the dye molecule.

In some embodiments, a light or laser may be applied about 30 minutes to about 48 hours after administering the conjugate. For example, in some embodiments, the light or laser is applied at or at about 30, 35, 40, 45, 50 or 55 minutes after administering the conjugate, or within a range between any two of such values. In some embodiments, the light or laser is applied at or at about 1, 2, 3, 4, 5, 6, 7, 8, 9, 10, 11, 12, 13, 14, 15, 16, 17, 18, 19, 20, 21, 22, 23 or 24 hours after administering the conjugate, or is administered within a range between or between about any two of such values. In some embodiments, the light or laser is applied for between or between about 1 and 24 hours, such as between or between about 1 and 12 hours, 12 and 24 hours, 6 and 12 hours, or may be administered more than 24 following administration of the conjugate. In some embodiments, the light or laser is applied 36 or 48 hours after administering the conjugate. In some embodiments, the cells, hyperplasia, or tumor is irradiated within or within about or about 12 hours, 20±4 hours, 24 hours, 24±4 hours, 36 hours, 72 hours, or 96 hours after administering the conjugate.

In some embodiments, the dye molecules of the conjugate of the provided compositions described herein can be activated at a suitable wavelength. Thus, in some embodiments, the cells are irradiated with a therapeutic dose of radiation at a wavelength of from or from about 660-710 nm, such as 660-700 nm or 670-700 nm, for example, 690 nm. In some embodiments, activation of the dye molecules renders them cytotoxic or able to produce a cytotoxic molecule. Suitable wavelengths include, without limitation, ultraviolet wavelengths, visible wavelengths, infrared wavelengths and near infrared wavelengths. In some embodiments, the dye molecules are activated and become cytotoxic at a wavelength of from or from about 600 nm to 800 nm, or 660 nm to 740 nm. In some embodiments, the dye molecules are activated and become cytotoxic at a wavelength of about or at least about 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm or 800 nm, or within a range between or between about any 2 of such wavelengths. In some embodiments, the dye molecules are activated at a wavelength of less than 600 nm or more than 800 nm.

In some embodiments, the tumor is irradiated at a wavelength within a range from or from about 600 nm to 800 nm or 600 nm to 740 nm, such as 640 nm to 760 nm, 660 nm to 740 nm, 680 nm to 720 nm, or 690 nm to 710 nm. In some embodiments, the tumor is irradiated at a wavelength of 690±50 nm.

Suitable wavelengths for dye molecule activation may depend on the particular dye molecule used.

In some embodiments, the cells, hyperplasia or tumor are irradiated at a dose of at least or about 1 J cm$^{-2}$ (1 J/cm$^2$), such as at least or about 10 J cm$^{-2}$, at least or about 30 J cm$^{-2}$, at least or about 50 J cm$^{-2}$, at least or about 100 J cm$^{-2}$, or at least or about 500 J cm$^{-2}$, such as at least about 2 J cm$^{-2}$, 5 J cm$^{-2}$, 10 J cm$^{-2}$, 25 J cm$^{-2}$, 50 J cm$^{-2}$, 75 J cm$^{-2}$, 100 J cm$^{-2}$, 150 J cm$^{-2}$, 200 J cm$^{-2}$, 300 J cm$^{-2}$, 400 J cm$^{-2}$, or 500 J cm$^{-2}$. For example, in some embodiments, the cells, hyperplasia, or tumor are irradiated at from or from about 1-1000 J cm$^{-2}$, 1-500 J cm$^{-2}$, 10-100 J cm$^{-2}$, or 10-50 J cm$^{-2}$. In some embodiments, the tumor is irradiated at a dose of at least 0.5 J cm$^{-2}$, at least 1 J cm$^{-2}$, at least 2 J cm$^{-2}$, at least 3 J cm$^{-2}$, at least 4 J cm$^{-2}$, or at least 5 J cm$^{-2}$. In some embodiments, the cells, hyperplasia, or tumor is irradiated at a dose of 1 J cm$^{-2}$. In some embodiments, the cells, hyperplasia or tumor are irradiated at a dose of at least or at least about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length. In some embodiments, the cells are irradiated at a dose of at least 1 J cm-J or 1 J/cm of fiber length. In some embodiments, the cell, hyperplasia, or tumor is irradiated at a dose of from or from about 2 J cm$^{-2}$ to about 400 J cm$^{-2}$ or from or from about 2 J/cm fiber length to about 500 J/cm fiber length.

In some embodiments, the tumor is a superficial tumor. In some embodiments, the tumor is irradiated at a dose of at least or at least about or about 10 J/cm$^2$, 25 J/cm$^2$, 50 J/cm$^2$, 150 J/cm$^2$, or 250 J/cm$^2$.

In some embodiments, the tumor is an interstitial tumor. In some embodiments, the tumor is irradiated at a dose of at least or at least about or about 50 J/cm fiber length, 100 J/cm fiber length, 200 J/cm fiber length, or 300 J/cm fiber length.

In some embodiments, the dose of irradiation following administration of the composition comprising the phthalocyanine dye-antibody conjugate is at least 1 J cm$^{-2}$ at a wavelength of 660-740 nm, for example, at least 10 J cm$^{-2}$ at a wavelength of 660-740 nm, at least 50 J cm$^{-2}$ at a wavelength of 660-740 nm, or at least 100 J cm$^{-2}$ at a wavelength of 660-740 nm, for example 1 to 500 1.0 J cm$^{-2}$ at a wavelength of 660-740 nm. In some embodiments, the wavelength is 660-710 nm. In some embodiments, the dose of irradiation following administration of the composition comprising the phthalocyanine dye-antibody conjugate is at least 1.0 J cm$^{-2}$ at a wavelength of 680 nm for example, at least 10 J cm$^{-2}$ at a wavelength of 680 nm, at least 50 J cm$^{-2}$ at a wavelength of 680 nm, or at least 100 J cm$^{-2}$ at a wavelength of 680 nm, for example 1 to 500 1.0 J cm$^{-2}$ at a wavelength of 680 nm. In some embodiments, multiple irradiations are performed, such as at least 2, at least 3, or at least 4 irradiations, such as 2, 3, 4, 5, 6, 7, 8, 9, or 10 separate administrations.

In some embodiments, cells, or subjects, can be irradiated one or more times. Thus, irradiation can be completed in a single day, or may be done repeatedly on multiple days with the same or a different dosage, such as irradiation at least 2 different times, 3 different times, 4 different times 5 different times or 10 different times. In some embodiments, repeated irradiations may be done on the same day, on successive days, or every 1-3 days, every 3-7 days, every 1-2 weeks, every 2-4 weeks, every 1-2 months, or at even longer intervals.

In some embodiments, prior to, during, or following administration of the conjugate, the subject can receive one or more other therapies. In some embodiments, the subject receives one or more treatments to remove or reduce the tumor prior to administration of the conjugate.

In some of any embodiments, the lesion targeted comprises neurons and the disease or condition is a neurological disorder, which optionally comprises pain. In some of any embodiments, the lesion targeted comprises fat cells or adipocytes and the disease or condition comprises excess fat. In some of any embodiments, the lesion targeted comprises pathogen infected cells and the disease or condition comprises an infection. In some of any embodiments, the lesion targeted comprises an inflammatory cell and the disease or condition comprises inflammation.

In some of any embodiments of any of the pharmaceutical compositions or the methods described herein, the compositions herein are administered with and the methods herein are performed with the addition of a second therapeutic for the treatment of the lesion, disease, or condition, e.g., an additional therapeutic agent or anti-cancer treatment, such as any described herein. In some of any embodiments, the additional therapeutic agent or second therapeutic for the treatment is an immune modulator, an anti-cancer agent or other agent, that can increase the efficacy of treating the tumor, which, in some cases, can increase the therapeutic outcome or survival of the treated subject. In some of any embodiments, the additional therapeutic agent or second therapeutic is an immune checkpoint inhibitor. In some of any embodiments, the additional therapeutic agent or second therapeutic is any described below.

Combination with Additional Therapeutic Agent

Prior to, during, or following administration of the composition containing the phthalocyanine dye-antibody conjugate, the subject can receive one or more other therapies. In one example, the subject receives one or more treatments to remove or reduce the tumor prior to administration of the conjugate.

In some embodiments of the methods and compositions herein, the phthalocyanine dye-antibody conjugate, such as the cetuximab-IR700, is provided in combination with another therapeutic agent, such as one or both of an immune modulating agent or anti-cancer agent. In some embodiments, the phthalocyanine dye-antibody conjugate and other therapeutic agent can be packaged as an article of manufacture as separate compositions for administration together, sequentially or intermittently. The combinations can be packaged as a kit. In some embodiments, the therapeutic agent and phthalocyanine dye-antibody conjugate are formulated together in the same composition. In some embodiments, the therapeutic agent and phthalocyanine dye-antibody conjugate are formulated as separate compositions.

In some embodiments, the other or additional agent or agents administered, or the additional agent in a combination therapy, is an unconjugated antibody. In some embodiments, the unconjugated antibody is the same or substantially the same as the antibody of the conjugate. For example, in some embodiments, prior to administration of the composition containing the conjugate, the unconjugated antibody that targets a protein or antigen, is administered to the subject. In some embodiments, the antibody is administered up to 96 hours prior to administration of the conjugate. In some embodiments, the antibody is administered at a dose within a range from or from about 10 mg/m$^2$ to about 500 mg/m$^2$. For example, the antibody is cetuximab, and cetuximab is administered to the subject up to 96 hours prior to administration of the composition containing the conjugate.

In some embodiments, the other or additional agent or agents administered, or the additional agent in a combination therapy, is an immune modulating agent or anti-cancer agent. In some embodiments, the immune modulating agent, anti-cancer agent and/or phthalocyanine dye-antibody conjugate (e.g., cetuximab-IR700 conjugate) are formulated as separate compositions. In some embodiments, the immune modulating agent is provided as a separate composition from the phthalocyanine dye-antibody conjugate, and the two compositions are administered separately. In some embodiments, the anti-cancer agent is provided as a separate composition from the phthalocyanine dye-antibody conjugate, and the two compositions are administered separately. In some embodiments, phthalocyanine dye-antibody conjugate (e.g., cetuximab-IR700 conjugate) is formulated with one or more stabilizing agents, where the stabilization agents are non-ionic surfactants and/or protectants, and the immune modulating agent or anti-cancer agent is administered in a separate and different formulation.

In some embodiments, the immune modulating agent and/or anti-cancer agent and the phthalocyanine dye-antibody conjugate is formulated in the same composition. The compositions can be formulated for parenteral delivery (i.e. for systemic delivery). For example, the compositions or combination of compositions are formulated for subcutaneous delivery or for intravenous delivery. The agents, such as a phthalocyanine dye-antibody conjugate, an immune modulating agent, and/or an anti-cancer agent can be administered by different routes of administration.

Examples of additional therapies that can be used in combination with the disclosed antibody-IR700 conjugates for treating cancers or tumors, which may enhance accessibility of the tumor to additional therapeutic agents, include but are not limited to, surgical treatment for removal or reduction of the tumor, such as surgical resection, cryotherapy, or chemoembolization, as well as anti-tumor pharmaceutical treatments which can include radiotherapeutic agents, anti-neoplastic chemotherapeutic agents, antibiotics, alkylating agents and antioxidants, kinase inhibitors, and other agents. In some examples, the additional therapeutic agent is conjugated to a nanoparticle. Particular examples of additional therapeutic agents that can be used include microtubule binding agents, DNA intercalators or cross-linkers, DNA synthesis inhibitors, DNA and/or RNA transcription inhibitors, antibodies, enzymes, enzyme inhibitors, and gene regulators. These agents, which are administered at a therapeutically effective amount, and treatments can be used alone or in combination. Methods and therapeutic dosages of such agents are known to those skilled in the art, and can be determined by a skilled clinician.

In some embodiments, at least a portion of the tumor, such as a metastatic tumor, is surgically removed, for example via cryotherapy, irradiated, chemically treated, for example via chemoembolization, or combinations thereof, prior to administration of the disclosed therapies, such as administration of phthalocyanine dye-antibody conjugate. For example, a subject having a metastatic tumor can have all or part of the tumor surgically excised prior to administration of the disclosed therapies. In some embodiments, one or more chemotherapeutic agents are administered following treatment with conjugate and irradiation. In some embodiments, the subject has a metastatic tumor and is administered radiation therapy, chemoembolization therapy, or both concurrently with the administration of the disclosed therapies.

In some embodiments, the immune modulating agent is or comprises an antibody or an antigen-binding fragment thereof, a small molecule or a polypeptide. In some embodiments, the immune modulating agent is or comprises the immune modulating agent specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28, VISTA, ICOS, ICOS-L, CD27, CD30, STING, CCR4, and A2A adenosine receptor. In some embodiments, the immune modulating agent is selected from among cemiplimab, nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof. In some embodiments, the immune modulating agent is administered prior to treatment with conjugate and irradiation, such as at or at about 1 week, 2 weeks, 3 weeks or 4 weeks prior to conjugate administration. In some embodiments, the immune modulating agent is administered subsequent to treatment with conjugate and irradiation, such as at or at about 1 week, 2 weeks, 3 weeks or 4 weeks after conjugate administration. In some embodiments, the immune modulating agent is administered prior to and subsequent to treatment with conjugate and irradiation, such as on a cycle of every 1 week, 2 weeks, 3 weeks or 4 weeks.

In some embodiments, the anti-cancer agent is an alkylating agent, a platinum drug, an antimetabolite, an antitumor antibiotic, a topoisomerase inhibitor, a mitotic inhibitor, a corticosteroid, a proteasome inhibitor, a kinase inhibitor, a histone-deacetylase inhibitor, an anti-neoplastic agent, or a combination thereof. In some embodiments, the anti-cancer agent is an antibody or an antigen-binding fragment thereof, a small molecule or a polypeptide.

In some embodiments, the anti-cancer agent is selected from among 5-Fluorouracil/leukovorin, oxaliplatin, irinotecan, regorafenib, ziv-afibercept, capecitabine, cisplatin, paclitaxel, toptecan, carboplatin, gemcitabine, docetaxel, 5-FU, ifosfamide, mitomycin, pemetrexed, vinorelbine, carmustine wager, temozolomide, methotrexate, capacitabine, lapatinib, etoposide, dabrafenib, vemurafenib, liposomal cytarabine, cytarabine, interferon alpha, erlotinib, vincristine, cyclophosphamide, lomusine, procarbazine, sunitinib, somastostatin, doxorubicin, pegylated liposomal encapsulated doxorubicin, epirubicin, eribulin, albumin-bound paclitaxel, ixabepilone, cotrimoxazole, taxane, vinblastine, temsirolimus, temozolomide, bendamustine, oral etoposide, everolimus, octreotide, lanredtide, dacarbazine, mesna, pazopanib, eribulin, imatinib, regorafenib, sorafenib, nilotinib, dasantinib, celecoxib, tamoxifen, toremifene, dactinomycin, sirolimus, crizotinib, certinib, enzalutamide, abiraterone acetate, mitoxantrone, cabazitaxel, fluoropyrimidine, oxaliplatin, leucovorin, afatinib, ceritinib, gefitinib, cabozantinib, oxoliplatin and auroropyrimidine. In some embodiments, wherein the anti-cancer agent is selected from among bevacizumab, cetuximab, panitumumab, ramucirumab, ipilimumab, rituximab, trastuzumab, ado-trastuzumab emtansine, pertuzumab, nivolumab, lapatinib, dabrafenib, vemurafenib, erlotinib, sunitinib, pazopanib, imatinib, regorafenib, sorafenib, nilotinib, dasantinib, celecoxib, crizotinib, certinib, afatinib, axitinib, bevacizumab, bosutinib, cabozantinib, afatinib, gefitinib, temsirolimus, everolimus, sirolimus, ibrutinib, imatinib, lenvatinib, olaparib, palbociclib, ruxolitinib, trametinib, vandetanib or vismodegib, or an antigen-binding fragment thereof.

IV. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X". In some embodiments, "about a value" is or refers to ±25%, ±10%, ±5%, ±1%, ±0.1%, ±0.01% of the value.

As used herein, a "conjugate" refers to a polypeptide linked directly or indirectly to one or more other molecules, such as polypeptides or chemical moieties. Such conjugates include fusion proteins, those produced by chemical conjugates, and those produced by any other methods. For example, a conjugate can refer to a phthalocyanine dye, such as an IR700 molecule, linked directly or indirectly to one or more other molecules, such as an antibody.

As used herein, a composition refers to any mixture of two or more products, substances, or compounds, including cells. It may be a solution, a suspension, liquid, powder, a paste, aqueous, non-aqueous or any combination thereof.

As used herein, a "pharmaceutical composition" or "pharmaceutical formulation" refers to a preparation which is in such form as to permit the biological activity of an active ingredient contained therein to be effective, and which contains no additional components which are unacceptably toxic to a subject to which the formulation would be administered.

As used herein, a "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, a kit is a packaged combination that optionally includes other elements, such as additional reagents and instructions for use of the combination or elements thereof.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, an "article of manufacture" is a product that is made and, in some cases, that can be sold. In some embodiments, the term can refer to compositions contained in articles of packaging, such as in a container.

As used herein, "disease or disorder" refers to a pathological condition in an organism resulting from cause or condition including, but not limited to, infections, acquired conditions, genetic conditions, and characterized by identifiable symptoms. Diseases and disorders of interest herein are those that are treatable by immune globulin.

As used herein, "treating" a subject with a disease or condition means that the subject's symptoms are partially or totally alleviated, or remain static following treatment. Hence treating encompasses prophylaxis, therapy, and/or cure. Prophylaxis refers to prevention of a potential disease and/or a prevention of worsening of symptoms or progression of a disease.

As used herein, "treatment" means any manner in which the symptoms of a condition, disorder or disease or other indication, are ameliorated or otherwise beneficially altered.

As used herein, "therapeutic effect" means an effect resulting from treatment of a subject that alters, typically improves or ameliorates the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect. Hence, it is the quantity necessary for preventing, curing, ameliorating, arresting, or partially arresting a symptom of a disease or disorder.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, the term "subject" refers to an animal, including a mammal, such as a human being.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein the term "substantially" refers to a high level of similarity. In some embodiments, substantially may refer to almost all or complete, such as at least 85%, 90%, 95%, 99%, 99.9%, or 99.99% complete. For example, in some embodiments, if an agent is said to be substantially in a state, then at least 85%, 90%, 95%, 99%, 99.9%, or 99% of the agent is in the state.

All publications, including patent documents, scientific articles, and databases referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

V. EXEMPLARY EMBODIMENTS

Among the embodiments provided herein are:
1. A pharmaceutical composition comprising: (1) a conjugate comprising an antibody linked to IR700 and (2) one or more stabilizing agents in an amount effective to reduce or prevent aggregation of the conjugate, wherein the one or more stabilizing agents comprises a surfactant and/or a protectant.
2. A pharmaceutical composition comprising: (1) a conjugate comprising an antibody linked to IR700 and (2) one or more stabilizing agents in an amount effective to reduce or prevent aggregation of the conjugate, wherein the one or more stabilizing agents comprises a non-ionic surfactant or a zwitterionic surfactant, and/or a protectant.
3. A pharmaceutical composition comprising: (1) a conjugate comprising a cetuximab or a biosimilar, interchangeable, or biobetter thereof linked to IR700 and (2) one or more stabilizing agents in an amount effective to reduce or prevent aggregation of the conjugate, wherein the one or more stabilizing agents comprises a surfactant and/or a protectant.
4. The pharmaceutical composition of any one of embodiments 1 to 3, wherein the conjugate is substantially in a non-aggregated monomeric form.
5. The pharmaceutical composition of any one of embodiments 1 to 3, wherein the one or more stabilizing agents is present in an amount effective to reduce or prevent aggregation of the conjugate under a temperature stress condition.
6. The pharmaceutical composition of any one of embodiments 1 to 3, wherein the one or more stabilizing agents is present in an amount effective to reduce or prevent aggregation of the conjugate under an agitation stress condition.
7. The pharmaceutical composition of any one of embodiments 1 to 6, wherein the one or more stabilizing agents comprises a surfactant.
8. The pharmaceutical composition of any one of embodiments 1 to 7, wherein the one or more stabilizing agents comprise a non-ionic surfactant.
9. The pharmaceutical composition of any one of embodiments 1 to 8, wherein the non-ionic surfactant is present at a percentage by weight to volume (w/v) of at least or at least about 0.01%.
10. The pharmaceutical composition of any one of embodiments 2 to 9, wherein the non-ionic surfactant is selected from the group consisting of a polysorbate, a polyethylene glycol (PEG), a block copolymer of polyethylene glycol and polypropylene glycol or a polyethylene glycol octylphenyl ether, or a combination thereof.
11. The pharmaceutical composition of any one of embodiments 2 to 10, wherein the non-ionic surfactant is a polysorbate.
12. The pharmaceutical composition of embodiment 11, wherein the polysorbate is selected from the group consisting of polysorbate 20, polysorbate 40, polysorbate 60, polysorbate 80, and combinations thereof.
13. The pharmaceutical composition of embodiment 11 or 12, wherein the polysorbate is polysorbate 20.
14. The pharmaceutical composition of embodiment 11 or 12, wherein the polysorbate is polysorbate 80.
15. The pharmaceutical composition of any one of embodiments 10 to 14, wherein the polysorbate is present at a percentage by weight to volume (w/v) of between 0.01% and 0.10%, between 0.01% and 0.075%, between 0.01% and 0.05%, between 0.05% and 0.1%, between 0.05% and 0.075% and between 0.075% and 0.10%, each inclusive.
16. The pharmaceutical composition of any one of embodiments 10 to 14, wherein the polysorbate is present at a percentage by weight to volume (w/v) of at least or at least about 0.02%, 0.03%, 0.04%, or 0.05%.
17. The pharmaceutical composition of any one of embodiments 10 to 14, wherein the polysorbate is present at a percentage by weight to volume (w/v) of between 0.01% and 0.1%, between 0.1% and 0.5%, between 0.02% and 0.06%, between 0.02% and 0.05%, between 0.02% and 0.04%, between 0.02% and 0.03%, between 0.03% and 0.06%, between 0.03% and 0.05%, between 0.03% and 0.04%, between 0.04% and 0.06%, between 0.04% and 0.05%, between 0.05% and 0.06%, each inclusive.
18. The pharmaceutical composition of any one of embodiments 10 to 17, wherein the polysorbate is present at a percentage by weight to volume (w/v) of at or about or at least or at least about 0.02%, 0.03%, 0.04%, or 0.05%.
19. The pharmaceutical composition of any one of embodiments 10 to 18, wherein the polysorbate is present at a percentage by weight to volume (w/v) of between 0.01% and 0.1%, between 0.1% and 0.5%, between 0.02% and 0.06%, between 0.02% and 0.05%, between 0.02% and 0.04%, between 0.02% and 0.03%, between 0.03% and 0.06%, between 0.03% and 0.05%, between 0.03% and 0.04%, between 0.04% and 0.06%, between 0.04% and 0.05%, between 0.05% and 0.06%, each inclusive.
20. The pharmaceutical composition of any one of embodiments 2 to 10, wherein the non-ionic surfactant is a polyethylene glycol (PEG).
21. The pharmaceutical composition of embodiment 20, wherein the polyethylene glycol (PEG) is PEG 8000.
22. The pharmaceutical composition of embodiment 20 or 21, wherein the PEG is present at a percentage by weight to volume (w/v) of between 0.01% and 10%, between 0.025% and 7.5%, between 0.05% and 5%, between 0.05% and 2.5%, between 0.05% and 1%, between 0.05% and 0.75%, between 0.05% and 0.5%, between 0.05% and 0.25%, between 0.1% and 7.5%, between 0.1% and 5%, between 0.1% and 2.5%, between 0.1% and 1%, between 0.1% and 0.75%, between 0.1% and 0.5%, between 0.1% and 0.25%, between 0.5% and 7.5%, between 0.5% and 5%, between 0.5% and 2.5%, between 0.5% and 1%, between 0.5% and 0.75%, between 1% and 7.5%, between 1% and 5% and between 1% and 2.5%, each inclusive.
23. The pharmaceutical composition of any one of embodiments 20 to 22, wherein the PEG is present at a percentage by weight to volume (w/v) of at or about or at least or at least about 0.05%, 0.5% or 1%.
24. The pharmaceutical composition of any one of embodiments 2 to 10, wherein the non-ionic surfactant is a block copolymer of polyethylene glycol and polypropylene glycol.
25. The pharmaceutical composition of embodiment 24, wherein the block copolymer of polyethylene glycol and polypropylene glycol is polyoxyethylene-polyoxypropylene block copolymer (Pluronic® F-68).
26. The pharmaceutical composition of embodiment 24 or 25, wherein the Pluronic® F-68 is present at a percentage by weight to volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive.
27. The pharmaceutical composition of any one of embodiments 24 to 26, wherein the Pluronic® F-68 is present at a percentage by weight to volume (w/v) of at or about or at least or at least about 0.05%, 0.5% or 1%.
28. The pharmaceutical composition of any one of embodiments 2 to 10, wherein the non-ionic surfactant is a polyethylene glycol octylphenyl ether.
29. The pharmaceutical composition of embodiment 28, wherein the polyethylene glycol octylphenyl ether is polyethylene glycol p-(1,1,3,3-tetramethylbutyl)-phenyl ether (Triton X-100®).
30. The pharmaceutical composition of embodiment 28 or 29, wherein the Triton X-100® is present at a percentage by weight to volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive.

31. The pharmaceutical composition of any one of embodiments 28 to 30, wherein the Triton X-100 is present at a percentage by weight to volume (w/v) of at or about or at least or at least about 0.05%, 0.5% or 1%.

32. The pharmaceutical composition of any one of embodiments 1 to 11, wherein the one or more stabilizing agents comprise a zwitterionic surfactant.

33. The pharmaceutical composition of embodiment 32, wherein the zwitterionic surfactant is 3-[(3-Cholamidopropyl) dimethylammonio]-1-propanesulfonate (CHAPS).

34. The pharmaceutical composition of embodiment 32 or 33, wherein the CHAPS is present at a percentage by weight to volume (w/v) of between 0.01% and 5%, between 0.025% and 2.5%, between 0.05% and 2.5%, between 0.05% and 1%, between 0.05% and 0.75%, between 0.05% and 0.5%, between 0.05% and 0.25%, between 0.1% and 5%, between 0.1% and 2.5%, between 0.1% and 1%, between 0.1% and 0.75%, between 0.1% and 0.5%, between 0.1% and 0.25%, between 0.5% and 5%, between 0.5% and 2.5%, between 0.5% and 1% and between 0.5% and 0.75%, each inclusive.

35. The pharmaceutical composition of any one of embodiments 32 to 34, wherein the CHAPS is present at a percentage by weight to volume (w/v) of at or about or at least or at least about 0.05%, 0.5% or 1%.

36. The pharmaceutical composition of any one of embodiments 1 to 35, wherein the one or more stabilizing agents comprises a protectant.

37. The pharmaceutical composition of embodiment 36, wherein the protectant is selected from the group consisting of trehalose, sucrose, mannitol, and sorbitol.

38. The pharmaceutical composition of embodiment 36 or 37, wherein the protectant is selected from the group consisting of trehalose, sucrose and sorbitol.

39. The pharmaceutical composition of any one of embodiments 36 to 38, wherein the protectant is trehalose.

40. The pharmaceutical composition of any one of embodiments 36 to 39, wherein the protectant is present in an amount of between 1% and 20%, between 3% and 12%, or between 5% and 9% by weight to volume (w/v), each inclusive.

41. The pharmaceutical composition of any one of embodiments 36 to 39, wherein the protectant is present in an amount of at or about or at least or at least about 1%, 2%, 3%, 4%, 5%, 6%, 7%, 8%, 9%, 10%, 11%, 12%, 13%, 14% or 15% by weight to volume (w/v).

42. The pharmaceutical composition of any one of embodiments 1 to 41, wherein the antibody is an antigen-binding fragment.

43. The pharmaceutical composition of any one of embodiments 1 to 42, wherein the antibody binds to HER1 or a portion thereof.

44. The pharmaceutical composition of any one of embodiments 1 to 43, wherein the antibody is cetuximab or a biosimilar or biobetter thereof.

45. The pharmaceutical composition of any one of embodiments 1 to 44, wherein the antibody is cetuximab.

46. The pharmaceutical composition of any one of embodiments 1 to 45 wherein the conjugate is cetuximab-IR700.

47. A pharmaceutical composition comprising (1) a conjugate comprising an anti-HER1 (EGFR) antibody linked to IR700, (2) polysorbate 80, and (3) trehalose.

48. The pharmaceutical composition of any one of embodiments 1 to 47, wherein the conjugate is formulated to a concentration that is from or from about 1.0 to or to about 5.0 mg/mL, from or from about 2.0 to or to about 10.0 mg/mL, from or from about 5.0 to or to about 50 mg/mL, or from or from about 20 to or to about 50 mg/mL.

49. The pharmaceutical composition of any one of embodiments 1 to 48, wherein the conjugate is formulated to a concentration between 2 mg/mL and 10 mg/mL.

50. The pharmaceutical composition of any one of embodiments 1 to 49, wherein the conjugate is formulated to a concentration of, of about, or of least 5 mg/mL.

51. The pharmaceutical composition of any one of embodiments 12 to 50, wherein the polysorbate 80 is present at between 0.01% and 0.1%, between 0.1% and 0.5%, or between 0.02% and 0.04% by weight to volume (w/v), each inclusive.

52. The pharmaceutical composition of any one of embodiments 12 to 51, wherein the polysorbate 80 is present at or at about 0.02% by weight to volume (w/v).

53. The pharmaceutical composition of any one of embodiments 37 to 52, wherein the trehalose is present in amount between 1% and 20%, 3% and 12%, or 5% and 9% by weight to volume (w/v), each inclusive.

54. The pharmaceutical composition of any one of embodiments 37 to 53, wherein the trehalose is present in amount of between 5% and 9% by weight to volume (w/v), inclusive.

55. The pharmaceutical composition of any one of embodiments 1 to 54, wherein the composition is formulated in a pharmaceutically acceptable buffer.

56. The pharmaceutical composition of embodiment 55, wherein the pharmacologically acceptable buffer has a pH from or from about pH 6.0 to about pH 8.0, inclusive.

57. The pharmaceutical composition of embodiment 55 or 56, wherein the pharmaceutically acceptable buffer has a pH of from or from about pH 6.8 to pH 7.4, inclusive.

58. The pharmaceutical composition of any one of embodiments 55 to 57, wherein the pharmaceutically acceptable buffer has a pH of or of about pH 7.1.

59. The pharmaceutical composition of any one of embodiments 55 to 58, wherein the pharmaceutically acceptable buffer is sodium phosphate.

60. The pharmaceutical composition of embodiment 59, wherein the sodium phosphate is present at a concentration of between 1 mM and 200 mM, between 1 mM and 50 mM, or between 5 mM and 25 mM, each inclusive.

61. A pharmaceutical composition comprising (1) between 2 mg/mL and 10 mg/mL of a conjugate comprising an anti-HER1 (EGFR) antibody linked to IR700, (2) between 0.1% and 0.5% polysorbate 80 by weight to volume (w/v), (3) between 5% and 9% trehalose by weight to volume (w/v), and (4) between 5 mM and 25 mM sodium phosphate, each inclusive.

62. The pharmaceutical composition of any one of embodiments 47 to 61, wherein the antibody is cetuximab or a biosimilar, interchangeable, or biobetter thereof.

63. The pharmaceutical composition of any one of embodiments 47 to 62, wherein the antibody is cetuximab.

64. The pharmaceutical composition of any one of embodiments 47 to 63, wherein the conjugate comprises a cetuximab-IR700 conjugate.

65. The pharmaceutical composition of any one of embodiments 61 to 64, wherein the composition comprises polysorbate 80 at or at about 0.02% w/v.

66. The pharmaceutical composition of any one of embodiments 61 to 65, wherein the composition comprises trehalose at or at about 0.2% w/v.

67. The pharmaceutical composition of any one of embodiments 1 to 66, wherein the composition has a pH of or of about pH 6.0 to pH 8.0.

68. The pharmaceutical composition of any one of embodiments 1 to 67, wherein the composition has a pH of or of about pH 6.8 to pH 7.4.

69. The pharmaceutical composition of any one of embodiments 1 to 68, wherein the composition has a pH of or of about pH 7.1.

70. A pharmaceutical composition comprising 5 mg/mL cetuximab-IR700 conjugate in a formulation comprising 10 mM sodium phosphate, 0.02% (w/v) polysorbate 80 and 9% (w/v) trehalose at a pH of or of about pH 7.1.

71. The pharmaceutical composition of any one of embodiments 1 to 70, wherein the composition is a liquid ready to use composition.

72. The pharmaceutical composition of any one of embodiments 1 to 70, wherein the composition is lyophilized or is formulated for lyophilization or is reconstituted from a lyophilized composition.

73. The pharmaceutical composition of any one of embodiments 1 to 72, wherein the composition is sterile.

74. The pharmaceutical composition of any one of embodiments 1 to 73 that is stable at 2° C. to 8° C. for greater than 6 months, 12 months or 18 months.

75. The pharmaceutical composition of any one of embodiments 1 to 74, wherein the conjugate is present in at least or at least about 70%, 80%, 85%, 90%, 95%, or 98% monomeric form.

76. The pharmaceutical composition of embodiment 75, wherein the percentage of monomeric form is assessed by size-exclusion chromatography.

77. The pharmaceutical composition of any one of embodiments 1 to 76, wherein aggregation of the conjugate is reduced by 1%, 5%, 10%, 20%, 30%, 40%, 50%, 60%, 70%, 80%, 90%, 95%, 99%, or more compared to aggregation in a composition comprising the conjugate but lacking the stabilizing agent.

78. The pharmaceutical composition of any one of embodiments 1 to 77, wherein the reduced aggregation is present after sheer stress and/or agitation; after exposure to a pH of less than or less than about pH 6.0; after 3 months at a temperature greater than or greater than about 25° C.; and/or after exposure for 1 week at a temperature greater than or greater than about 40° C., or combinations thereof.

79. The pharmaceutical composition of any one of embodiments 1 to 78, wherein the reduced aggregation is characterized by percent recovery, the percentage of the conjugate in monomeric form, the percentage of the conjugate contained in a mean peak, potency of the composition, activity of the composition, purity or the composition, or combinations thereof.

80. The pharmaceutical composition of embodiment 79, wherein the recovery of the conjugate is greater than 80%, 85%, 90%, 91%, 92%, 93%, 94%, 95%, 96%, 97%, 98%, 99%, 99.5%, 99.9%, or 100% after sheer stress and/or agitation; after exposure to a pH less than or less than about pH 6.0; after 3 months at a temperature greater than or greater than about 25° C.; and/or after exposure for 1 week at a temperature greater than or greater than about 40° C., or combinations thereof.

81. The pharmaceutical composition of embodiment 79 or 80, wherein the percentage of the conjugate in monomeric form in the composition is at least 70%, 80%, 85%, 90%, 91%, 92%, 93%, 94%, 95%, 96%, 97%, 98%, 99% after sheer stress and/or agitation; after exposure to a pH of less than or less than about pH 6.0; after 3 months at a temperature greater than or greater than about 25° C.; and/or after exposure for 1 week at a temperature greater than or greater than about 40° C., or combinations thereof.

82. The pharmaceutical composition of any one of embodiments 79 to 81, wherein the percentage of the conjugate contained in a mean peak as determined by high performance liquid chromatography (HPLC) is greater than 70%, 80%, 85%, 90%, 91%, 92%, 93%, 94%, 95%, 96%, 97%, 98%, or 99% after sheer stress and/or agitation; after exposure to a pH of less than or less than about pH 6.0; after exposure for more than or about 3 months to a temperature greater than or greater than about 25° C.; and/or after exposure for 1 week at a temperature greater than or greater than about 40° C., or combinations thereof.

83. The pharmaceutical composition of embodiment 82, wherein the HPLC is size exclusion HPLC (SE-HPLC).

84 The pharmaceutical composition of any one of embodiments 79 to 83, wherein the composition retains greater than or greater than about 30%, 40%, 50%, 60%, 70%, 80%, 90%, 91%, 92%, 93%, 94%, 95%, 96%, 97%, 98%, 99%, 99.5%, 99.9% or 100% of its potency, activity or purity after sheer stress and/or agitation; after exposure to a pH of less than or less than about pH 6.0; after exposure for more than or about 3 months to a temperature greater than or greater than about 25° C.; and/or after exposure for 1 week at a temperature greater than or greater than about 40° C., or combinations thereof.

85. The pharmaceutical composition of any one of embodiments 1 to 84, wherein the reduced aggregation is present after sheer stress and/or agitation; after exposure to a pH of less than or less than about pH 6.0; after 3 months at a temperature greater than or greater than about 25° C., or combinations thereof.

86. The pharmaceutical composition of any one of embodiments 1 to 85, wherein the reduced aggregation is characterized by percent recovery, the percentage of the conjugate in monomeric form, the percentage of the conjugate contained in a mean peak, potency of the composition, activity of the composition, purity or the composition, or combinations thereof.

87. The pharmaceutical composition of embodiment 86, wherein the recovery of the conjugate is greater than 80%, 85%, 90%, 91%, 92%, 93%, 94%, 95%, 96%, 97%, 98%, 99%, 99.5%, 99.9%, or 100% after sheer stress and/or agitation; after exposure to a pH less than or less than about pH 6.0; and/or after 3 months at a temperature greater than or greater than about 25° C., or combinations thereof.

88. The pharmaceutical composition of embodiment 86 or embodiment 87, wherein the percentage of the conjugate in monomeric form in the composition is at least 70%, 80%, 85%, 90%, 91%, 92%, 93%, 94%, 95%, 96%, 97%, 98%, 99% after sheer stress and/or agitation; after exposure to a pH of less than or less than about pH 6.0; and/or after 3 months at a temperature greater than or greater than about 25° C., or combinations thereof.

89. The pharmaceutical composition of any one of embodiments 86 to 88, wherein the percentage of the conjugate contained in a mean peak as determined by high performance liquid chromatography (HPLC) is greater than 70%, 80%, 85%, 90%, 91%, 92%, 93%, 94%, 95%, 96%, 97%, 98%, or 99% after sheer stress and/or agitation; after exposure to a pH of less than or less than about pH 6.0; and/or after exposure for more than or about 3 months to a temperature greater than or greater than about 25° C., or combinations thereof.

90. The pharmaceutical composition of embodiment 89, wherein the HPLC is size exclusion HPLC (SE-HPLC).

91. The pharmaceutical composition of any one of embodiments 86 to 90, wherein the composition retains greater than or greater than about 30%, 40%, 50%, 60%, 70%, 80%, 90%, 91%, 92%, 93%, 94%, 95%, 96%, 97%, 98%, 99%, 99.5%, 99.9% or 100% of its potency, activity or purity after sheer stress and/or agitation; after exposure to a pH of less than or less than about pH 6.0; and/or after exposure for more than or about 3 months to a temperature greater than or greater than about 25° C., or combinations thereof.

92. The pharmaceutical composition of any one of embodiments 86 to 91, wherein the shear stress and/or agitation is caused by shaking, freeze-thaw, transportation, drawing into a syringe, purification procedures or manufacturing procedures.

93. The pharmaceutical composition of embodiment 92, wherein the shaking comprises shaking on an orbital shaker.

94. The pharmaceutical composition of embodiment 92 or embodiment 93, wherein the shaking is at a speed greater than 25 rpm, greater than 50 rpm, greater than 75 rpm, greater than 100 rpm, greater than 125 rpm, greater than 150 rpm, greater than 175 rpm, greater than 200 rpm, greater than 225 rpm, greater than 250 rpm, greater than 275 rpm, or greater than 300 rpm.

95. The pharmaceutical composition of any one of embodiments 92 to 94, wherein the shaking is carried out for a period of time is greater than 1 minute, greater than 5 minutes, greater than 10 minutes, greater than 15 minutes, greater than 20 minutes, greater than 25 minutes, greater than 30 minutes, greater than 45 minutes, greater than 60 minutes, greater than 90 minutes, greater than 120 minutes, greater than 150 minutes, greater than 180 minutes, greater than 210 minutes, greater than 240 minutes, greater than 270 minutes, greater than 300 minutes, greater than 330 minutes, greater than 360 minutes, greater than 390 minutes, greater than 420 minutes, greater than 450 minutes, greater than 480 minutes, greater than 510 minutes, greater than 540 minutes, greater than 570 minutes, or greater than 600 minutes.

96. The pharmaceutical composition of any one of embodiments 86 to 95, wherein the exposure for more than or about 3 months is at a temperature greater than or greater than about 30° C., 35° C., 37° C., or 40° C.

97. The pharmaceutical composition of any one of embodiments 86 to 96, wherein the exposure for more than 1 week at a temperature greater than or greater than about 40° C. is for more than at or about 1 week, more than at or about 2 weeks or more than at or about 1 month.

98. A container, comprising the pharmaceutical composition of any one of embodiments 1 to 97.

99. The container of embodiment 98, wherein the container is a vial, a tube, a syringe, a bag, a pouch or a box.

100. The container of embodiment 99 or embodiment 100, wherein the container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

101. The container of embodiment 100, wherein the container protects from transmission of light such that the percentage of light transmission is less than 50%, less than 40%, less than 30%, less than 20%, less than 10% or less than 5%.

102. The container of any one of embodiments 98 to 101, wherein the container is green, blue, amber, translucent, opaque, or is covered by a material with light transmission of less than 50%, less than 40%, less than 30%, less than 20%, less than 10% or less than 5%.

103. A method of treating a cancer or tumor in a subject comprising:
a) administering to the subject a therapeutically effective amount of the pharmaceutical composition of any one of embodiments 1 to 98; and
b) after administering the conjugate, irradiating the cancer or tumor at a wavelength to induce phototoxic activity of the conjugate.

104. The method of embodiment 103, wherein the irradiating step is carried out at wavelength of 600 nm to 850 nm at a dose of at least 1 J cm$^{-2}$ or 1 J/cm of fiber length.

105. The method of embodiment 103, wherein the irradiating step is carried out at a wavelength of about 690 nm.

106. The method of embodiment 103, wherein the irradiating step is carried out at a wavelength of 690±50 nm or at a wavelength of or about 690±20 nm.

107. The method of any one of embodiments 103 to 106, wherein the irradiating step is carried out at a dose of from or from about 25 J/cm$^2$ to about 100 J/cm$^2$.

108. The method of any one of embodiments 103 to 106, wherein the irradiating step is carried out with a frontal light diffuser at a dose of or of about 50 J/cm$^2$.

109. The method of embodiment 107 or 108 wherein the irradiating step is carried out with a frontal light diffuser or by superficial illumination.

110. The method of any one of embodiments 103 to 106, wherein the irradiating step is carried out with a cylindrical light diffuser at a dose of from or from about 50 J/cm fiber length to about 150 J/cm fiber length 111. The method of any one of embodiments 103 to 106, wherein the irradiating step is carried out with a cylindrical light diffuser at a dose of or of about 100 J/cm fiber length.

112. The method of embodiment 110 or 111, wherein the irradiating step is carried out with a cylindrical light diffuser or by interstitial illumination 113. The method of any one of embodiments 103 to 112, wherein the tumor is a carcinoma that is a carcinoma of the bladder, pancreas, colon, ovary, lung, breast, stomach, prostate, cervix, esophagus or head and neck.

114. The method of embodiment 113, wherein the cancer is a cancer located at the head and neck, breast, liver, colon, ovary, prostate, pancreas, brain, cervix, bone, skin, eye, bladder, stomach, esophagus, peritoneum, or lung.

115. The method of embodiments 9103 to 114, wherein the conjugate is IR700-cetuximab.

116. The method of embodiments 103 to 115, wherein the cancer is a cancer located at the head and neck, and the conjugate is IR700-cetuximab.

117. The method of embodiment 116, wherein the irradiating step is carried out between or between or between about 10 and about 40 hours after administering the conjugate.

118. The method of embodiment 116 or 117, wherein the irradiating step is carried out between or between or between about 20 and about 28 hours after administering the conjugate.

119. The method of any one of embodiments 116-118, wherein the irradiating step is carried out at about 24 hours after administering the conjugate.

120. The method of any one of embodiments 103 to 119, wherein the conjugate is administered at a dose from or from about 250 mg/m$^2$ to about 1000 mg/m$^2$, from or from about 500 mg/m$^2$ to about 750 mg/m$^2$, from or from about 600 mg/m$^2$ to about 700 mg/m$^2$.

121. The method of any one of embodiments 103 to 120, wherein the conjugate is administered at a dose of or of about 500 mg/m$^2$, 550 mg/m$^2$, 580 mg/m$^2$, 600 mg/m$^2$, 620 mg/m$^2$, 640 mg/m$^2$, 660 mg/m$^2$, 680 mg/m$^2$ or 700 mg/m$^2$.

122. The method of any one of embodiments 103 to 121, wherein the conjugate is administered at a dose of or of about 640 mg/m$^2$.

123. The method of any one of embodiments 103 to 122, further comprising administering an additional therapeutic agent or anti-cancer treatment.

124. The method of embodiment 123, wherein the additional anti-cancer treatment comprises radiation therapy.

125. The method of embodiment 123, wherein the additional therapeutic agent comprises an immune modulating agent.

126. The method of embodiment 125, wherein the immune modulating agent is an immune checkpoint inhibitor.

127. A method of treating a tumor or cancer in a subject comprising:
(a) intravenously administering to a subject having a tumor or cancer a composition comprising a cetuximab-IR700 conjugate in a formulation comprising 10 mM sodium phosphate, 0.02% (w/v) polysorbate 80 and 9% (w/v) trehalose at pH 7.1, wherein the conjugate is administered in an amount that is or is about 640 mg/m$^2$; and
(b) after administering the conjugate, irradiating the lesion at about 24±4 hours at a wavelength of 690±20 nm at a dose of at least or at least about or about 50 J cm$^{-2}$ or 100 J/cm of fiber length, thereby treating the tumor or cancer in the subject.

128. A method of treating a head or neck cancer in a subject comprising: (a) intravenously administering to a subject having a head or neck cancer a composition comprising a cetuximab-IR700 conjugate in a formulation comprising 10 mM sodium phosphate, 0.02% (w/v) polysorbate 80 and 9% (w/v) trehalose at pH 7.1, wherein the conjugate is administered in an amount that is or is about 640 mg/m$^2$; and b) after administering the conjugate, irradiating the lesion at about 24±4 hours at a wavelength of 690±20 nm at a dose of at least or at least about or about 50 J cm$^{-2}$ or 100 J/cm of fiber length, thereby treating the cancer in the subject.

129. The method embodiment 128, wherein the composition comprises 5 mg/mL cetuximab-IR700 conjugate.

VI. EXAMPLES

The following examples are included for illustrative purposes only and are not intended to limit the scope of the invention.

Example 1: Generation of Cetuximab-IR700 Conjugate

This Example describes a method for preparing and formulating exemplary conjugates containing IR700 linked to exemplary antibodies, to produce antibody-IR700 conjugates. The provided methods are exemplary and similar methods may be employed to conjugate other antibodies to IR700. The methods were performed to limit exposure of the dye and conjugate to light due to the photosensitivity of the dye, which included the use of low levels of green light having a wavelength from 425 to 575 nm and an intensity of less than 200 Lux in the manufacturing facility. The following buffers were used for conjugation: conjugation buffer (100 mM sodium phosphate, pH 8.65), quenching buffer (1.0 M glycine, pH 9) and final phosphate buffered saline (PBS) formulation buffer: (5.60 mM Na$_2$HPO$_4$, 1.058 KH$_2$PO$_4$, 154 mM NaCl, pH 7.1).

A. Preparation of Dye and Cetuximab
1. Cetuximab Preparation

Prior to conjugation, cetuximab was filtered through a 0.22 μm filter, pooled, and stored at 2-8° C.

A concentration and buffer exchange step was then performed by ultrafiltration/diafiltration (UF/DF). The UF/DF device was cleaned and equilibrated with 100 mM sodium phosphate, pH 8.65 buffer. Prior to UF/DF operations, the pooled, filtered Cetuximab was warmed by placing it in an incubator at 25° C. for 120-150 min. The material was first concentrated to a target of 5 mg/mL and then diafiltered into 100 mM sodium phosphate, pH 8.65 buffer. The diafiltered Cetuximab product concentration was determined and then diluted to a target concentration of 2 mg/mL (1.8-2.4 mg/mL) using 100 mM sodium phosphate, pH 8.65 buffer.

2. Dye Preparation

Prior to conjugation, the IRDye 700DX NHS Ester (dye; Cat. No. 929-70011; Li-COR, Lincoln, NE) was prepared by dissolving it to a concentration of 10 mg/mL in anhydrous DMSO. The steps were performed under green light (e.g., wavelength from 425 to 575 nm and an intensity of less than 200 Lux) to protect the dye from the wavelengths of light that are strongly absorbed by the dye.

B. Conjugation

The conjugation and quenching steps were performed in a vessel or tank containing diafiltered Cetuximab, wrapped in aluminum foil for light protection. The steps were performed at room temperature under green light (e.g., wavelength from 425 to 575 nm and an intensity of less than 200 Lux) to protect the conjugate from photo-degradation.

The conjugation reaction was performed with IRDye 700DX NHS ester in DMSO, at a final molar ratio of 4:1 (IRDye 700DX NHS ester: cetuximab), to achieve incorporation of approximately 2-3 dye residues per cetuximab molecule. The IRDye 700DX NHS ester was added to the carboys containing cetuximab and mixed on a stir plate for 10-15 min. The conjugation reaction then proceeded for 120 min by placing the vessels in a 25° C. incubator.

The conjugation reaction was quenched by the addition of 1 M glycine to a final concentration of 4.2 mM and mixing for 10-12 min. The vessels were incubated for an additional 20-25 min in the 25° C. incubator.

A final UF/DF step was performed to exchange the conjugated product into the final PBS formulation buffer. The quenched conjugate was transferred to the UF/DF system and was first concentrated to 8-10 L followed by diafiltration with 8-12 diavolumes of PBS in order to exchange the product into the final formulation buffer. The protein concentration was determined and if needed, further dilution with PBS was performed to reach a final target product concentration of 2 mg/mL in PBS buffer. This starting material was used for examples below to test different formulation components.

A filtration through a 0.22 μm filter was performed and the cetuximab-IR700 conjugate was stored in the dark at 2-8° C. in a vessel covered with aluminum foil to protect the contents from light. The steps were performed at room temperature under green light to protect the cetuximab-IR700 conjugate. The resulting conjugate was submitted for SEC-HPLC analysis to determine concentration, dye to antibody ratio (DAR), identity and purity, and to determine appearance, pH, bioburden, and endotoxin levels.

Example 2: Assessment of Non-Ionic Surfactants on Agitation-Induced Aggregation of Cetuximab-IR700 Conjugate This example describes methods to assess the effect of various surfactant excipients on reducing aggregation of cetuximab-IR700. Exemplary surfactants that were assessed were non-ionic surfactants polysorbate 20 and polysorbate 80. The extent of aggregation and effect of added excipients on aggregation of cetuximab was compared.

Briefly, 2.5 mL samples of cetuximab control and cetuximab-IR700 were prepared in 15 ml conical tubes at concentrations of 20 mg/ml and 5 mg/mL, respectively. Polysorbate 20 or polysorbate 80 was added to each sample at various concentrations (w/v) as described in Table 1A and Table 1B, respectively. Samples were agitated horizontally on a MaxQ 4000 orbital shaker at 250 rpm for 8 hours at 25° C. The samples appeared cloudy after agitation. Samples were centrifuged and analyzed for visible particulates, and results are shown in Tables 1A and 1B. Samples that contained visible aggregates are labeled "+" in each table, and samples that did not contain visible aggregates are labeled "−".

Cetuximab-IR700 particulates appeared to be gelatinous in consistency. As shown in Table 1A and Table 1B, visible particulates were observed in both cetuximab and cetuximab-IR700 with no or low concentrations of surfactant. No visible particulates were observed in cetuximab-IR700 samples containing ≥0.005% polysorbate 20 or polysorbate 80 or in cetuximab control samples containing ≥0.002% polysorbate 20 or polysorbate 80.

TABLE 1A

Effects of polysorbate 20 on aggregation

| Polysorbate 20 Concentration | cetuximab | cetuximab-IR700 conjugate |
|---|---|---|
| 0.000% | + | + |
| 0.001% | + | + |
| 0.002% | − | + |
| 0.005% | − | − |
| 0.01% | − | − |
| 0.02% | − | Not tested |

TABLE 1B

Effects of polysorbate 80 on aggregation

| Polysorbate 80 Concentration | Cetuximab | Cetuximab-IR 700 conjugate |
|---|---|---|
| 0.000% | + | + |
| 0.001% | + | + |
| 0.002% | − | + |
| 0.005% | − | − |
| 0.01% | − | − |
| 0.02% | − | Not tested |

For Tables 1A and 1B: "+" refers to particulates observed through visual inspection and "−" refers to no particulates through visual inspection.

The results showed that cetuximab-IR700 was more prone to forming visible particulates when exposed to shear stress caused by agitation than cetuximab. A greater concentration of polysorbate was required to reduce aggregation, and hence preserve the stability, of cetuximab-IR700 than cetuximab.

Example 3: Size Exclusion HPLC (SE-HPLC) Analysis of Agitation-Induced Aggregation of Cetuximab-IR700 Conjugate Additional analysis using size exclusion higher performance liquid chromatography (SE-HPLC) was performed to assess the effect of the exemplary polysorbate 20 and polysorbate 80 surfactant excipients on reducing aggregation of cetuximab-IR700.

Samples of unconjugated cetuximab controls and cetuximab-IR700 were prepared in the presence or absence of various concentrations of polysorbate 20 or polysorbate 80 as described in Example 2, and the samples were agitated as described in Example 2. Additional experiments also were performed by adding higher concentrations of polysorbate 80 to the cetuximab-IR700 sample up to 0.10% (w/v). Prior to analysis by SE-HPLC, samples containing cetuximab were diluted to 2 mg/mL with 1×PBS, while samples containing cetuximab-IR700 were left undiluted at 5 mg/mL. Each sample was filtered with a precolumn 0.2 μm frit to remove large particulate matter prior to analysis by SE-HPLC.

For analysis by SE-HPLC, 20 μL of each filtered sample was run in a Shodex Protein® 5 μm KW-803 (8×300 mm, 300A) size-exclusion chromatography column on an Agilent 1100 HPLC machine. Samples were run in a 1×PBS pH 7.1 mobile phase at a flow rate of 1 mL/min for a total of 20 minutes. Samples were detected at wavelengths of 280 nm and 690 nm. The percent area of the main peak for the monomer content of the sample was determined. Percent recovery was quantified by comparing the amount contained in all peaks detected in the agitated sample to the amount detected in the untreated sample.

Figure 1B:
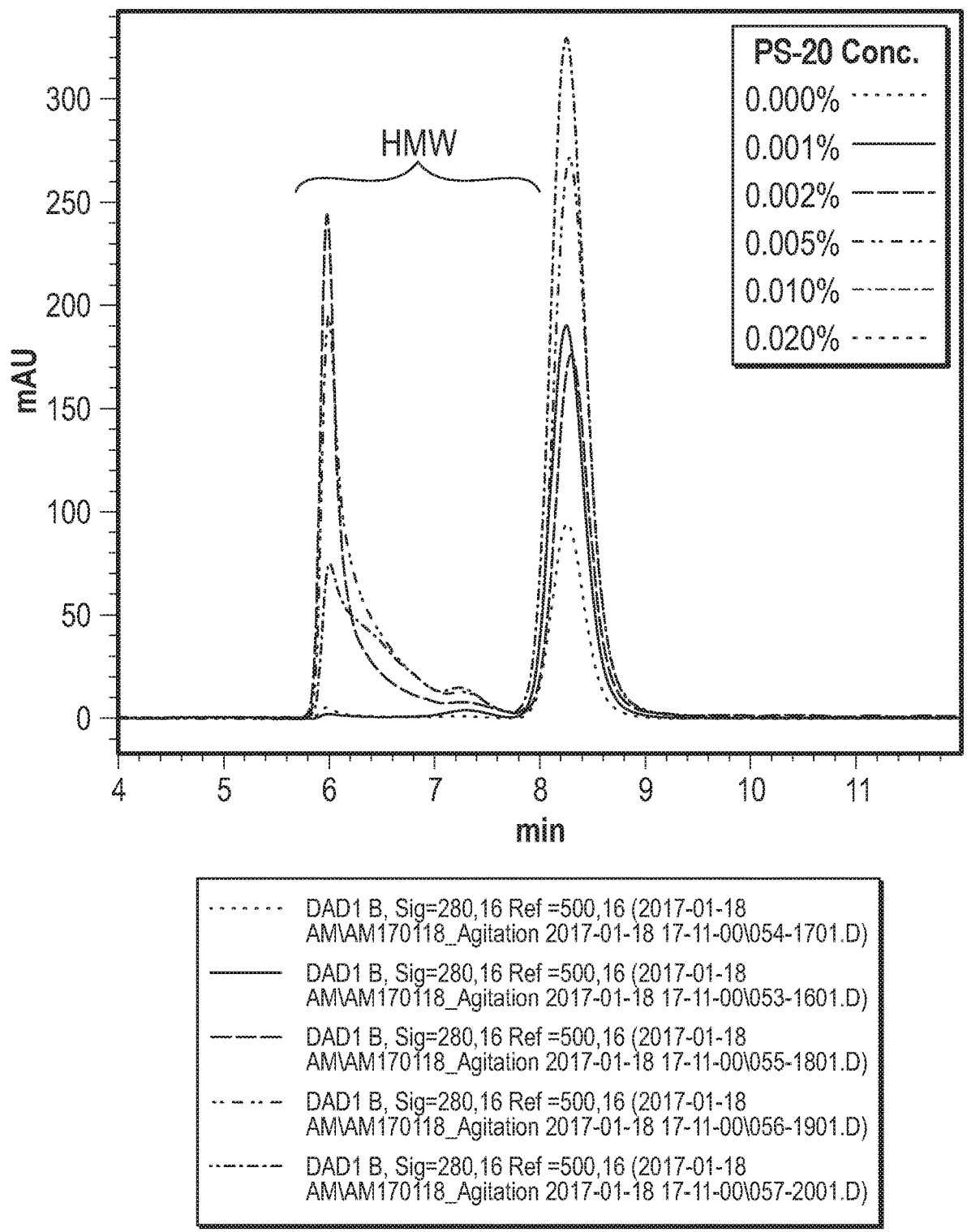
FIG. 1B displays SE-HPLC profiles for cetuximab-IR700 conjugate in the presence or absence of various concentrations of polysorbate 20. HMW corresponds to high molecular weight peaks.
Figure 1C:
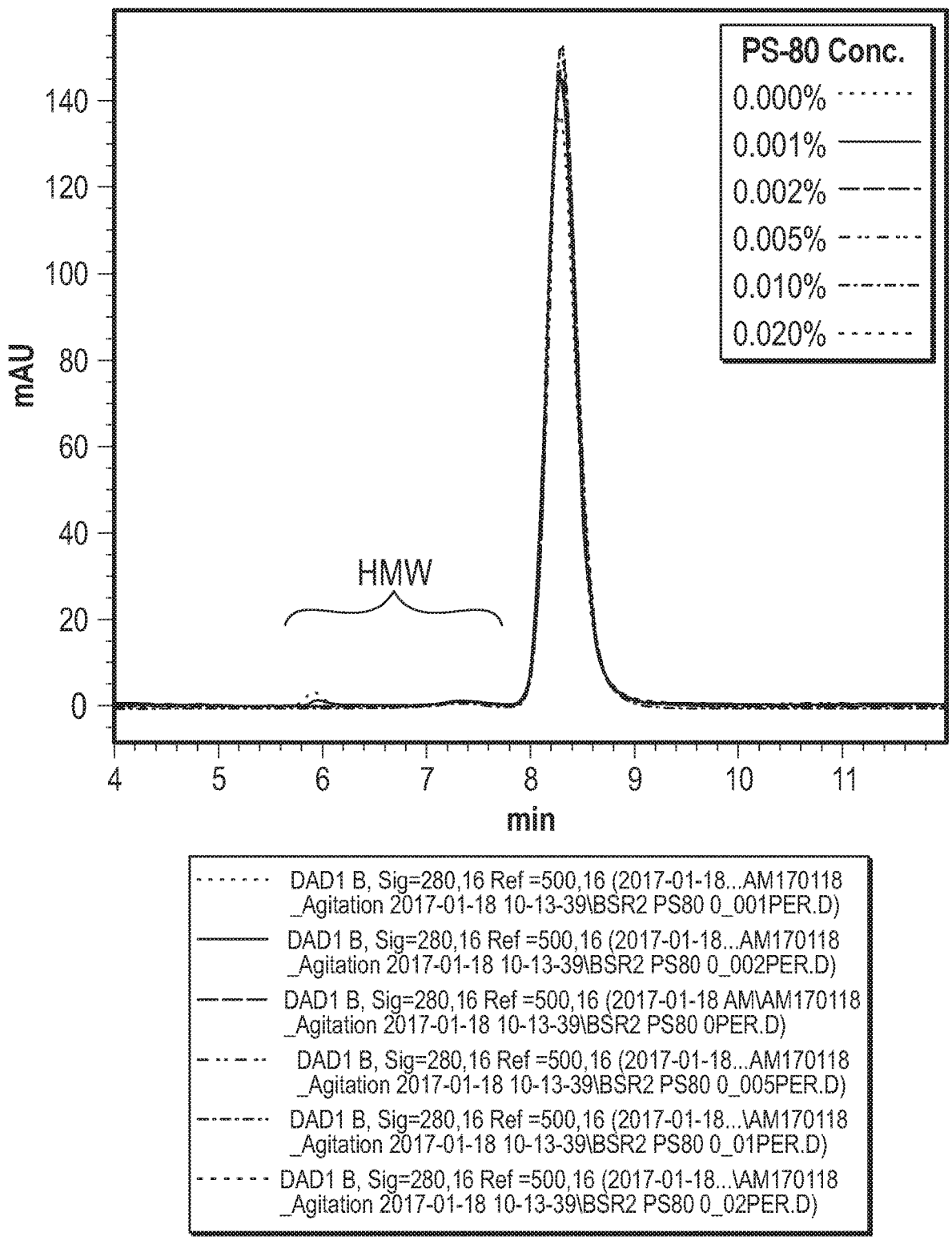
FIG. 1C displays SE-HPLC profiles for cetuximab in the presence or absence of various concentrations of polysorbate 80. HMW corresponds to high molecular weight peaks.
Figure 1D:
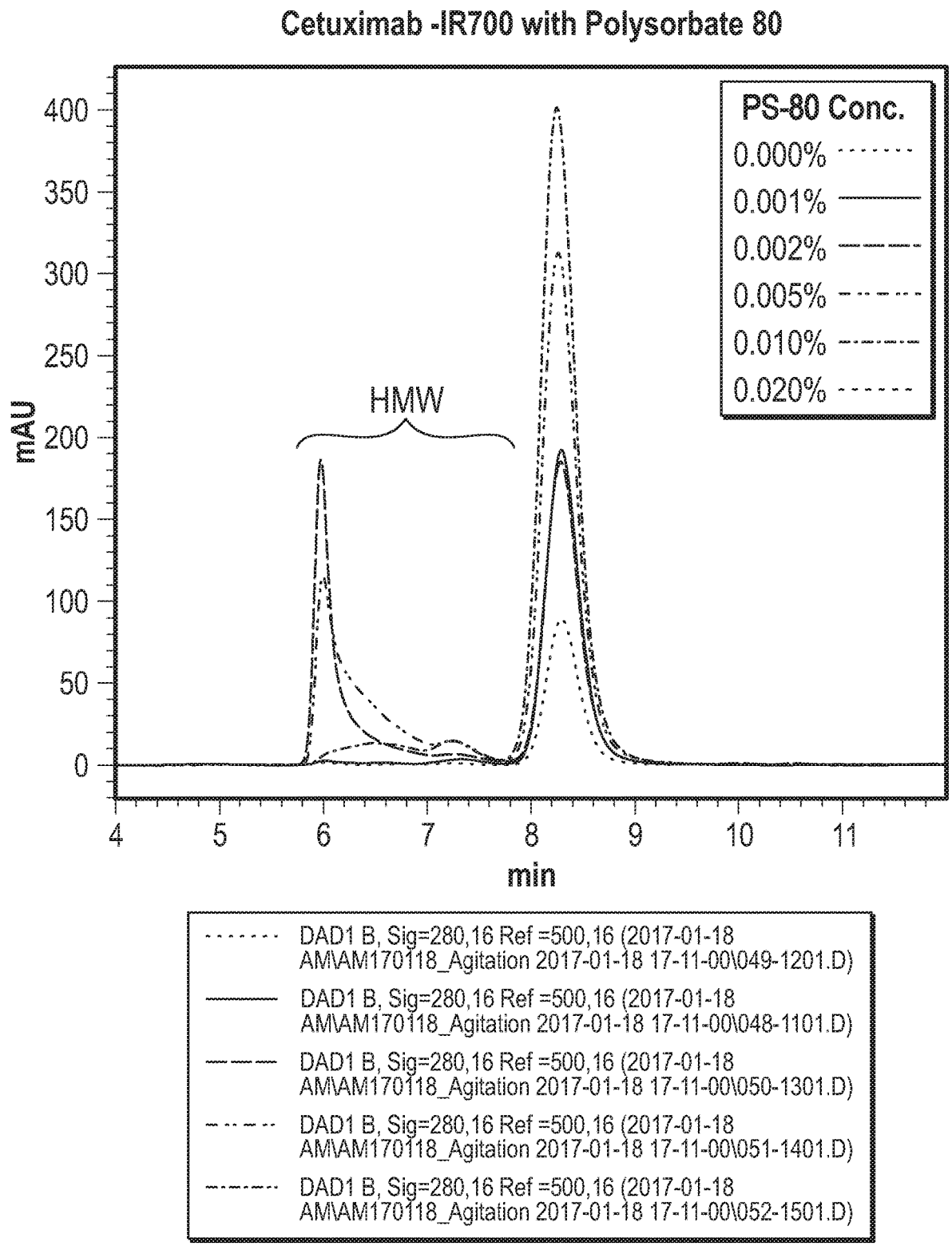
FIG. 1D displays SE-HPLC profiles for cetuximab-IR700 in the presence or absence of various concentrations of polysorbate 80. HMW corresponds to high molecular weight peaks.
Figure 1E:
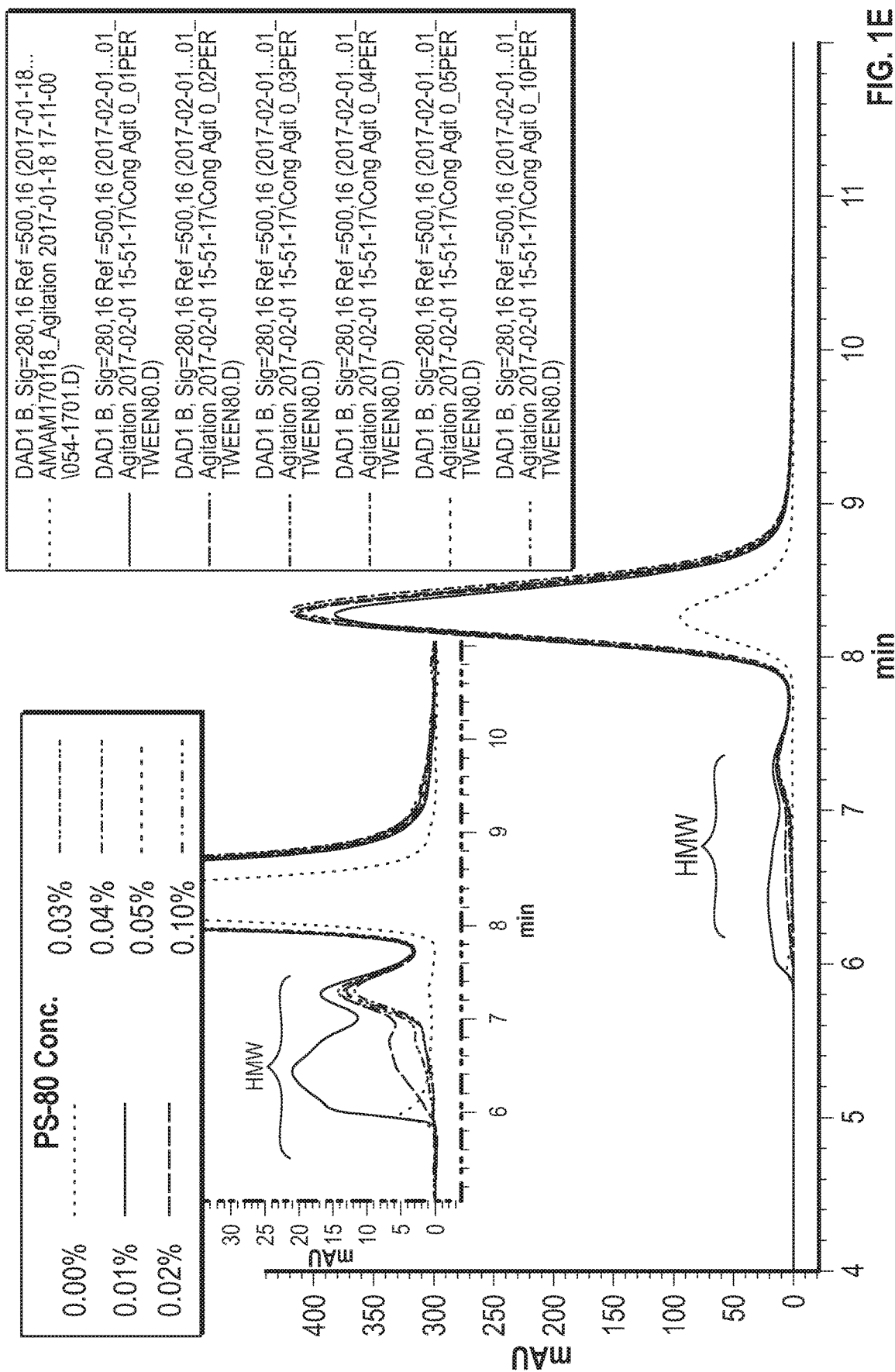
FIG. 1E displays SE-HPLC profiles for cetuximab-IR700 in the presence or absence of higher concentrations of polysorbate 80 than those shown in FIG. 1D. HMW corresponds to high molecular weight peaks. The inset is an expanded view of the HMW peaks.

Results from samples containing polysorbate 20 are shown in FIGS. 1A-1B and Table 2A, and results from samples containing polysorbate 80 are shown in FIGS. 1C-1E and in Table 2B-2C. As shown in Tables 2A-2C, recovery of both cetuximab and cetuximab-IR700 was increased as the polysorbate concentrations increased, with a polysorbate concentration at or above 0.005% substantially increasing recovery to greater than 95%, such as greater than 98%, for both cetuximab and cetuximab-IR700. This evidences that the presence of a non-ionic surfactant excipient at concentrations greater than 0.005% does not result in protein loss during agitation.

Differences, however, were observed in the SE-HPLC profiles between cetuximab and cetuximab-IR700. As shown in FIG. 1A-1E, cetuximab-IR700 samples produced broad secondary peaks corresponding to high molecular weight multimers. These secondary peaks were largest in samples containing 0.002% and 0.005% polysorbate, and were still present to some extent even at higher concentrations of polysorbate. In contrast, secondary peaks were largely absent from samples containing cetuximab regardless of polysorbate concentration. Comparing the results between polysorbate 20 and polysorbate 80 showed that polysorbate 80 was somewhat more effective than polysorbate 80 in preserving monomer content.

As shown in Table 2C and FIG. 1E, when assessing effectiveness of higher concentrations of polysorbate 80 on preserving stability, higher concentrations of polysorbate 80 were needed to preserved monomer content. The results showed that a minimum 0.04% non-ionic surfactant, such as polysorbate 80, optimizes monomer content and decreases the percentage of HMW peaks observed by SE-HPLC.

TABLE 2A

| Polysorbate 20 Concentration | cetuximab Main Peak (%) | cetuximab Recovery (%) | cetuximab-IR700 Main Peak (%) | cetuximab-IR700 Recovery (%) |
|---|---|---|---|---|
| 0.000% | 99.0 | 89.6 | 94.6 | 20.5 |
| 0.001% | 99.0 | 96.2 | 95.7 | 41.9 |
| 0.002% | 99.1 | 95.5 | 51.3 | 72.7 |
| 0.005% | 98.7 | 100.1 | 59.0 | 100.6 |
| 0.01% | 98.9 | 100.0 | 73.0 | 98.7 |
| 0.02% | 98.8 | 100.9 | Not tested | Not tested |

TABLE 2B

| Polysorbate 80 Concentration | cetuximab Main Peak (%) | cetuximab Recovery (%) | cetuximab-IR700 Main Peak (%) | cetuximab-IR700 Recovery (%) |
|---|---|---|---|---|
| 0.000% | 97.1 | 91.8 | 96.9 | 19.0 |
| 0.001% | 98.4 | 95.8 | 95.7 | 42.2 |
| 0.002% | 98.9 | 96.9 | 59.2 | 66.0 |
| 0.005% | 98.8 | 99.5 | 68.6 | 99.1 |
| 0.01% | 98.3 | 101.3 | 90.1 | 99.0 |
| 0.02% | 98.8 | 101.9 | Not tested | Not tested |

TABLE 2C

| Polysorbate 80 Concentration | cetuximab-IR700 Main Peak (%) | cetuximab-IR700 Recovery (%) |
|---|---|---|
| 0.000% | 94.6 | 21.0 |
| 0.010% | 85.6 | 100.1 |
| 0.020% | 93.8 | 100.1 |
| 0.030% | 95.5 | 100.1 |
| 0.040% | 96.5 | 99.8 |
| 0.050% | 96.3 | 99.2 |
| 0.100% | 96.2 | 99.9 |

These experiments show that polysorbate 20 and polysorbate 80 can be used to reduce aggregation caused by agitation in cetuximab and cetuximab-IR700 samples. The results also show that polysorbate 80 may be more effective than polysorbate 20 in preserving monomer content.

Example 4: pH Stability of Drug Product

To assess the effect of pH, concentration and/or buffer formulation on long term stability of the conjugate, a series of four buffer formulations containing the cetuximab-IR700 conjugate at two concentrations, 2 mg/mL and 5 mg/mL, for a total of eight buffer formulations were prepared at either pH 5.5 or pH 7.1. The eight buffer formulations prepared were as follows:

BF #1: [2 mg/mL conjugate] HyClone Phosphate Buffered Saline (1×), 6.7 mM PO$_4$ (pH 7.0-7.2) without Calcium, Magnesium (HyClone Cat #SH30256).

BF #2: [2 mg/mL conjugate] 10 mM Sodium citrate, 100 mM glycine, 100 mM NaCl, 0.01% Tween 80, pH 5.5±0.1

BF #3: [2 mg/mL conjugate] 20 mM Sodium Citrate, 120 mM Sodium Chloride, 2 mM EDTA, 0.01% Tween 80, pH 5.5±0.1

BF #4: [2 mg/mL conjugate] 20 mM Sodium Citrate, 4% Mannitol, 2 mM EDTA, 0.01% Tween 80, pH 5.5±0.1

BF #5: [5 mg/mL conjugate] HyClone Phosphate Buffered Saline (1×), 6.7 mM PO$_4$ (pH 7.0-7.2) without Calcium, Magnesium (HyClone Cat #SH30256).

BF #6: [5 mg/mL conjugate] 10 mM Sodium Citrate, 100 mM glycine, 100 mM NaCl, 0.01% Tween 80, pH 5.5±0.1

BF #7: [5 mg/mL conjugate] 20 mM Sodium Citrate, 120 mM Sodium Chloride, 2 mM EDTA, 0.01% Tween 80, pH 5.5±0.1

BF #8: [5 mg/mL conjugate] 20 mM Sodium Citrate, 4% Mannitol, 2 mM EDTA, 0.01% Tween 80, pH 5.5±0.1

In this example, stability was performed on BF #5-BF #8 using conditions to induce forced degradation as follows. A sample volume of 750 μL of each of the 4 formulations BF #5-8 were placed into 2 mL screw-cap polypropylene vials and covered with aluminum foil to protect the samples from light. The four tubes were placed into a 45° C. water bath and allowed to incubate for 16 hours. The vials were then transferred to a refrigerator and stored at 2-8° C. for a period of 1 week. The samples were removed from the refrigerator and centrifuged at 5,000×g for 5 minutes. Upon inspection of the tubes it was observed that the 3 samples of cetuximab-IR700 conjugate formulated in the pH 5.5 buffers systems (BF #6, BF #7 and BF #8) all had a significant amount of precipitated blue material in the bottom of each tube. However, the BF #5 sample which was formulated in PBS at pH=7.1 did not show any visual precipitate.

A sample of the supernatant solution was obtained from each of the four samples and HPLC-SEC analysis was performed to determine the concentration of the monomer form of the cetuximab-IR700 conjugate that remained in each of the samples. The results of that analysis are shown below in Table 3 along with the initial concentrations determined for each of samples prior to being subjected to the forced degradation study conditions.

TABLE 3

Forced Degradation Study Results

| Sample | Initial Concentration (mg/mL) | Final Concentration (mg/mL) |
| --- | --- | --- |
| BF#5 | 5.2 | 5.1 |
| BF#6 | 5.3 | 3.7 |
| BF#7 | 5.3 | 4.1 |
| BF#8 | 5.2 | 3.6 |

The data in Table 3 show that all samples of the cetuximab-IR700 conjugate formulated in the pH 5.5 buffers systems (BF #6, BF #7 and BF #8) displayed a significant loss (20% or more) in the concentration of the monomer form of the conjugate product. In contrast to these results, the BF #5 (pH=7.1) sample showed little change in concentration. These results indicated that the cetuximab-IR700 conjugate drug product could also be less stable in pH=5.5 buffer systems upon long term storage (e.g., greater than 6 months) of the product under 2-8° C. storage conditions.

Example 5: Long Term Storage Stability of Cetuximab-IR700 Conjugate in pH=5.5 Buffer Systems Versus pH=7.1 PBS Samples of the cetuximab-IR700 conjugate in the four buffer formulations described above containing the conjugate at the two concentrations, 2 mg/mL and 5 mg/mL (BF #1-8), were stored for a period of 12 months at 2-8° C. protected from light in 15 mL polypropylene tubes. After the 12 months of storage at 2-8° C. the samples were visually inspected for the formation of a precipitate. It was observed upon this inspection that all of the pH=5.5 samples (BF #2, BF #3, BF #4, BF #6, BF #7 and BF #8) contained a significant amount of insoluble blue material that had adhered to the bottom and sides of their storage tubes. Conversely, the two samples in the PBS pH=7.1 buffer system (BF #1, BF #5) did not show any indication of insoluble material. This observation indicates that the cetuximab-IR700 conjugate is not stable and can precipitate after long-term storage in a buffer system at a pH<6, even at temperatures of 2-8° C. and protected from light. In contrast, the cetuximab-IR700 conjugate that was formulated in a buffer greater than pH 6.0, such as about pH 7.1, results in stability of the drug product even after long-term storage at 2-8° C. for up to 1 year.

Example 6: Screening of the Stability of Various Formulations Containing Cetuximab-IR700 Conjugate Under Thermal Stress Conditions Various liquid formulations containing cetuximab-IR700 conjugates were screened for attributes to identify formulations that provide for conjugate stability under control storage conditions and thermal stress conditions.

Cetuximab-IR700 conjugates were generated using Cetuximab preparations from an independent source conjugated to IR700 generally as described in Example 1. Various liquid formulations containing the conjugate, including formulations of different pH, formulations containing various buffering agents and various excipients such as different protectants, were evaluated for the following attributes: appearance by visual inspection; thermal melting profile determination by differential scanning calorimetry (DSC); and concentration, purity, dye-to-antibody ratio (DAR) by size exclusion high performance liquid chromatography (SE-HPLC; also referred to as HPLC-SEC). DSC was performed by temperature ramping at 1° C./min from 20° C. to 100° C. with the samples at 1 mg/mL in corresponding buffers.

Visual inspection was performed to confirm the green to blue color of the formulation, in a room with subdued lighting, to protect the conjugates from light. The presence of visible particulates was also noted.

SE-HPLC was performed under isocratic conditions, detecting absorbance at 690 nm (A690) and 280 (A280) nm, to assess purity and impurity content (at A690 and A280), free dye content (at A690) and dye-to-antibody ratio (DAR; A690 and A280). For IR680 dye conjugates, concentration and DAR was performed at 672 nm (A672) and for IR800 conjugates, concentration and DAR was performed at 767 nm (A767). The percentage of monomers, high molecular weight (HMW) species, low molecular weight (LMW) species, and free IR700 dye were determined by analyzing the chromatograms at A690 and A280 nm. Percent (%) purity or % impurity was calculated by area normalization, determining the % fraction of monomer, HMW and LMW conjugate species in the sum of all peaks. Percent (%) free dye impurity was determined by area normalization, determining the % fraction of the free dye in the sum of all A690 peaks, including the free dye peak. Dye-to-antibody ratio (DAR) was determined by exploiting the different absorptive properties of the protein and dye in the conjugated product. A correction factor ($CF_\varepsilon$) was used to account for the differences in the molar extinction coefficients ($\varepsilon$) between the antibody at A280 and the IR700 dye at A690. Absorbance at A280 was corrected to account for the contribution of the dye in the A280 measurement. The following equation was used to calculate DAR:

DAR=(A690/A280corr)×$CF_\varepsilon$, where:

A690=the peak area for the conjugate at A690

A280corr=A280−(A690×0.095)

$CF_\varepsilon$=1.16=$\varepsilon$280Ab/$\varepsilon$690dye=217,440 $M^{-1}$ $cm^{-1}$/187,000 $M^{-1}$ $cm^{-1}$ $\varepsilon$=Extinction Coefficient The condition used for SE-HPLC are listed in Table 4.

TABLE 4

| SE-HPLC Conditions | |
| --- | --- |
| Method Parameter | Condition/Requirement |
| Mobile Phase | Phosphate buffered saline, pH 7.1 |
| Flow Rate | 0.5 mL/min |
| Column | Shodex Protein KW-803 |
| Nominal Column Load | 100 μg |
| Detector Wavelength | 280 nm and 690 nm |
| Run Time | 20 min |
| Elution Mode | Isocratic |
| Temperature | 25 ± 2° C. |
| Autosampler Temperature | 4 ± 2° C. |

A. Initial Screen of Formulations Containing Various Buffers and Stabilizing Agents Attributes of formulations containing cetuximab-IR700 conjugates formulated with various buffering agents with buffering capacity ranging from pH 6.0 to 7.5 and various protectants, including sodium chloride, arginine-succinate, and trehalose were evaluated (see Table 5). Each formulation was incubated under thermal stress (40° C.) conditions for two weeks and assessed for stability of the cetuximab-IR700 conjugates in each formulation, by determining monomer content by SE-HPLC and determining melting temperature profiles by DSC.

Figure 2:
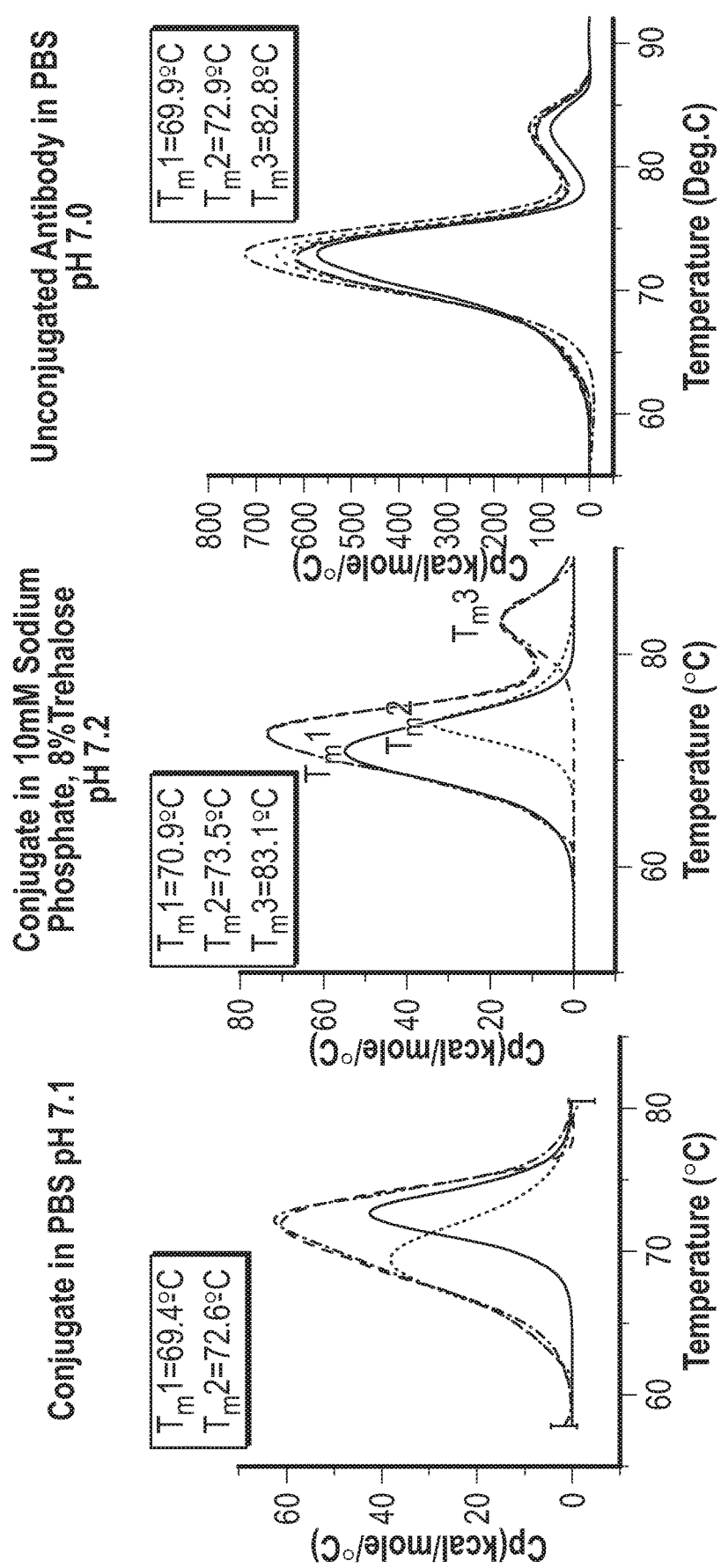
FIG. 2 displays melting temperature profiles for the cetuximab-IR700 conjugate in various conditions and for the unconjugated cetuximab.

The various formulations tested and the results are shown in Table 5 and exemplary melting temperature profiles are shown in FIG. 2. As shown, formulations containing arginine-succinate and buffered at pH 6.5 and lower exhibited greater chemical degradation, as assessed by an increase in high molecular weight (HMW) aggregates, compared to formulations containing other excipients and higher pH. As shown in FIG. 2, formulations containing trehalose exhibited improved the thermal melting profile for the conjugate, comparable to those of the unconjugated antibody. The results indicated that cetuximab-IR700 was more stable at higher pH and in liquid formulations containing stabilizing protectants such as trehalose.

B. Selection of Surfactant Concentrations

Size exclusion high performance liquid chromatography (SE-HPLC) was performed to assess the effect of the various concentrations of non-ionic surfactant excipient on the aggregation of the cetuximab-IR700 conjugates in formulations containing the protectant trehalose.

Cetuximab-IR700 conjugates, generated as described above, were formulated at 5 mg/mL in 10 mM sodium phosphate buffer, pH 7.1, 9% Trehalose, and containing various concentrations of the non-ionic surfactant polysorbate 80 (PS-80). The formulations were agitated horizontally on a MaxQ 4000 orbital shaker at 250 rpm for 8 hours at 25° C. The effect of agitation on the stability of the conjugate was assessed by determining monomer content after agitation by SE-HPLC, generally as described above. Percent recovery was determined by comparing the amount contained in all peaks detected in the agitated sample to the amount detected in the untreated sample.

Figure 3:
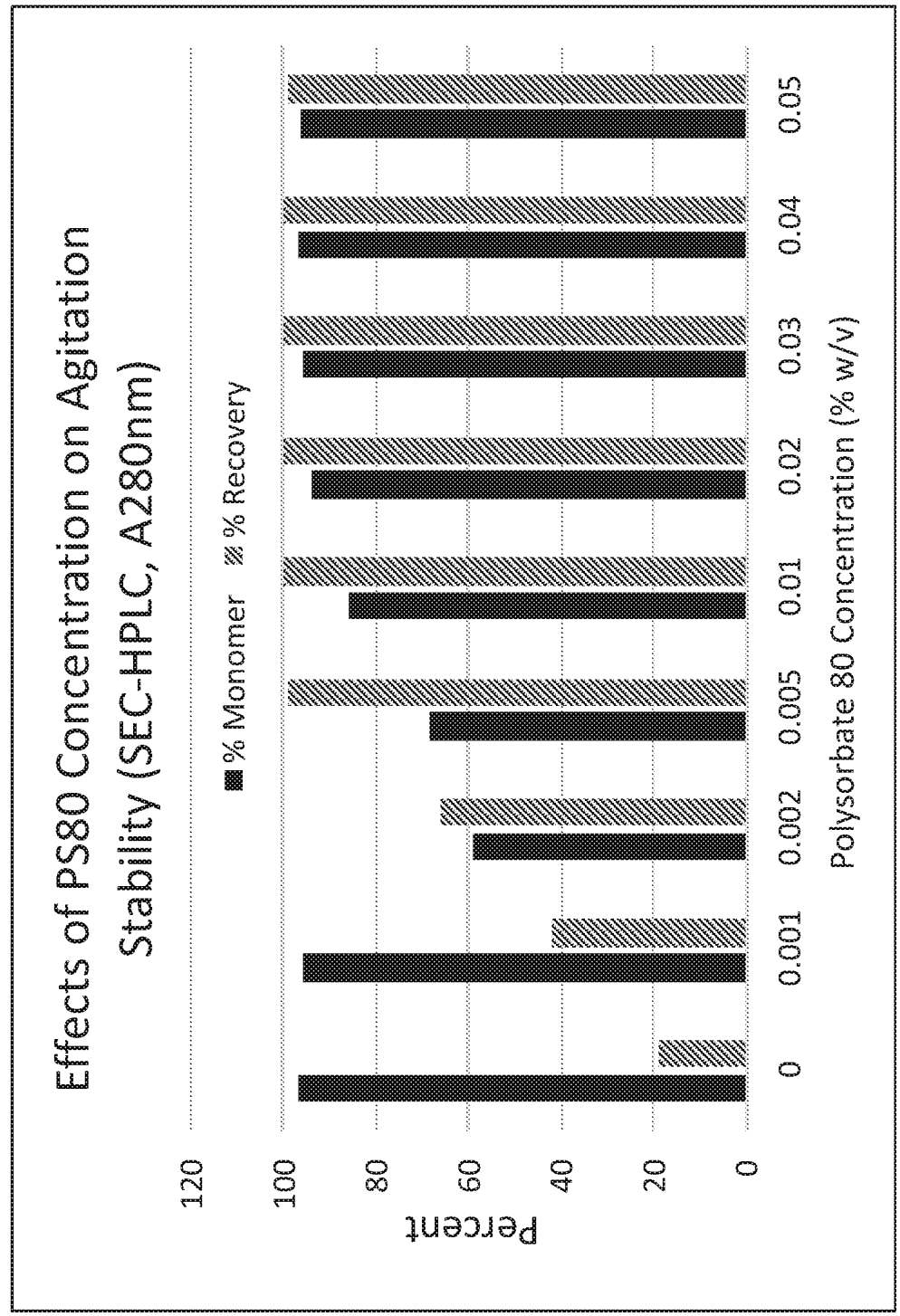
FIG. 3 displays size exclusion high performance liquid chromatography (SE-HPLC) for the cetuximab-IR700 conjugate in formulations with various concentrations of non-ionic surfactant.

The results are shown in FIG. 3. An increase in cetuximab-IR700 aggregation (reduction in monomer content) in low polysorbate 80 concentrations and a loss of total protein (reduction in % recovery) in the absence of polysorbate 80 were observed, when the formulations were subject to agitation. The presence of polysorbate 80 at 0.02% or higher

TABLE 5

Cetuximab-IR700 Stability in Various Formulations Following Thermal Stress

| pH | Buffering Agent | Protectant | Monomer Content by SE-HPLC A280 nm (%) | HMW Content by SE-HPLC A280 nm (%) | DAR by SE-HPLC | DSC |
|---|---|---|---|---|---|---|
| 6.0 | 10 mM Histidine | 100 mM Sodium Chloride, 2% Trehalose | 83.7 | 16.3 | 1.5 | NT |
| 6.0 | | 300 mM Arginine-Succinate | 89.1 | 10.9 | 2.2 | NT |
| 6.5 | 10 mM Histidine | 100 mM Sodium Chloride, 2% Trehalose | 89.5 | 10.5 | 2.1 | NT |
| 6.5 | 10 mM Citrate | 100 mM Sodium Chloride, 2% Trehalose | 93.7 | 6.3 | 2.5 | NT |
| 6.5 | 10 mM Citrate | 8% Trehalose | 93.9 | 6.1 | 2.4 | $T_m1 = 70.3°$ C. $T_m2 = 74.1°$ C. $T_m3 = 83.0°$ C. |
| 6.5 | 10 mM Citrate | 50 mM Sodium Chloride, 2% Trehalose | 93.3 | 6.7 | 2.4 | $T_m1 = 69.5°$ C. $T_m2 = 73.0°$ C. |
| 6.5 | 10 mM Citrate | 250 mM Sodium Chloride, 2% Trehalose | 94.1 | 5.9 | 2.6 | $T_m1 = 68.8°$ C. $T_m2 = 73.3°$ C. |
| 7.0 | 10 mM Tris | 100 mM Sodium Chloride, 2% Trehalose | 93.7 | 6.3 | 2.5 | $T_m1 = 69.0°$ C. $T_m2 = 73.4°$ C. |
| 7.0 | | 300 mM Arginine-Succinate | 87.0 | 13.0 | 2.6 | NT |
| 7.2 | 10 mM Sodium Phosphate | 8% Trehalose | 93.6 | 6.4 | 2.7 | $T_m1 = 70.9°$ C. $T_m2 = 73.5°$ C. $T_m3 = 83.1°$ C. |
| 7.2 | 10 mM Sodium Phosphate | 100 mM Sodium Chloride, 2% Trehalose | 93.1 | 6.9 | 2.7 | $T_m1 = 70.3°$ C. $T_m2 = 72.9°$ C. |
| 7.5 | 10 mM Tris | 100 mM Sodium Chloride, 2% Trehalose | 94.2 | 5.8 | 2.7 | $T_m1 = 70.4°$ C. $T_m2 = 73.4°$ C. |

SE-HPLC, Size Exclusion High Performance Liquid Chromatography; A280, Absorbance at 280 nm; HMW, High molecular weight species; DAR, Dye-to-antibody ratio; DSC, Differential scanning calorimetry; NT, Not tested was observed to protect against aggregation and precipitation under thermal and agitation stress conditions.

C. Selection of Conjugate Concentrations

The effect of the concentration of the cetuximab-IR700 conjugates in the formulation on the stability of the conjugates was evaluated. Cetuximab-IR700 conjugates, generated as described above, were formulated in PBS (phosphate buffered saline) at pH 7.1 at concentrations ranging from 2 mg/mL, 5 mg/mL and 10 mg/mL and incubated at control storage conditions (5° C.) or thermal stress conditions (40° C.) for two weeks. Monomer content was assessed by SE-HPLC, generally as described above.

Figure 4:
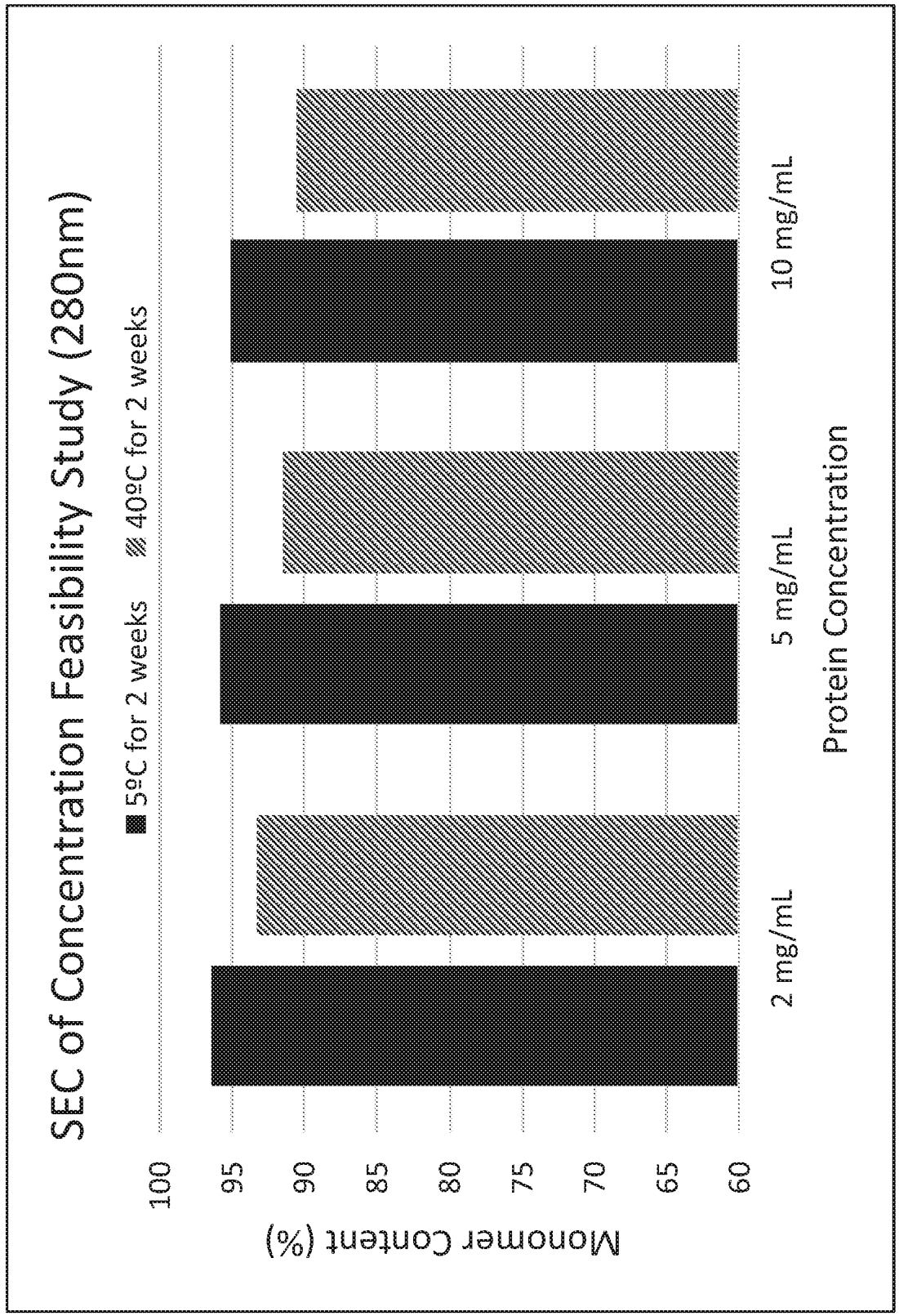
FIG. 4 displays the effect of concentration of the cetuximab-IR700 conjugates in the formulation on the stability of the conjugates.

As shown in FIG. 4, a concentration-dependent increase in high molecular weight (HMW) aggregate formation and concomitant decrease in monomer concentration was observed. The monomer content of the cetuximab-IR700 conjugate formulated at 5 mg/mL following a 2-week storage at 5° C. was comparable to that of the cetuximab-IR700 conjugate formulated at 2 mg/mL. The monomer content of the cetuximab-IR700 conjugate formulated at 10 mg/mL was lower compared to conjugates formulated at 2 mg/mL or 5 mg/mL, indicating that 5 mg/mL is a concentration that is sufficient for therapeutic dose requirements while providing stability of the conjugate in the formulation.

D. Additional Screen of Formulations Containing Various Buffers and Stabilizing Agents An additional study was performed to evaluate formulations with various pH conditions, buffers and protectants for long-term stability of the cetuximab-IR700 conjugates under thermal stress conditions and for the robustness of the various formulations.

For this study, cetuximab-IR700 conjugates were formulated with a pH ranging from 7.1-7.6, and with various protectants and surfactants (see Table 6), some of which were observed to be associated with conjugate stability in the initial screen described above in Example 6A. Cetuximab-IR700 conjugates were dialyzed into the various formulation conditions and normalized to 3 mg/mL concentration. The formulations were stored in amber vials for two weeks at control storage conditions (5° C.) or thermal stress conditions (40° C.).

The various formulations tested and the results from the SE-HPLC analysis of monomer concentrations is shown in Table 6. Compositions containing sodium phosphate buffers and trehalose or sucrose, with or without Polysorbate 80 resulted in less than 10% HMW aggregate after two weeks of 40° C. storage. The most stable formulation as assessed by SE-HPLC contained 10 mM sodium phosphate buffer and 9% trehalose, pH 7.1. Buffers containing sodium chloride showed increased HMW aggregation compared to buffers with trehalose, sucrose or sorbitol. Stability in sucrose containing formulation was comparable to those containing trehalose. Trehalose was preferred over sucrose to avoid potential glycation of the cetuximab-IR700 by sucrose. The presence of polysorbate 80 or polysorbate 20 did not impact HMW formation. Apparent differences in stability in the presence of polysorbate 80 or polysorbate 20 were due to the tris buffering agent or the presence of sodium chloride. As described in Examples 2 above, a lower concentration of polysorbate 80 was required to preserve monomer stability compared to polysorbate 20; and polysorbate 80 minimized the effects of interfacial stress.

TABLE 6

Cetuximab-IR700 Stability in Additional Formulations Following Thermal Stress

| pH | Buffering Agent (10 mM) | Protectant | Surfactant | Monomer Content by SE-HPLC-A280 nm (%) | HMW Content by SE-HPLC-A280 nm (%) | DAR by SE-HPLC |
|---|---|---|---|---|---|---|
|  | Control, PBS pH 7.1 |  | — | 84.9 | 14.1 | 3.1 |
| 7.1 | 10 mM Sodium Phosphate | 9% trehalose | — | 90.7 | 8.4 | 3.3 |
| 7.3 | 10 mM Sodium Phosphate | 9% trehalose | — | 88.9 | 10.2 | 3.3 |
| 7.6 | 10 mM Sodium Phosphate | 9% trehalose | — | 88.3 | 10.7 | 3.3 |
| 7.3 | 10 mM Tris | 9% trehalose | — | 86.6 | 11.8 | 3.0 |
| 7.3 | 10 mM Sodium Phosphate | 2% trehalose | — | 85.8 | 13.1 | 3.2 |
| 7.3 | 10 mM Sodium Phosphate | 250 mM NaCl | — | 83.7 | 15.4 | 3.2 |
| 7.3 | 10 mM Sodium Phosphate | 100 mM NaCl | — | 84.7 | 14.4 | 3.2 |
| 7.3 | 10 mM Sodium Phosphate | 100 mM NaCl + 2% trehalose | — | 85.1 | 13.9 | 3.2 |
| 7.3 | 10 mM Sodium Phosphate | 9% sucrose | — | 89.7 | 9.4 | 3.2 |
| 7.3 | 10 mM Sodium Phosphate | 5% sorbitol | — | 88.5 | 10.4 | 3.2 |
| 7.3 | 10 mM Sodium Phosphate | 9% trehalose | 0.01% polysorbate 80 | 88.8 | 9.9 | 3.2 |
| 7.3 | 10 mM Sodium Phosphate | 9% trehalose | 0.05% polysorbate 80 | 88.0 | 11.1 | 3.2 |
| 7.3 | 10 mM Sodium Phosphate | 9% trehalose | 0.01% polysorbate 20 | 87.6 | 11.4 | 3.2 |
| 7.3 | 10 mM Sodium Phosphate | 100 mM NaCl | 0.01% polysorbate 20 | 83.4 | 15.7 | 3.2 |

TABLE 6-continued

Cetuximab-IR700 Stability in Additional Formulations Following Thermal Stress

| pH | Buffering Agent (10 mM) | Protectant | Surfactant | Monomer Content by SE-HPLC-A280 nm (%) | HMW Content by SE-HPLC-A280 nm (%) | DAR by SE-HPLC |
|---|---|---|---|---|---|---|
| 7.3 | 10 mM Tris | 5% sorbitol | 0.01% polysorbate 80 | 85.3 | 13.7 | 3.2 |
| 7.3 | 10 mM Tris | 100 mM NaCl | — | 83.8 | 14.8 | 3.1 |

SE-HPLC, Size Exclusion High Performance Liquid Chromatography; A280, Absorbance at 280 nm; HMW, High molecular weight species; DAR, Dye-to-antibody ratio; —, not included Based on the results above, an exemplary cetuximab-IR700 liquid formulation was generated, containing 10 mM sodium phosphate, pH 7.1, 9% Trehalose, 0.02% Polysorbate 80 (w/v), 5.0 mg/mL cetuximab-IR700.

Example 7: Evaluation of Formulations Containing Various Cetuximab Dye Conjugates Under Thermal Stress Conditions Exemplary liquid formulations containing various cetuximab dye conjugates were assessed under thermal stress (40° C.) conditions.

Cetuximab was conjugated to NIR dyes IRDye 680RD (cetuximab-IR680), using the same general protocol as described in Example 1, with the following modifications. A sample of cetuximab was incubated with 4 molar equivalents of IRDye 680RD (Cat. No. 929-70050; Li-COR, Lincoln, NE) dissolved at 5 mg/mL in DMSO. All other step in the conjugation, purification and characterization process for the conjugate were identical to that described above for the cetuximab-IR700 conjugate preparation (Example). For the additional conjugates, cetuximab was conjugated to IRDye800 CW (cetuximab-IR800), as follows: a sample of cetuximab was incubated with 5 molar equivalents of IRDye 800CW-NHS (in 10 mg/mL DMSO) at room temperature for 1 hour. The reaction was quenched by the addition of 100 µL of 1M glycine solution (pH=9). The conjugate product was exchanged and purified using 10 reaction volumes of PBS (pH=7.1) filtered through Amicon® Ultra 15 Centrifugal Filter Units.

The conjugates were formulated in either phosphate buffered saline (PBS), pH 7.1, at 2.0 mg/mL conjugate concentration ("PBS"), or 10 mM sodium phosphate, pH 7.1, 9% trehalose, 0.02%, polysorbate 80 (w/v), at 5.0 mg/mL conjugate concentration ("trehalose PS-80 formulation"). The conjugates in the formulations were evaluated for thermal melting profile determination by differential scanning calorimetry (DSC), performed by temperature ramping 1° C./min from 20° C. to 100° C. with protein concentration at 1 mg/mL in corresponding buffers, and high pressure liquid chromatography using a size exclusion column (HPLC-SEC) analysis after incubation at 40° C. (thermal stress) or 5° C. (control) for 1 month.

Figure 5A:
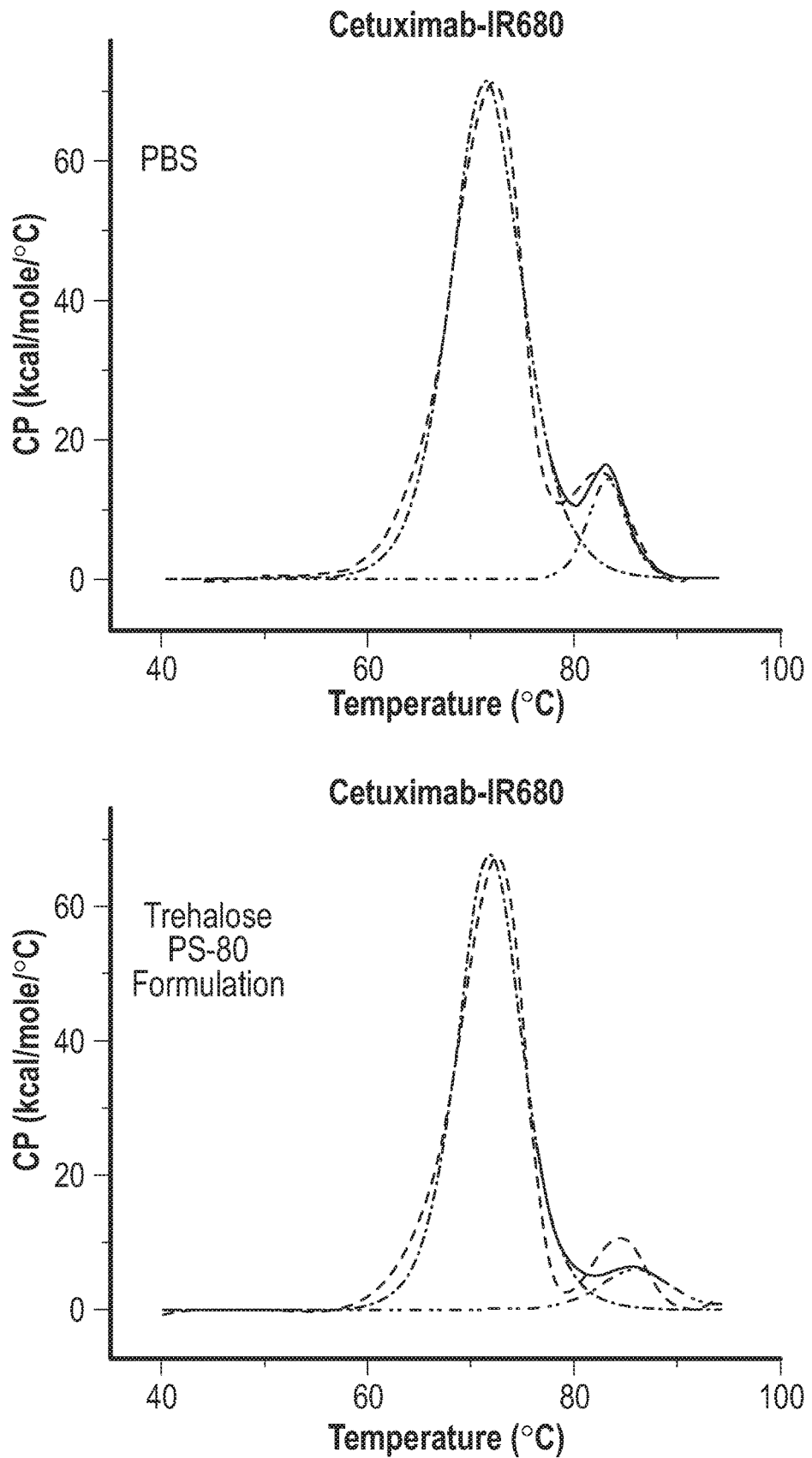
FIGS. 5A-5C displays DSC profiles cetuximab-IR680 (FIG. 5A), cetuximab-IR700 (FIG. 5B) and cetuximab-IR800 (FIG. 5C), formulated in PBS or in trehalose and Polysorbate 80 formulation.
Figure 5B:
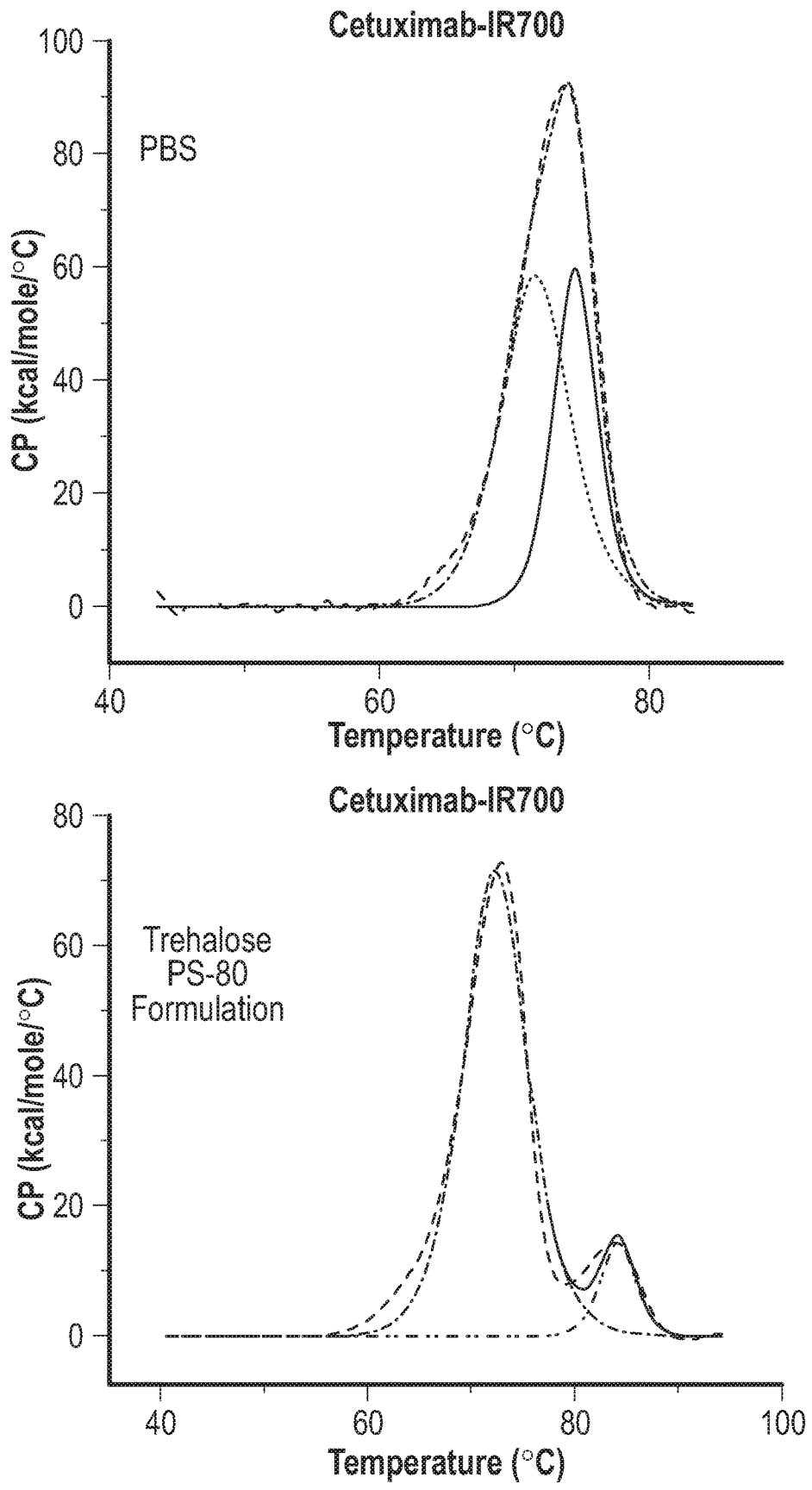
Figure 5C:
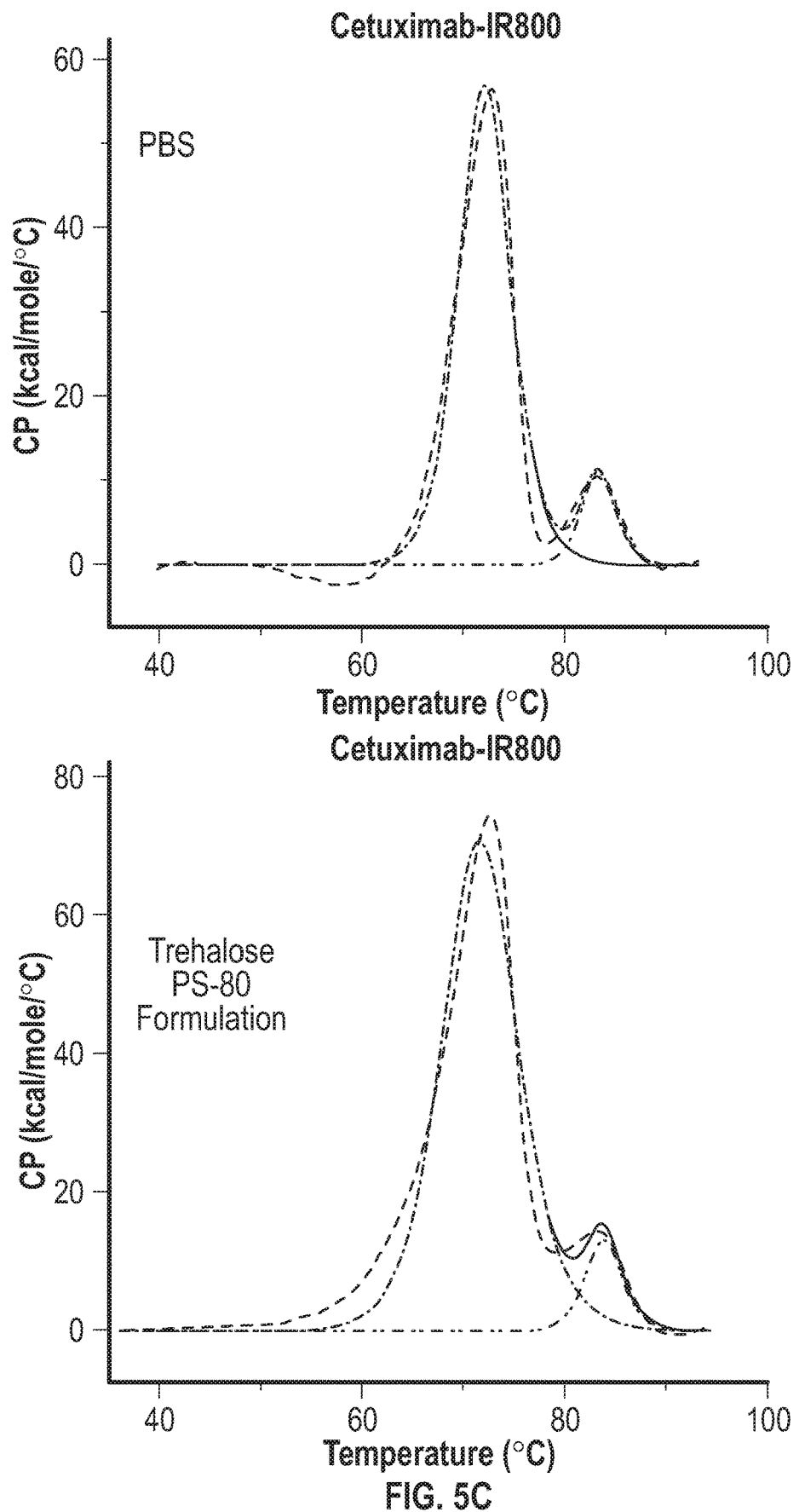

FIGS. 5A-5C shows the DSC profiles for cetuximab-IR680 (FIG. 5A), cetuximab-IR700 (FIG. 5B) and cetuximab-IR800 (FIG. 5C), formulated in PBS or in the trehalose PS-80 formulation. The results showed that the DSC profile of cetuximab-IR700 in PBS was different compared to the DSC profiles of unconjugated cetuximab, cetuximab-IR680 and cetuximab-IR800. The trehalose PS-80 formulation restored the DSC profile of cetuximab-IR700 to a profile similar to the DSC profile of unconjugated cetuximab.

Figure 6A:
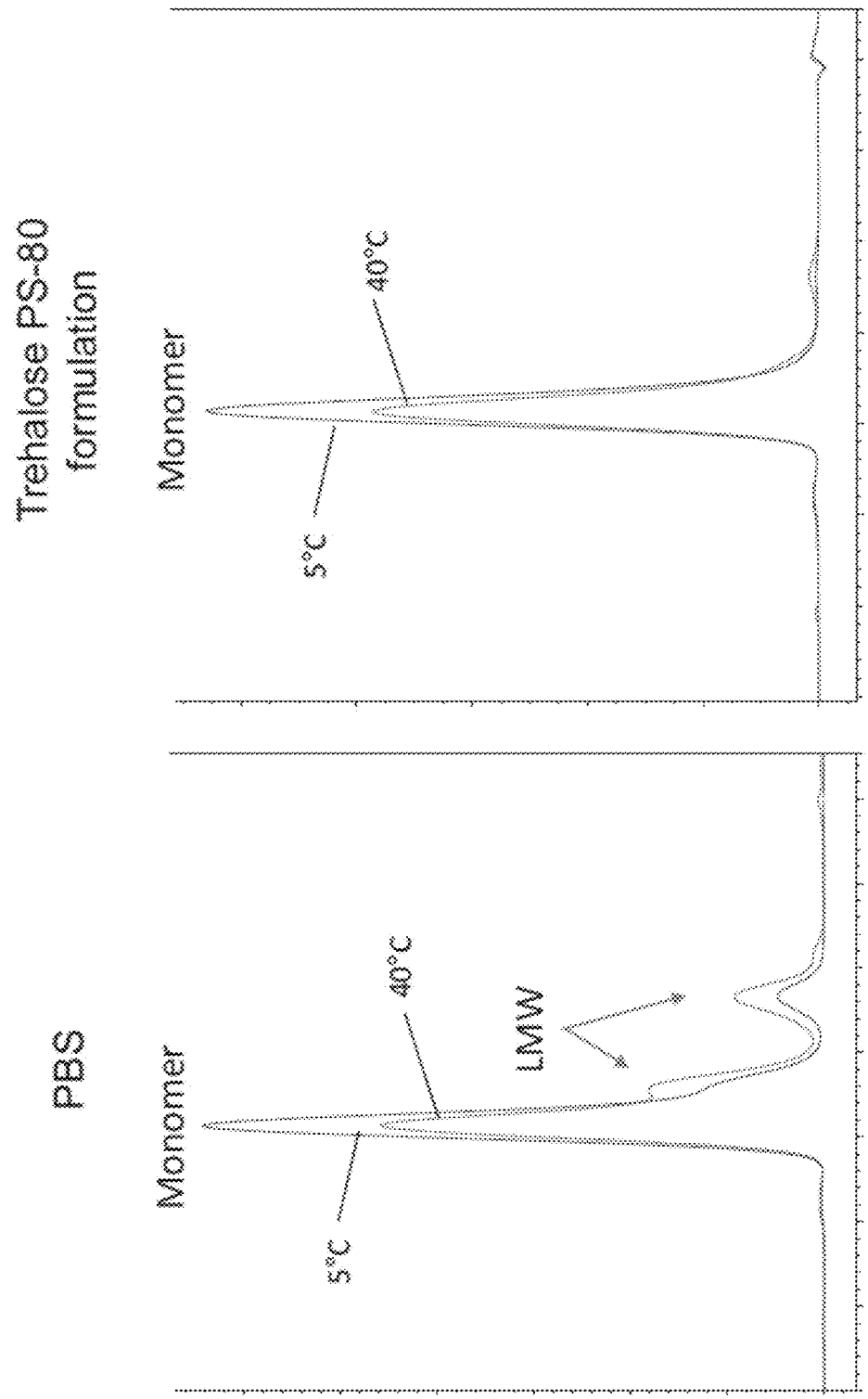
Figure 6B:
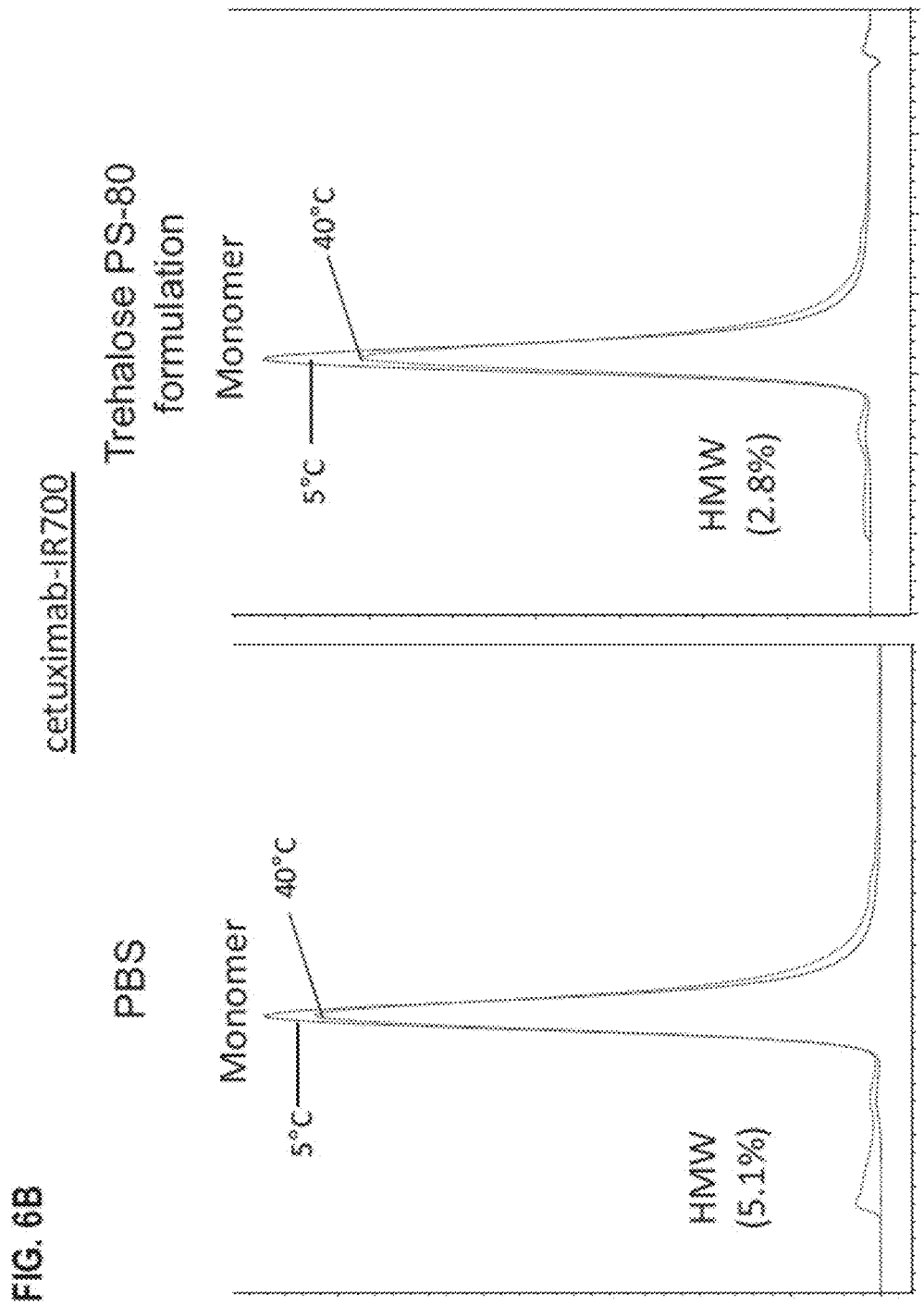
Figure 8A:
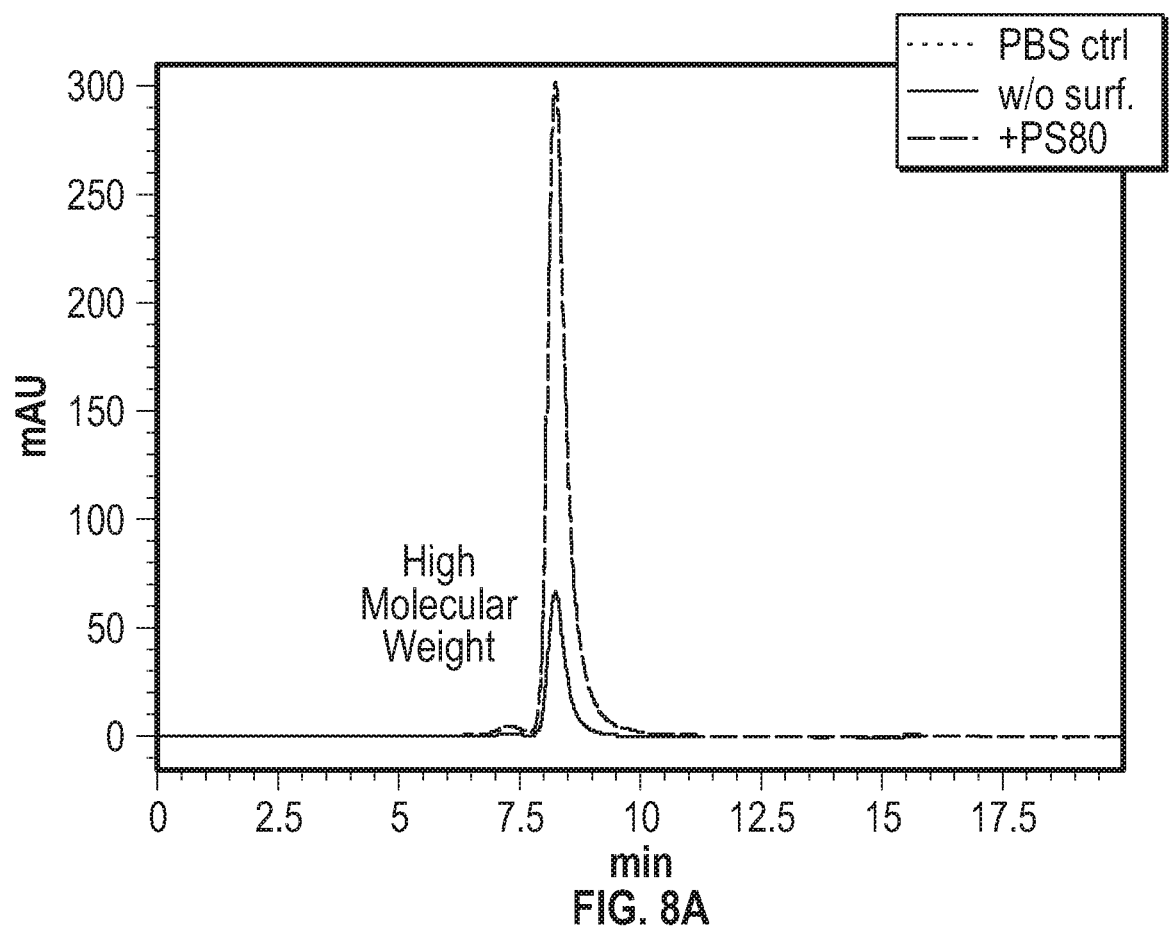
FIGS. 8A-8E display HPLC-SEC results from formulations of cetuximab-IR700 conjugates containing various surfactants: polysorbate 80 (FIG. 8A), Pluronic® Acid F-68 (F-68) (FIG. 8B), polyethylene glycol 8000 (PEG 8000) (FIG. 8C), 3-[(3-Cholamidopropyl) dimethylammonio]-1-propanesulfonate (CHAPS) (FIG. 8D) or polyethylene glycol p-(1,1,3,3-tetramethylbutyl)-phenyl ether (Triton X-100®) (FIG. 8E), following agitation. Samples without agitation (PBS ctrl) and samples without any surfactant (w/o surf.) were assessed as controls.
Figure 8B:
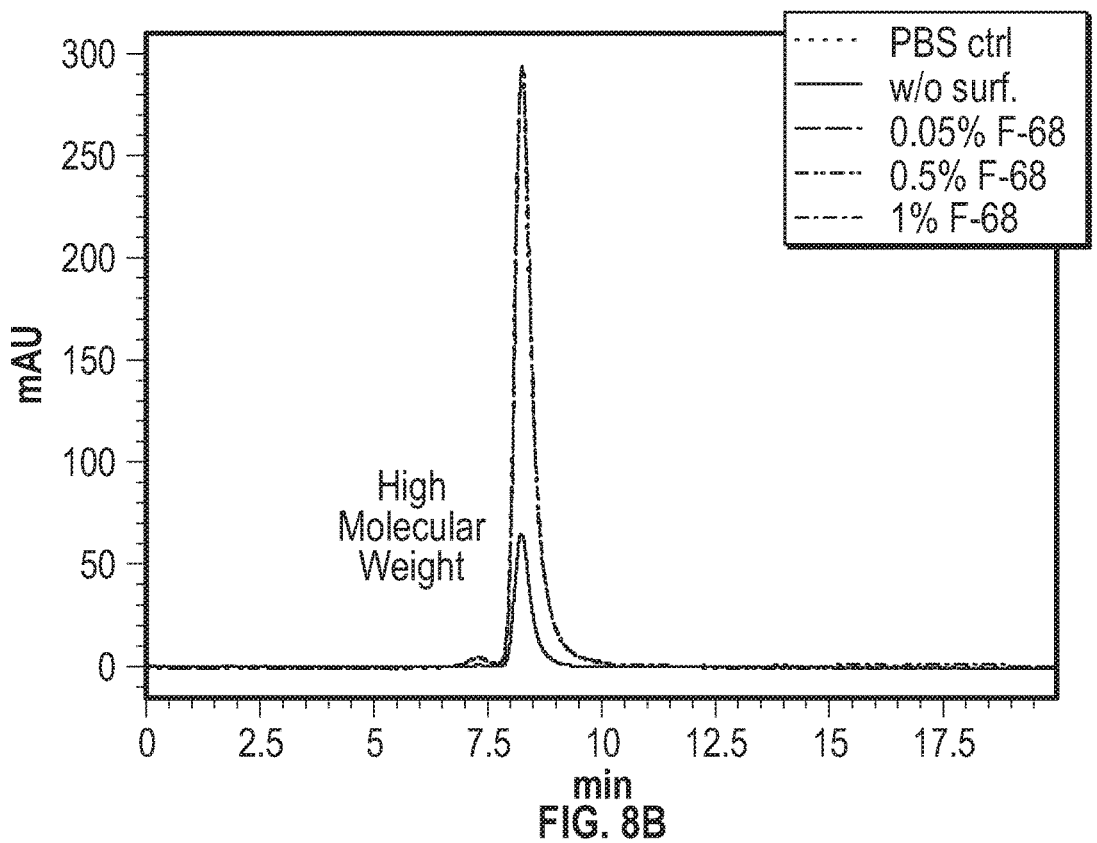
Figure 8C:
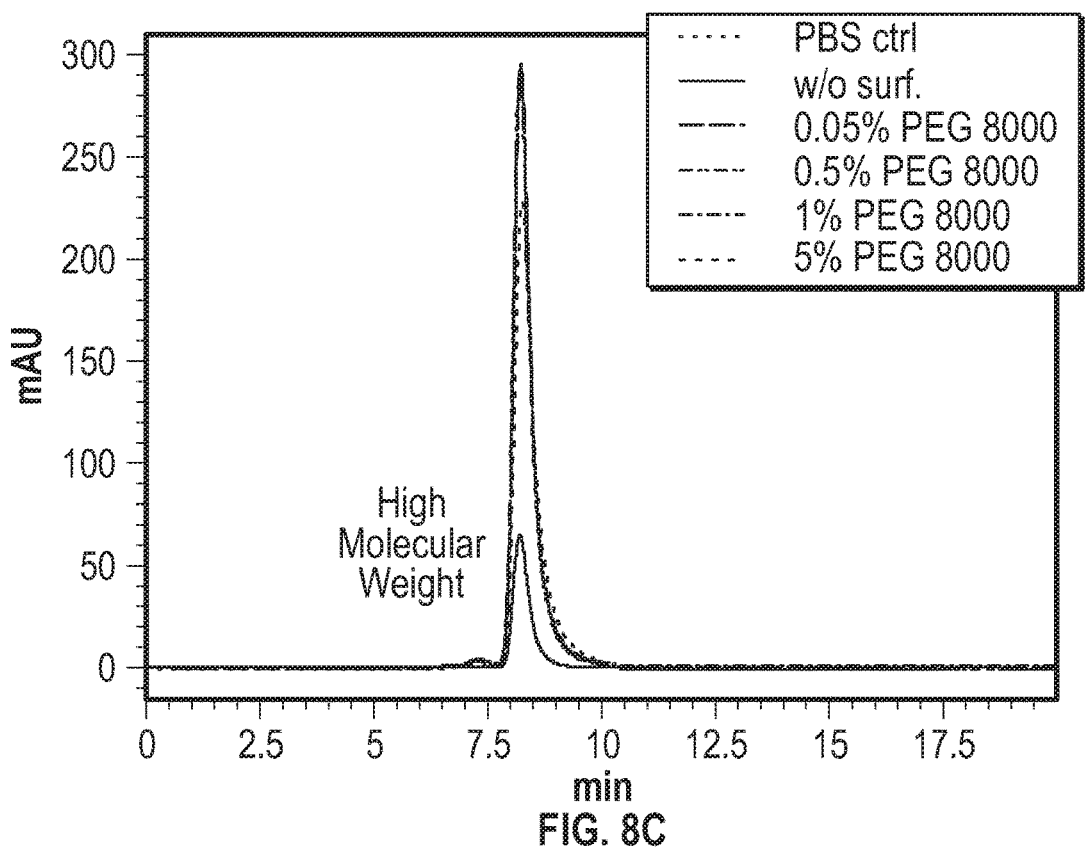
Figure 8D:
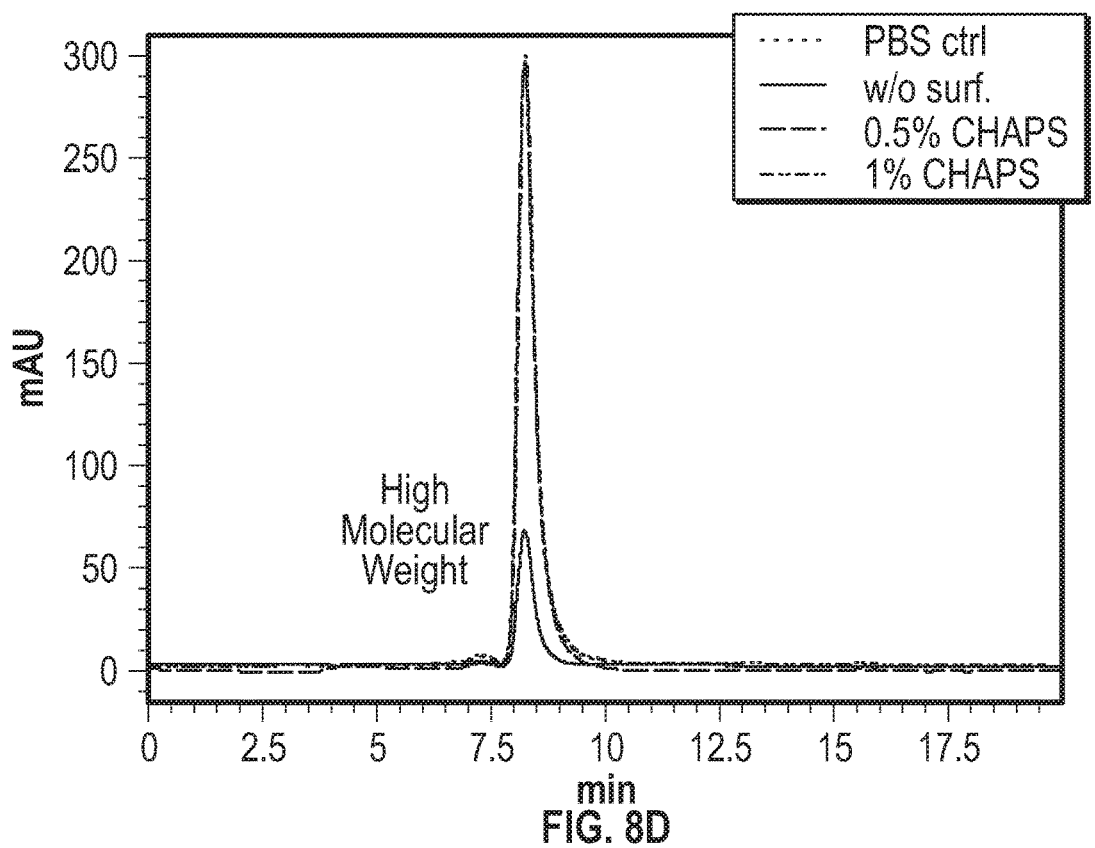
Figure 8E:
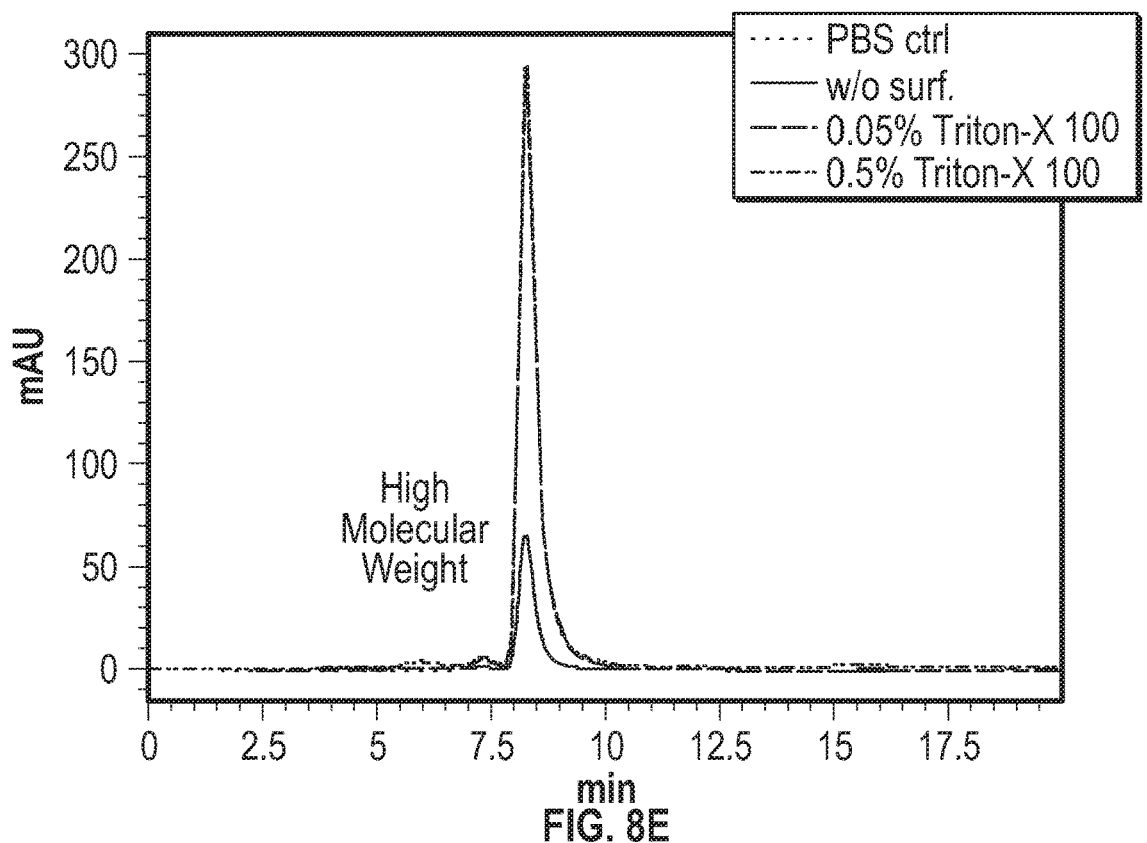

FIGS. 6A-6C show the HPLC-SEC of cetuximab-IR680 (FIG. 6A), cetuximab-IR700 (FIG. 6B) and cetuximab-IR800 (FIG. 6C), formulated in PBS or trehalose PS-80 formulation, after incubation at 40° C. or 5° C. for 1 month. The results showed that the stability of cetuximab-IR680 and cetuximab-IR700 were improved when formulated in the trehalose PS-80 formulation compared to when formulated in PBS, after a one-month incubation under thermal stress. For cetuximab-IR680, some loss of protein was observed in the sample incubated under thermal stress. For cetuximab-IR700, less high molecular weight (HMW) species formation was observed in the trehalose PS-80 formulation compared to in PBS. A small increase in low molecular weight (LMW) species formation was observed in cetuximab-IR800 formulated in the trehalose PS-80 formulation. The results showed that the trehalose PS-80 formulation resulted in improved stability of cetuximab-IR680 and cetuximab-IR700 conjugates under thermal stress conditions, compared to the same thermal stress conditions in PBS formulation.

Example 8: Evaluation of Various Antibody Dye Conjugate Formulations Under Agitation Stress Conditions The stability of various cetuximab-IR700 conjugate formulations described in the examples above were assessed after being subject to agitation stress. The samples were agitated generally as described in Example 2, assessed by HPLC-SEC, generally as described in Example 3, and visually inspected for formation of a precipitate.

Visual inspection of the agitated samples showed that cetuximab-IR700 conjugate formulated in PBS without PS-80 (no PS-80) had a significant amount of blue precipitation at the bottom of the tube. In comparison, cetuximab-IR700 conjugate formulated with PS-80 did not show any precipitation. Cetuximab-IR680 and cetuximab-IR800 conjugates formulated in PBS without PS-80 (no PS-80) each had a very small amount of precipitation at the bottom of the tube, and no precipitation was observed in conjugates formulated with PS-80.

HPLC-SEC results from PS-80 formulations are shown in FIGS. 7A-7C. As shown in FIG. 7B, the recovery of the conjugate was substantially reduced in agitated cetuximab-IR700 conjugate samples formulated in PBS without PS-80 (no PS-80). Recovery of cetuximab-IR680 (FIG. 7A) and cetuximab-IR800 (FIG. 7C) conjugates after agitation in PBS without PS-80 was not substantially affected. The results showed that cetuximab-IR700 was the most sensitive to agitation, and the presence of PS-80 in the formulation prevented protein precipitation and protein loss under agitation stress conditions.

Example 9: Screening of Cetuximab-IR700 Conjugate Formulations Containing Various Surfactants Under Agitation Stress Conditions The stability of various cetuximab-IR700 conjugate formulations containing various different surfactants were assessed after being subject to agitation stress.

Briefly, 2 mL samples of cetuximab-IR700 conical tubes at concentrations 5 mg/mL PBS pH 7.1. Various surfactants were added to each sample at various concentrations (w/v) as described in Table 7 below. The samples were agitated for 10 hours generally as described in Example 2, assessed by HPLC-SEC, generally as described in Example 3, and centrifuged and visually inspected for formation of precipitate. The formulations were compared to cetuximab-IR700 conjugate formulated in PBS without any surfactant (w/o surf.), cetuximab-IR700 conjugate without agitation (PBS ctrl) and cetuximab-IR700 conjugate formulated in 0.05% PS-80 as controls.

Similar to Example 8, visual inspection of the samples showed that cetuximab-IR700 conjugate formulated in PBS without PS-80 (no PS-80) had a significant amount of blue precipitation at the bottom of the tube, whereas cetuximab-IR700 conjugate formulated with 0.05% PS-80 did not show any precipitation. Cetuximab-IR700 conjugate formulated with F-68 at 0.05%, 0.5% and 1.0% did not exhibit precipitation. Formulation of cetuximab-IR700 conjugate with PEG 8000 did not form visible precipitation when formulated at 0.05%, 0.5%, 1.0% and 5.0%. However, at 5.0%, the PEG 8000 containing formulation exhibited increased viscosity, which may have resulted in some soluble protein loss. Formulation of cetuximab-IR700 conjugate with 0.05%, 0.5% and 1.0% CHAPS did not exhibit visible precipitate in the agitation assay. Cetuximab-IR700 conjugate formulated with 0.05% Triton X-100 exhibited comparable results to the 0.05% PS-80 control. An increase of high-molecular weight species was observed in cetuximab-IR700 conjugate formulated with 0.5% Triton X-100. The formulations of cetuximab-IR700 conjugate were analyzed by HPLC-SEC to assess for the presence of high molecular weight aggregates, protein monomer and for total protein recovery. HPLC-SEC results are shown in FIGS. 8A-8E. Presence of protein monomer and protein recovery are provided in Table 7 below.

TABLE 7

Cetuximab-IR700 Stability in Formulations with Various Surfactants Following Agitation

| Sample | % Monomer | % Recovery |
| --- | --- | --- |
| PBS Ctrl | 97.3% | — |
| PBS w/o Surfactant | 96.2% | 21% |
| PBS + 0.05% polysorbate 80 (PS-80) | 97.3% | 100% |
| PBS + 0.05% Pluronic ® Acid F-68 (F-68) | 98.4% | 99% |
| PBS + 0.5% F-68 | 98.3% | 100% |
| PBS + 1.0% F-68 | 98.4% | 99% |
| PBS + 0.05% polyethylene glycol 8000 (PEG 8000) | 97.5% | 99% |
| PBS + 0.5% PEG 8000 | 97.1% | 99% |
| PBS + 1.0% PEG 8000 | 97.6% | 100% |

TABLE 7-continued

Cetuximab-IR700 Stability in Formulations with Various Surfactants Following Agitation

| Sample | % Monomer | % Recovery |
| --- | --- | --- |
| PBS + 5.0% PEG 8000 | 98.4% | 90% |
| PBS + 0.05% 3-[(3-Cholamidopropyl) dimethylammonio]-1-propanesulfonate (CHAPS) | n/a | n/a |
| PBS + 0.5% CHAPS | 97.5% | 100% |
| PBS + 1.0% CHAPS | 97.7% | 99% |
| PBS + 0.05% polyethylene glycol p-(1,1,3,3-tetramethylbutyl)-phenyl ether (Triton X-100 ®) | 96.2% | 101% |
| PBS + 0.5% Triton X-100 | 97.0% | 103% |
| PBS + 1.0% Triton X-100 | 94.8% | n/a |

The results showed that the presence of various types of surfactants in the formulation prevented protein precipitation and protein loss under agitation stress conditions, in many cases similar to the extent with formulations containing PS-80.

Example 10: Further Evaluation of Formulations Containing Cetuximab-IR700 Conjugate Under Thermal Stress Conditions Exemplary liquid formulations containing cetuximab-IR700 dye conjugate and various protectant and surfactants were assessed under thermal stress (40° C.) conditions, generally as described in Example 7. Cetuximab-IR700 conjugate was formulated at a conjugate concentration of 5 mg/mL with buffer, protectant and surfactant as described in Tables 8A and 8B below. One milliliter (1 mL) aliquots were incubated at 40° C. for 1 or 2 weeks and then analyzed by HLPC-SEC. The various formulations tested and the results from the HPLC-SEC analysis of monomer concentrations is shown in Tables 8A and 8B.

TABLE 8A

HPLC-SEC Results of Cetuximab-IR700 Formulations with Varying Protectants

| Buffer | Protectant | Surfactant | Conditions | Monomer Content by SEC-HPLC A280 nm (%) | HMW Content by SEC-HPLC A280 nm (%) |
| --- | --- | --- | --- | --- | --- |
| PBS Ctrl pH 7.1 | NaCl | — | 5° C. Ctrl | 98.4 | 1.6 |
| | | | 40° C. 1 wk | 93.9 | 5.0 |
| | | | 40° C. 2 wk | 88.6 | 10.0 |
| 10 mM NaPO4 pH 7.1 | 9% Trehalose | 0.02% PS80 | 5° C. Ctrl | 98.3 | 1.7 |
| | | | 40° C. 1 wk | 95.4 | 4.5 |
| | | | 40° C. 2 wk | 91.5 | 7.4 |
| 10 mM NaPO4 pH 7.1 | 9% Sucrose | 0.02% PS80 | 5° C. Ctrl | 98.2 | 1.8 |
| | | | 40° C. 1 wk | 95.3 | 3.5 |
| | | | 40° C. 2 wk | 91.7 | 6.0 |
| 10 mM NaPO4 pH 7.1 | 9% Sorbitol | 0.02% PS80 | 5° C. Ctrl | 98.2 | 1.8 |
| | | | 40° C. 1 wk | 95.7 | 4.3 |
| | | | 40° C. 2 wk | 91.5 | 6.8 |
| 10 mM NaPO4 pH 7.1 | 9% Mannitol | 0.02% PS80 | 5° C. Ctrl | 98.1 | 1.9 |
| | | | 40° C. 1 wk | 95.9 | 4.1 |
| | | | 40° C. 2 wk | 92.9 | 5.8 |
| 10 mM NaPO4 pH 7.1 | 9% Maltose | 0.02% PS80 | 5° C. Ctrl | 98.0 | 2.0 |
| | | | 40° C. 1 wk | 89.7 | 9.5 |
| | | | 40° C. 2 wk | 83.0 | 15.9 |
| 10 mM NaPO4 pH 7.1 | 3% beta-cyclodextrin | 0.02% PS80 | 5° C. Ctrl | 98.1 | 1.9 |
| | | | 40° C. 1 wk | 93.9 | 6.1 |
| | | | 40° C. 2 wk | 89.9 | 8.6 |

Figure 9A:
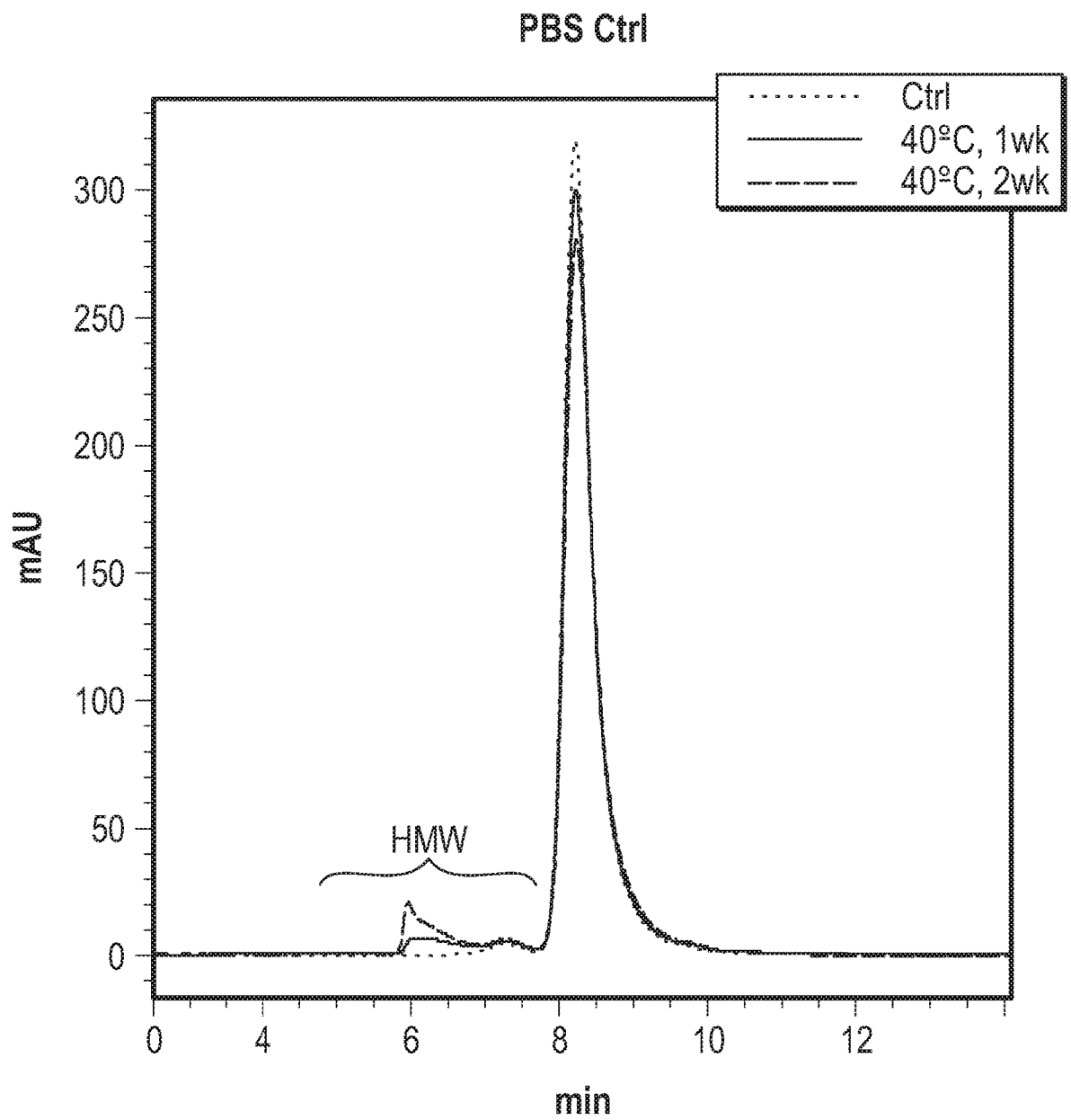
FIGS. 9A-9F display HPLC-SEC results from formulations of cetuximab-IR700 conjugates containing various protectants, surfactants or controls: PBS (FIG. 9A), 9% trehalose (FIG. 9B), 9% maltose (FIG. 9C), 9% trehalose 0.02% polysorbate 80 (PS80) (FIG. 9D), 9% trehalose 0.02% Pluronic® Acid F-68 (F-68) (FIG. 9E) or 9% trehalose 0.02% polyethylene glycol 8000 (PEG 8000) (FIG. 9F) after incubation at 40° C. for 1 week or 2 weeks.
Figure 9B:
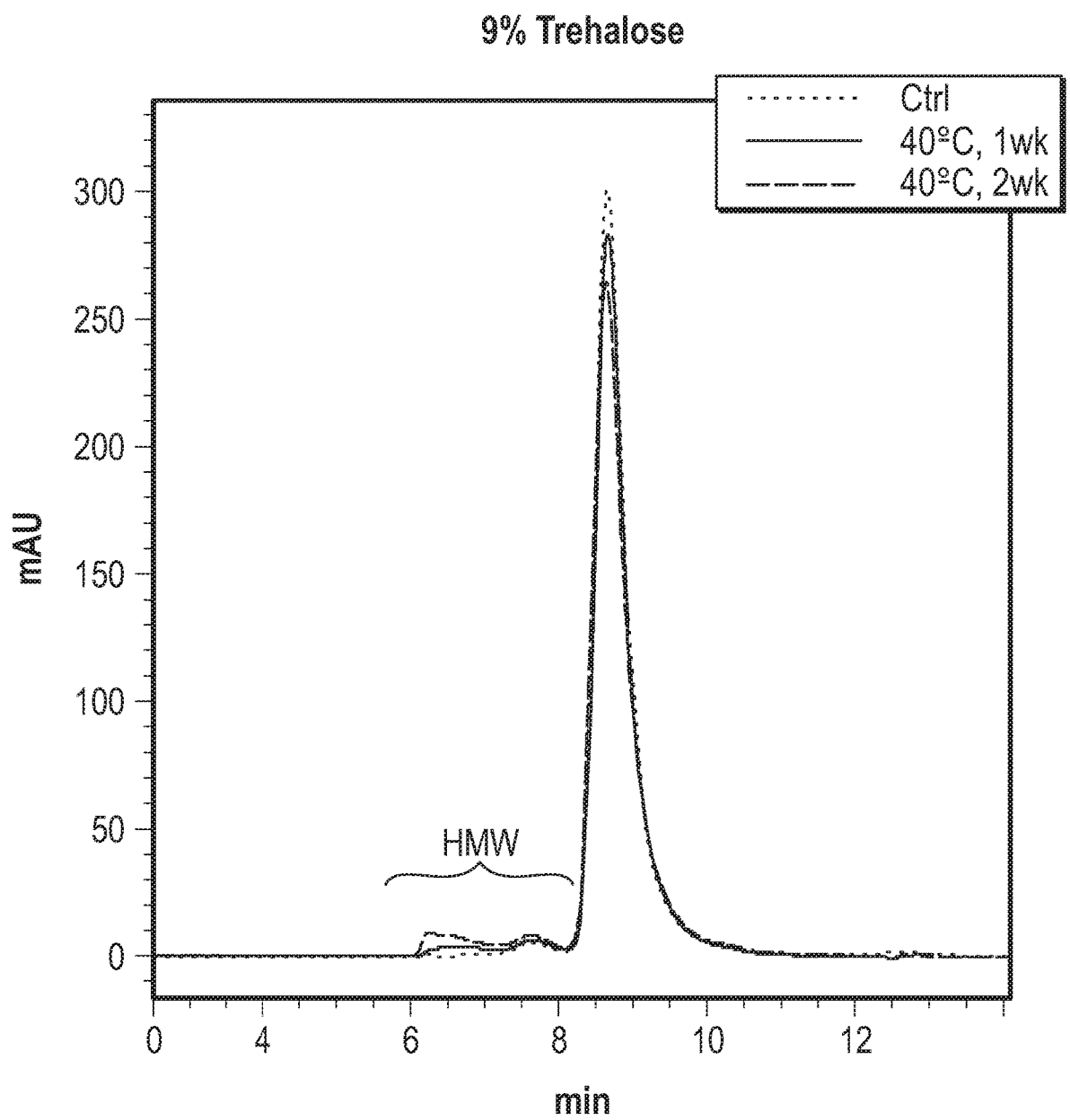
Figure 9C:
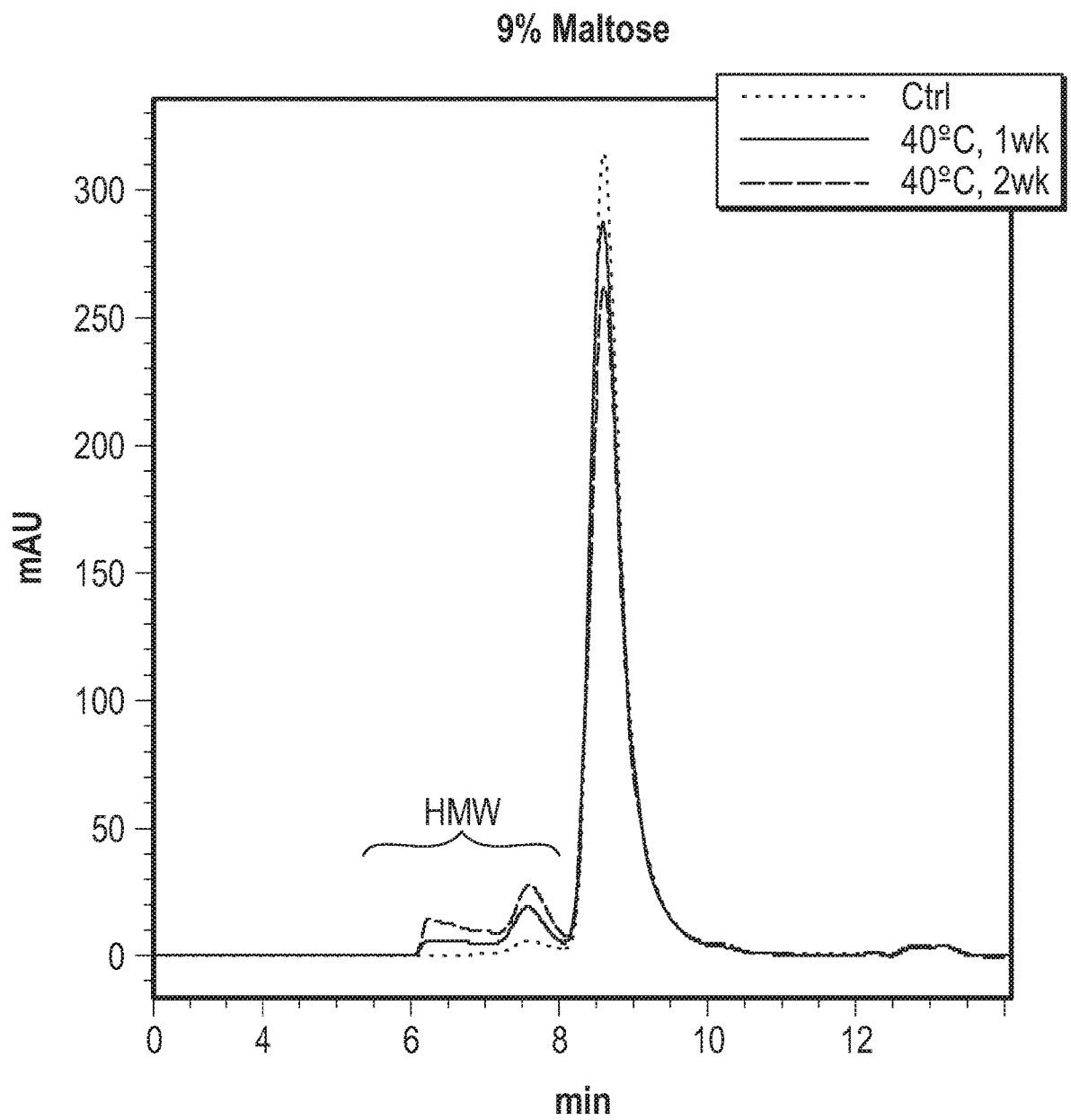

As shown in Table 8A, formulations containing protectants (also referred to as tonicifiers) trehalose, sorbitol, sucrose and mannitol resulted in improved stability in the tested conditions, for example, as indicated by reduced HMW formation. In comparison, formulations containing maltose was the least stable and resulted in higher degradation compared to the PBS control, and formulations containing beta-cyclodextrin exhibited comparable degradation to the PBS control. FIGS. 9A-9C show HPLC-SEC profiles of the PBS (FIG. 9A), 9% trehalose (FIG. 9B), 9% maltose (FIG. 9C) formulations described in Table 8A, including the difference in their high molecular weight (HMW) profiles.

TABLE 8B

HPLC-SEC Results of Cetuximab-IR700 Formulations with Varying Surfactants under Thermal Stress Conditions

| Buffer | Protectant | Surfactant | Conditions | Monomer Content by SEC-HPLC A280 nm (%) | HMW Content by SEC-HPLC A280 nm (%) |
|---|---|---|---|---|---|
| PBS Ctrl pH 7.1 | NaCl | — | 5° C. Ctrl | 98.4 | 1.6 |
| | | | 40° C. 1 wk | 93.9 | 5.0 |
| | | | 40° C. 2 wk | 88.6 | 10.0 |
| 10 mM NaPO4 pH 7.1 | 9% Trehalose | 0.02% PS80 | 5° C. Ctrl | 98.3 | 1.7 |
| | | | 40° C. 1 wk | 95.4 | 4.5 |
| | | | 40° C. 2 wk | 91.5 | 7.4 |
| 10 mM NaPO4 pH 7.1 | 9% Trehalose | 0.02% F-68 | 5° C. Ctrl | 98.2 | 1.8 |
| | | | 40° C. 1 wk | 95.8 | 4.2 |
| | | | 40° C. 2 wk | 92.3 | 6.6 |
| 10 mM NaPO4 pH 7.1 | 9% Trehalose | 0.02% PEG 8000 | 5° C. Ctrl | 98.2 | 1.8 |
| | | | 40° C. 1 wk | 94.9 | 4.0 |
| | | | 40° C. 2 wk | 92.6 | 6.0 |

Figure 9D:
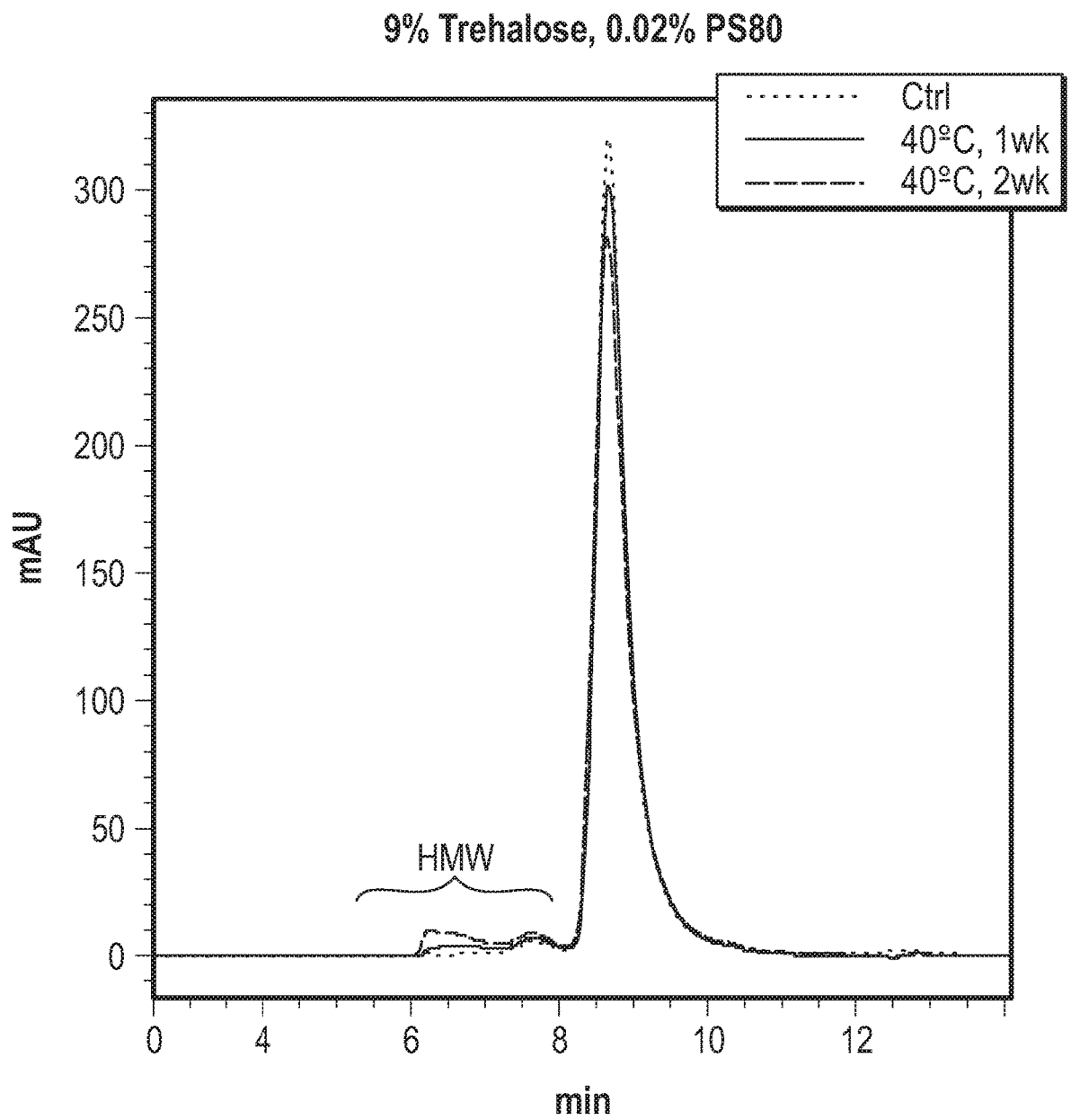
Figure 9E:
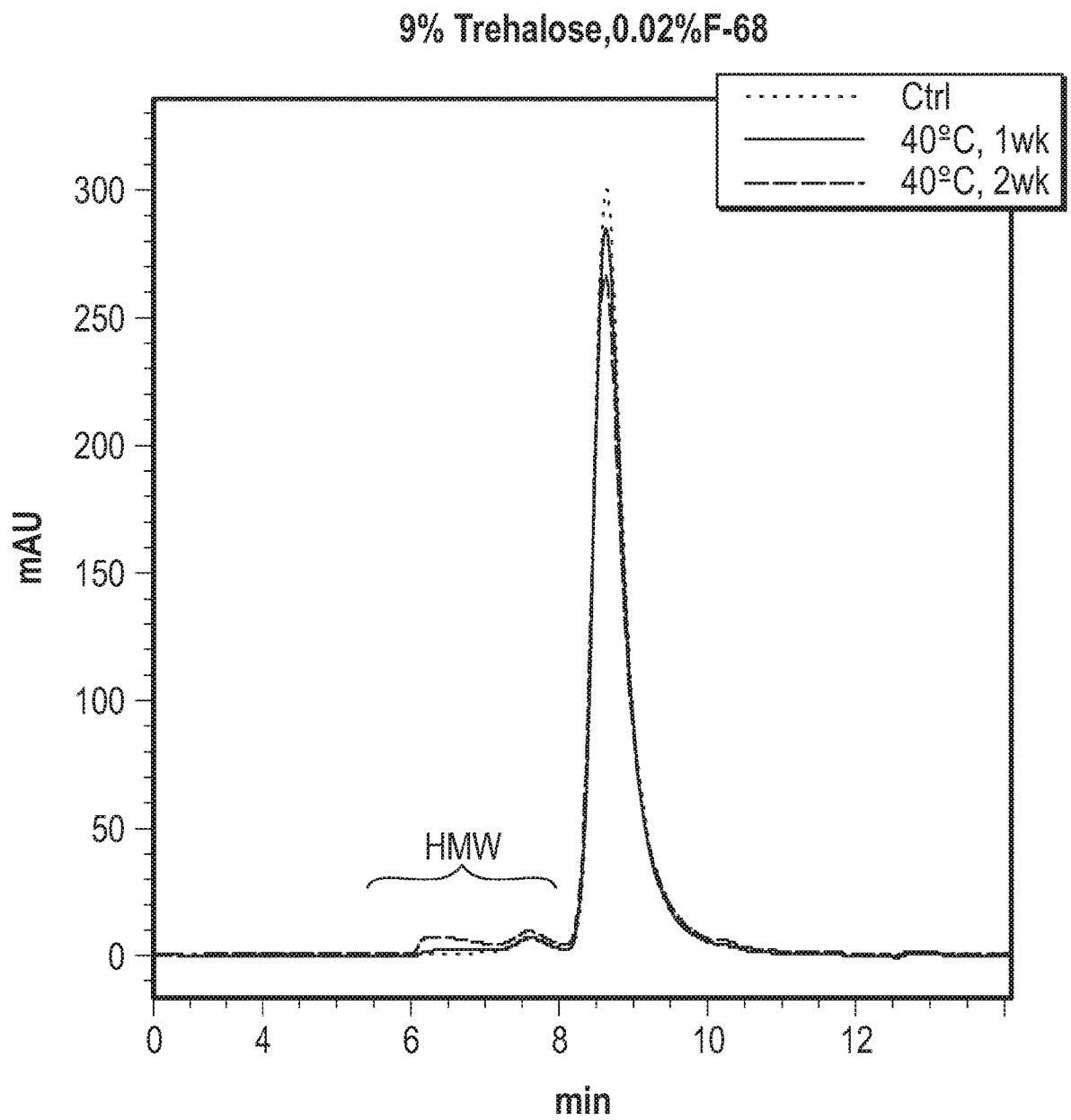
Figure 9F:
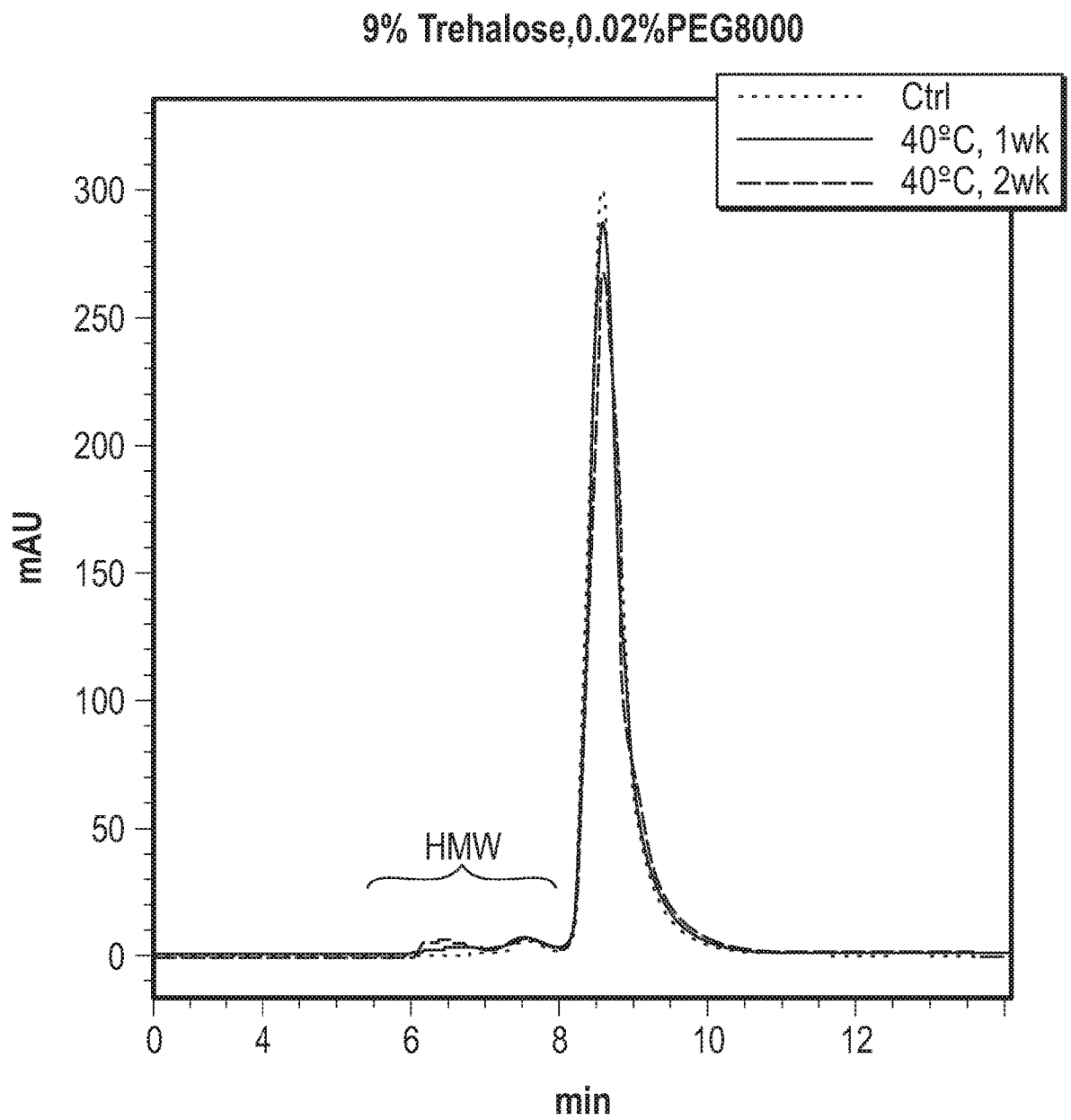

As shown above in Table 8B, formulations containing trehalose and the various surfactants exhibited comparable stability in the tested conditions. FIGS. 9D-9F show HPLC-SEC profiles of trehalose with different surfactants: 9% trehalose 0.02% polysorbate 80 (PS80) (FIG. 9D), 9% trehalose 0.02% Pluronic® Acid F-68 (F-68) (FIG. 9E) or 9% trehalose 0.02% polyethylene glycol 8000 (PEG 8000) (FIG. 9F). As shown, the stability and HMW formation were comparable between the formulations containing trehalose and the different tested surfactants PS-80, F-68 and PEG 8000.

The present invention is not to be limited in scope by the embodiments disclosed herein, which are intended as single illustrations of individual aspects of the invention, and any that are functionally equivalent are within the scope of the invention. Various modifications to the compositions and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A pharmaceutical composition comprising 5 mg/mL cetuximab-IR700 conjugate in a formulation comprising 10 mM sodium phosphate, 0.02% (w/v) polysorbate 80 and 9% (w/v) trehalose at a pH of between 6.5 and 7.5.

2. The pharmaceutical composition of claim 1, wherein the conjugate is present in at least 85% monomeric form.

3. The pharmaceutical composition of claim 1, wherein the conjugate is present in at least 95% monomeric form.

4. A container comprising the pharmaceutical composition of claim 1, wherein the container is green, blue, amber, translucent, opaque, or is covered by a material with light transmission of less than less than 30%.

5. The pharmaceutical composition of claim 1, wherein the composition is lyophilized or is formulated for lyophilization or is reconstituted from a lyophilized composition.

6. A method of treating a cancer or tumor in a subject comprising:
   a) administering to the subject a therapeutically effective amount of the pharmaceutical composition of claim 1; and
   b) after administering the composition, irradiating the cancer or tumor at a wavelength to induce phototoxic activity of the conjugate.

7. A method of treating a tumor or cancer in a subject comprising:
   (a) intravenously administering to a subject having a tumor or cancer a composition comprising a cetuximab-IR700 conjugate in a formulation comprising 10 mM sodium phosphate, 0.02% (w/v) polysorbate 80 and 9% (w/v) trehalose at pH 7.1, wherein the conjugate is administered in an amount that is or is about 640 mg/m$^2$; and
   (b) after administering the composition, irradiating the tumor or cancer at about 24±4 hours at a wavelength of 690±20 nm at a dose of at least or at least about or about 50 J cm$^{-2}$ or 100 J/cm of fiber length, thereby treating the tumor or cancer in the subject.

8. The method of claim 7, wherein the cancer is a head or neck cancer.

* * * * *